US009060971B2

(12) United States Patent
Or et al.

(10) Patent No.: US 9,060,971 B2
(45) Date of Patent: Jun. 23, 2015

(54) COMBINATION PHARMACEUTICAL AGENTS AS INHIBITORS OF HCV REPLICATION

(75) Inventors: Yat Sun Or, Watertown, MA (US); Christopher M. Owens, Cambridge, MA (US); Bradley B. Brasher, Natick, MA (US); Yao-Ling Qiu, Andover, MA (US); Lijuan Jiang, Newton, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 52 days.

(21) Appl. No.: 12/851,350

(22) Filed: Aug. 5, 2010

(65) Prior Publication Data

US 2011/0217261 A1 Sep. 8, 2011

Related U.S. Application Data

(60) Provisional application No. 61/310,579, filed on Mar. 4, 2010.

(51) Int. Cl.
*A61K 31/4184* (2006.01)
*A61K 31/13* (2006.01)
*A61K 31/4196* (2006.01)
*A61K 31/437* (2006.01)
*A61K 38/13* (2006.01)
*A61K 38/20* (2006.01)
*A61K 38/21* (2006.01)
*A61K 45/06* (2006.01)

(52) U.S. Cl.
CPC ............. *A61K 31/13* (2013.01); *A61K 31/4184* (2013.01); *A61K 31/4196* (2013.01); *A61K 31/437* (2013.01); *A61K 38/13* (2013.01); *A61K 38/2013* (2013.01); *A61K 38/204* (2013.01); *A61K 38/208* (2013.01); *A61K 38/21* (2013.01); *A61K 38/212* (2013.01); *A61K 45/06* (2013.01)

(58) Field of Classification Search
CPC .......................... A61K 31/4184; C07D 403/14
USPC ......................................... 514/394; 548/306.1
See application file for complete search history.

(56) References Cited

U.S. PATENT DOCUMENTS

| | | | |
|---|---|---|---|
| 5,935,982 | A | 8/1999 | Dykstra et al. |
| 7,141,574 | B2 | 11/2006 | Beaulieu et al. |
| 2005/0069522 | A1 | 3/2005 | Colonno et al. |
| 2006/0003942 | A1 | 1/2006 | Tung et al. |
| 2006/0058317 | A1 | 3/2006 | Gravestock et al. |
| 2006/0276511 | A1 | 12/2006 | Serrano-Wu et al. |
| 2007/0299068 | A1 | 12/2007 | Karp et al. |
| 2008/0044380 | A1 | 2/2008 | Bachand et al. |
| 2009/0004111 | A1 | 1/2009 | Rice et al. |
| 2009/0202478 | A1 | 8/2009 | Bachand et al. |
| 2009/0202483 | A1 | 8/2009 | Bachand et al. |
| 2009/0226398 | A1 | 9/2009 | Leivers et al. |
| 2009/0317360 | A1 | 12/2009 | Rai et al. |
| 2010/0221214 | A1 | 9/2010 | Or et al. |
| 2010/0221215 | A1 | 9/2010 | Qiu et al. |
| 2010/0221216 | A1 | 9/2010 | Or et al. |
| 2010/0226882 | A1 | 9/2010 | Or et al. |
| 2010/0226883 | A1 | 9/2010 | Qiu et al. |
| 2010/0233120 | A1 | 9/2010 | Bachand et al. |
| 2010/0233122 | A1 | 9/2010 | Qiu et al. |
| 2010/0260708 | A1 | 10/2010 | Belema et al. |
| 2010/0260715 | A1 | 10/2010 | Or et al. |
| 2010/0266543 | A1 | 10/2010 | Qiu et al. |
| 2010/0305117 | A1 | 12/2010 | Herdewijn et al. |
| 2010/0310512 | A1 | 12/2010 | Guo et al. |
| 2010/0316607 | A1 | 12/2010 | Or et al. |
| 2011/0008288 | A1 | 1/2011 | Or et al. |
| 2011/0064695 | A1 | 3/2011 | Qiu et al. |
| 2011/0064696 | A1 | 3/2011 | Or et al. |
| 2011/0064697 | A1 | 3/2011 | Qiu et al. |
| 2011/0064698 | A1 | 3/2011 | Or et al. |
| 2011/0070196 | A1 | 3/2011 | Qiu et al. |
| 2011/0070197 | A1 | 3/2011 | Or et al. |

FOREIGN PATENT DOCUMENTS

| | | | |
|---|---|---|---|
| WO | 2004014313 | A2 | 2/2004 |
| WO | 2006133326 | A1 | 12/2006 |
| WO | 2008021927 | A2 | 2/2008 |
| WO | 2008021928 | A2 | 2/2008 |
| WO | 2008021936 | A2 | 2/2008 |
| WO | 2008144380 | A1 | 11/2008 |
| WO | 2009020825 | A1 | 2/2009 |
| WO | 2009020828 | A1 | 2/2009 |
| WO | 2009102318 | A1 | 8/2009 |
| WO | 2009102325 | A1 | 8/2009 |
| WO | 2009102568 | A1 | 8/2009 |
| WO | 2009102633 | A1 | 8/2009 |
| WO | 2009102694 | A1 | 8/2009 |
| WO | 2010014744 | A1 | 2/2010 |
| WO | 2010017401 | A1 | 2/2010 |
| WO | 2010039793 | A1 | 4/2010 |
| WO | 2010065668 | A1 | 6/2010 |
| WO | 2010065674 | A1 | 6/2010 |
| WO | 2010065681 | A1 | 6/2010 |
| WO | 2010096302 | A1 | 8/2010 |
| WO | 2010096777 | A1 | 8/2010 |
| WO | 2010099527 | A1 | 9/2010 |
| WO | 2010111483 | A1 | 9/2010 |
| WO | 2010111534 | A1 | 9/2010 |
| WO | 2010111673 | A1 | 9/2010 |
| WO | WO 2010/099527 | * | 9/2010 |

(Continued)

OTHER PUBLICATIONS

Tomei et al, 1993, Journal of Virology, vol. 67, No. 7, p. 4017-4026.*
U.S. Appl. No. 12/702,673, Qiu, et al.

(Continued)

*Primary Examiner* — Rebecca Anderson
*Assistant Examiner* — Karen Cheng
(74) *Attorney, Agent, or Firm* — Edgar W. Harlan; Carolyn S. Elmore, Esq.; Elmore Patent Law Group, P.C.

(57) ABSTRACT

The present invention relates to pharmaceutical agents administered to a subject either in combination or in series for the treatment of a flaviviridae viral infection, for example, hepatitis C virus (HCV), wherein treatment comprises administering a compound effective to inhibit the function of the HCV NS5A protein and an additional compound or combinations of compounds having anti-HCV activity.

7 Claims, 6 Drawing Sheets

(56) References Cited

FOREIGN PATENT DOCUMENTS

| WO | 2010117635 A1 | 10/2010 |
|---|---|---|
| WO | 2010117704 A1 | 10/2010 |
| WO | 2010117977 A1 | 10/2010 |
| WO | 2010120621 A1 | 10/2010 |
| WO | 2010120935 A1 | 10/2010 |
| WO | 2010122162 A1 | 10/2010 |
| WO | 2010132538 A1 | 11/2010 |
| WO | 2010132601 A1 | 11/2010 |
| WO | 2010138368 A1 | 12/2010 |
| WO | 2010138488 A1 | 12/2010 |
| WO | 2010138790 A1 | 12/2010 |
| WO | 2010138791 A1 | 12/2010 |
| WO | 2010144646 A2 | 12/2010 |
| WO | 2011004276 A1 | 1/2011 |
| WO | 2011009084 A1 | 1/2011 |
| WO | 2011015657 A1 | 2/2011 |
| WO | 2011015658 A1 | 2/2011 |
| WO | 2011026920 A1 | 3/2011 |
| WO | 2011028596 A1 | 3/2011 |
| WO | 2011059850 A1 | 5/2011 |
| WO | 2011081918 A1 | 7/2011 |

OTHER PUBLICATIONS

International Search Report for PCT/US10/44591, dated Sep. 29, 2010.

Sofia, "R7128, A Potent and Selective Nucleoside Inhibitor of HCV NS5B Polymerase: An Overview of Clinical Efficacy and Progress Toward Second Generation Inhibitors," Pharmasset, CHI:HCV Drug Discovery, 2008.

Bressanelli, et al., "Crystal Structure of the RNA-dependent RNA Polymerase of Hepatitis C Virus," PNAS, 96 (23):13034-13039, 1999.

* cited by examiner

US 9,060,971 B2

COMBINATION PHARMACEUTICAL AGENTS AS INHIBITORS OF HCV REPLICATION

RELATED APPLICATION

This application claims the benefit of U.S. Provisional Application No. 61/310,579 filed Mar. 4, 2010. The entire teachings of the above application are incorporated herein by reference.

TECHNICAL FIELD

The present invention relates to pharmaceutical agents administered to a subject either in combination or in series for the treatment of a flaviviridae viral infection, for example, hepatitis C virus (HCV), wherein treatment comprises administering a compound effective to inhibit the function of the HCV NS5A protein and an additional compound or combinations of compounds having anti-HCV activity. Compounds which can inhibit the function of the NS5A protein encoded by HCV are described. Exemplary additional agents having anti-HCV activity are those that are effective to inhibit the function of a target selected from HCV metalloprotease, HCV serine protease, HCV polymerase, HCV helicase, HCV NS4B protein, HCV entry, HCV assembly, HCV egress, HCV NS5A protein and IMPDH, and/or cyclosporine analogs and/or a nucleoside analog for the treatment of an HCV or flaviviridae infection.

BACKGROUND OF THE INVENTION

The present invention is generally directed to combinations of antiviral compounds, and more specifically directed to combination pharmaceutical agents, which can inhibit the function of the NS5A protein encoded by Hepatitis C virus (HCV) and the NS3 protease encoded by HCV.

HCV is a major human pathogen, infecting an estimated 170 million persons worldwide-roughly five times the number infected by human immunodeficiency virus type 1. A substantial fraction of these HCV infected individuals develop serious progressive liver disease, including cirrhosis and hepatocellular carcinoma. (Lauer, G. M.; Walker, B. D. N. Eng. J. Med. (2001), 345, 41-52).

Presently, the most effective HCV therapy employs a combination of pegylated alpha-interferon and ribavirin, leading to sustained efficacy in 50% of patients and a treatment that is superior to unmodified alpha-interferon as monotherapy (Zeuzem, S. et al. N. Engl. J. Med. (2000), 343, 1666-1672). However, even with experimental therapeutic regimens involving combinations of pegylated alpha-interferon and ribavirin, a substantial fraction of patients do not have a sustained reduction in viral load. Thus, there is a clear and unmet need for effective therapeutics for the treatment of HCV infection.

HCV is a positive-sense single stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive-sense single stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The positive-sense single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and assisting in the membrane localization of NS3 and other viral replicase components.

The complex formation of the NS3 protein with NS4A seems necessary to the processing events, enhancing the proteolytic efficiency at all of the sites. The NS3 protein also exhibits nucleoside triphosphatase and RNA helicase activities. NS5B is an RNA-dependent RNA polymerase that is involved in the replication of HCV.

Among the compounds that have demonstrated efficacy in inhibiting HCV replication, as selective HCV serine protease inhibitors, are the peptide compounds disclosed in Patent No. WO/1999/007733, WO/2005/007681, WO/2005/028502, WO/2005/035525, WO/2005/037860, WO/2005/077969, WO/2006/039488, WO/2007/022459, WO/2008/106058, WO 2008/106139, WO/2000/009558, WO/2000/009543, WO/1999/064442, WO/1999/007733, WO/1999/07734, WO/1999/050230 and WO/1998/017679. NS5B polymerase inhibitors have also demonstrated activity. These agents include but are not limited to other inhibitors of HCV RNA dependent RNA polymerase such as, for example, nucleoside type polymerase inhibitors described in WO01/90121(A2), or U.S. Pat. No. 6,348,587B1 or WO01/60315 or WO01/32153 or non-nucleoside inhibitors such as, benzimidazole polymerase inhibitors described in EP 162196A1 or WO02/04425. However, none of these compounds have, to date, progressed beyond clinical trials (De Clercq, E. J. Clin. Virol. 2001 22 73-89).

In addition to the combinations of pegylated alpha-interferon and ribavirin, other combinations of compounds useful for treating HCV-infected patients are desired which selectively inhibit HCV viral replication. In particular, pharmaceutical agents which are effective to inhibit the function of the NS5A protein in combination with those effective to inhibit other viral targets are desired. The HCV NS5A protein is described, for example, in Tan, S.-L.; Katzel, M. G. Virology (2001) 284, 1-12, and in Park, K.-J.; Choi, S.-H, J. Biological Chemistry (2003). The relevant patent disclosures describing the synthesis of HCV NS5A inhibitors are: US 2009/0202478; US 2009/0202483; WO 2009/020828; WO 2009/020825; WO 2009/102318; WO 2009/102325; WO 2009/102694; WO 2008/144380; WO 2008/021927; WO 2008/021928; WO 2008/021936; WO 2006/133326; WO 2004/014852; WO 2008/070447; WO 2009/034390; WO 2006/079833; WO 2007/031791; WO 2007/070556; WO 2007/070600; WO 2008/064218; WO 2008/154601; WO 2007/082554; WO 2008/048589; WO 2010/017401; WO 2010/

065668; WO 2010/065674; WO 2010/065681, the contents of each of which are expressly incorporated by reference herein.

SUMMARY OF THE INVENTION

The present invention features pharmaceutical compositions comprising a combination of a first compound that inhibits the function of the HCV NS5A protein and a second agent or combinations of agents having anti-viral activity and a pharmaceutically acceptable excipient or carrier. The present invention also encompasses methods for the treatment of a viral disease comprising co-administering a therapeutically effective amount of a compound effective to inhibit the function of the HCV NS5A protein and an additional agent or combination of agents having anti-HCV activity. In some aspects, the agent having anti-viral activity is an agent having anti-HCV activity. In certain embodiments, the viral disease is caused by a virus which is a member of one or more of the following groups: single-stranded RNA viruses, flaviviridae viruses (e.g., a hepacivirus such as HCV, flavivirus or pestivirus), and hepatic viruses. HCV, for example, is a positive-sense single-stranded RNA virus, a flaviviridae virus, and a hepatic virus. In certain embodiments, the viral disease is caused by the hepatitis C virus. Additional exemplary viruses are described herein.

Preferred compounds effective to inhibit the function of the HCV NS5A protein are small molecule compounds having a structure corresponding to Formula (I):

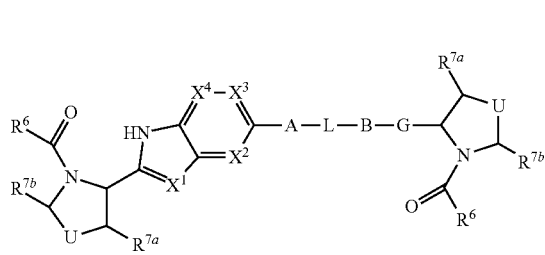

or a pharmaceutically acceptable salt thereof, wherein:

A and B are each independently absent or a monocyclic or polycyclic group independently selected from the group consisting of aryl, heteroaryl, heterocyclic, $C_3$-$C_8$ cycloalkyl, and $C_3$-$C_8$ cycloalkenyl, each optionally substituted; preferably optionally substituted aryl or optionally substituted heteroaryl;

L is absent or a linear aliphatic group; wherein the preferred said linear group is selected from the group consisting of optionally substituted $C_1$-$C_4$ alkyl, optionally substituted $C_2$-$C_4$ alkenyl, and optionally substituted $C_2$-$C_4$ alkynyl;

Wherein at least one of A, B and L is present;

G is an optionally substituted 5-membered heteroaryl containing one or more nitrogen atoms or optionally substituted 5/6-membered fused heteroaryl, wherein the 5-membered ring of said 5/6-membered fused heteroaryl contains one or more nitrogen atoms and is attached to the nitrogen-containing heterocycle, and wherein the 6-membered ring of said 5/6-membered fused heteroaryl is attached to one of groups B, L and A and is aryl or heteroaryl; preferably, optionally substituted imidazolyl, optionally substituted benzimidazolyl or optionally substituted imidazopyridyl;

$R^6$ at each occurrence is independently selected from the group consisting of O($C_1$-$C_8$ alkyl), amino, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, and heteroaryl, each optionally substituted; preferably, optionally substituted $C_1$-$C_8$ alkyl; more preferably $C_1$-$C_8$ alkyl optionally substituted with amino, hydroxy, protected amino or O($C_1$-$C_4$ alkyl);

$X^1$ at each occurrence is independently N or C($R^1$); preferably N;

$X^2$, $X^3$ and $X^4$ at each occurrence are each independently selected from N and C($R^1$); preferably CH;

$R^1$ at each occurrence is independently hydrogen, halogen, hydroxy, optionally substituted $C_1$-$C_4$ alkyl, or O($C_1$-$C_4$ alkyl); preferably, hydrogen;

U is absent or independently selected from O, S, S(O), $SO_2$, NC(O)—($C_1$-$C_4$ alkyl), C(O), protected carbonyl, $OCH_2$, $OCH_2CH_2$, $SCH_2$, $SCH_2CH_2$, $C(R^7)_2$, $C(R^7)_2C(R^7)_2$, or C=C($R^2$)$_2$; preferably, $CH_2$, C=N—OMe, or C=$CH_2$;

$R^2$ at each occurrence is independently hydrogen, halogen, optionally substituted $C_1$-$C_4$ alkyl, optionally substituted aryl, or optionally substituted heteroaryl;

$R^7$ at each occurrence is independently selected from the group consisting of hydrogen, halogen, cyano, hydroxy, O($C_1$-$C_4$ alkyl), S($C_1$-$C_4$ alkyl), amino optionally substituted with one or two $C_1$-$C_4$ alkyl, optionally substituted aryl, optionally substituted heteroaryl, and optionally substituted $C_1$-$C_4$ alkyl; preferably hydrogen, halogen or hydroxy;

Alternatively two geminal $R^7$ groups can be taken together with the carbon atom to which they are attached to form a spiro, optionally substituted 3- to 7-membered cycloalkyl, cycloalkenyl or heterocyclic ring; preferably, spiro cyclopropyl;

$R^{7a}$ and $R^{7b}$ at each occurrence are each independently selected from the group consisting of hydrogen, optionally substituted aryl, and optionally substituted $C_1$-$C_4$ alkyl; preferably hydrogen or methyl;

Alternatively, $CHR^{7a}$—U or $CHR^{7b}$—U can be taken together to form a group selected from CH=CH, fused and optionally substituted $C_3$-$C_8$ cycloalkyl, fused and optionally substituted aryl, or fused and optionally substituted heterocyclic; preferably, fused and optionally substituted cyclopropyl; and Yet alternatively, U, $R^{7a}$, and $R^{7b}$ can be taken together with the carbon atoms to which they are attached to form a bridged, optionally substituted 4- to 7-membered ring including cycloalkyl, cycloalkenyl and heterocyclic; preferably bridged cyclopentyl.

Each preferred group stated above can be taken in combination with one, any or all other preferred groups.

In another aspect, the present invention provides a pharmaceutical composition comprising a therapeutically effective amount of a compound or combination of compounds of the present invention, or a pharmaceutically acceptable salt thereof, in combination with a pharmaceutically acceptable carrier or excipient.

The compound that inhibits the function of the HCV NS5A protein can inhibit viral RNA replication in a cell culture system (replicon), preferably with a therapeutic index (TI, $CC_{50}/EC_{50}$) approaching or exceeding 100-fold. Such compounds have been found to be specific inhibitors of HCV replication and may inhibit related viruses (dengue, west nile virus, yellow fever virus, BVDV) and the BVDV replicon. HCV replicon mutants conferring resistance were selected and resistant cell lines indicate that NS5A is the major target of the compounds of the present invention.

The additional agent or combination of agents having anti-viral or anti-HCV activity may be agents such as, for example, an interferon, an interleukin, interfering RNA, antisense RNA, imiquimod, ribavirin or another small molecule inhibitor of HCV. Desirably, an agent having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, inosine monophophate dehydrogenase ("IMPDH"), cyclophilins and a nucleoside analog for the treatment of an HCV infection.

The present invention provides methods for treating patients infected with HCV, comprising co-administering to the patient a therapeutically effective amount of a compound that inhibits the function of the HCV NS5A protein and a second agent having anti-viral activity. In some aspects, the agent having anti-viral activity comprises an agent having anti-HCV activity. It is to be understood that the term "co-administering" encompasses administering at the same time (for example, within the same pharmaceutical composition) and administering at different times (for example, the agent that inhibits the function of the HCV NS5A protein can be administered before or after an agent that has anti-viral or anti-HCV activity). Additionally, the present invention provides methods of inhibiting the function of HCV NS5A protein by contacting the HCV NS5A protein with the combination described herein. By virtue of the present invention, it is now possible to provide improved pharmaceutical compositions and methods of treatment comprising a combination of a compound that inhibits the function of the HCV NS5A protein and an additional agent or combination of agents having anti-viral activity. Specifically, the present invention provides a combination of a pharmaceutical agent that inhibits the function of the NS5A protein and a second agent or combinations of agents having anti-HCV activity.

In still another embodiment, the present invention provides a method of inhibiting the replication of an RNA-containing virus comprising contacting said virus with a therapeutically effective amount of the combination of agents described, or a pharmaceutically acceptable salts, prodrugs, salts of a pro drug, stereoisomers, tautomers, solvates, or combination of any of thereof. Particularly, this invention is directed to methods of inhibiting the replication of hepatitis C virus.

In yet another embodiment, the present invention provides a method of treating or preventing infection caused by an RNA-containing virus comprising administering to a patient in need of such treatment a therapeutically effective amount of a combination of agents described herein, or a pharmaceutically acceptable salt forms, prodrugs, salts of a prodrug, stereoisomers, or tautomers, solvates, or combination of any of thereof. Particularly, this invention is directed to methods of treating or preventing infection caused by hepatitis C virus.

Yet another embodiment of the present invention provides the use of combinations of compounds of the present invention, or a therapeutically acceptable salt forms, prodrugs, salts of a prodrug, stereoisomers or tautomers, solvates, or combination thereof, as defined hereinafter, in the preparation of a medicament for the treatment or prevention of infection caused by RNA-containing virus, specifically hepatitis C virus (HCV).

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
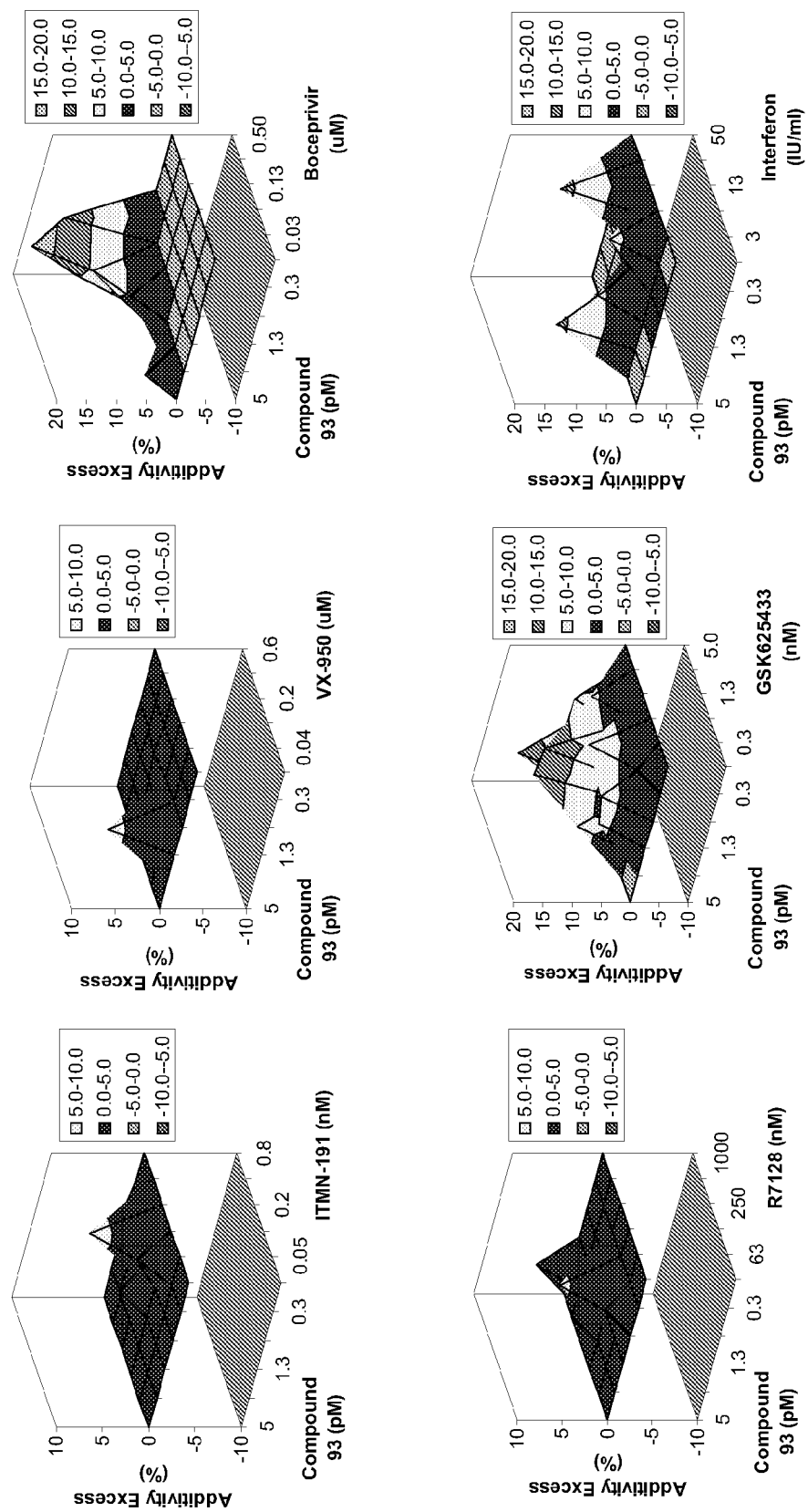
FIG. 1 is a graphical representation of the additivity excess at each combination concentration contributing to the overall synergy score for compound 93 in combination with the indicated antiviral compounds.

The words "a" or "an" are meant to encompass one or more unless otherwise specified. For example, the term "an agent that inhibits anti-HCV activity" is meant to encompass one or more agents that inhibit anti-HCV activity.

In one embodiment, the pharmaceutical compositions of the present invention can comprise a compound of Formula (I) in an amount effective to inhibit the function of the HCV NS5A protein and an additional agent having anti-HCV activity. In another embodiment, the invention encompasses methods for treatment of a viral infection comprising administering to a patient in need thereof a compound of Formula (I) effective to inhibit the function of the HCV NS5A protein and a second agent having anti-HCV activity. The combinations of the present invention provide pharmaceutical compositions and/or treatments which inhibit hepatitis C virus (HCV) replication, and can provide a safe and effective treatment for HCV infection.

Compounds of Formula (I) are described which inhibit RNA replication in a cell culture system (replicon) and have a therapeutic index (TI $CC_{50}/EC_{50}$) of greater than 100-fold. A structure-activity relationship has been observed resulting in low picomolar potency for compounds evaluated in the replicon system. Exemplary compounds of Formula (I) exhibit $EC_{50}$ values of <5 nanomolar ("nM").

Compounds of Formula (I) have utility in inhibiting the replication of RNA-containing viruses, including, for example, HCV. Methods for the preparation and use of exemplary compounds having the Formula (I) as well as other compounds that inhibit the replication of RNA-containing virus have been described in copending U.S. application Ser. No. 12/702,673 filed Feb. 9, 2010 entitled "Linked Dibenzimidiazole Antivirals"; U.S. application Ser. No. 12/702,692 filed Feb. 9, 2010 entitled "Linked Dibenzimidiazole Derivatives"; U.S. application Ser. No. 12/702,802 filed Feb. 9, 2010 entitled "Linked Dibenzimidiazole Derivatives"; U.S. application Ser. No. 12/707,190 filed Feb. 17, 2010 entitled "Linked Diimidazole Derivatives"; U.S. application Ser. No. 12/707,200 filed Feb. 17, 2010 entitled "Linked Diimidazole Derivatives"; U.S. application Ser. No. 12/707,210 filed Feb. 17, 2010 entitled "Hepatitis C Virus Inhibitors"; U.S. application Ser. No. 12/714,583 filed Mar. 1, 2010 entitled "Novel Benzimidazole Derivatives"; and U.S. application Ser. No. 12/714,576 filed Mar. 1, 2010 entitled "Hepatitis C Virus Inhibitors".

In one embodiment, the compound that inhibits the function of the HCV NS5A protein is a compound of Formula (I), or a pharmaceutically acceptable salt thereof; wherein G is illustrated by one of the following heteroaryl groups:

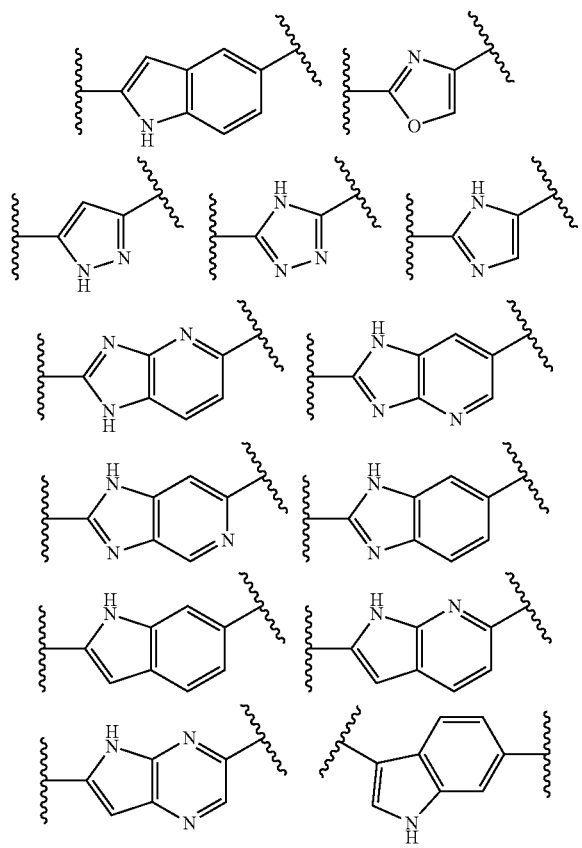

wherein each of the above shown heteroaryl groups is optionally substituted.

In yet another embodiment, the compound that inhibits the function of the HCV NS5A protein is a compound of Formula (IIa) or (IIb), or a pharmaceutically acceptable salt thereof;

(IIa)

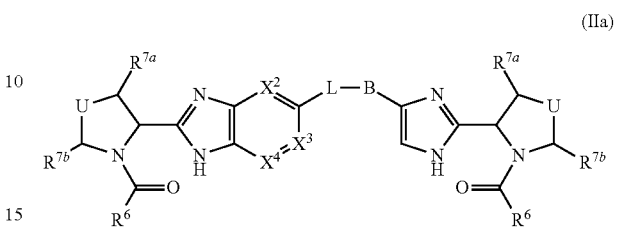

(IIb)

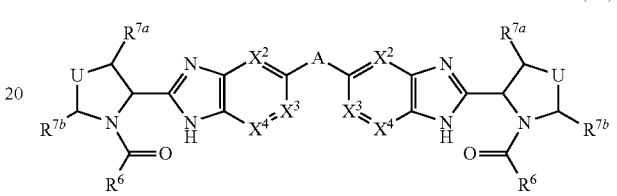

wherein U, $R^6$, $R^{7a}$, and $R^{7b}$ are as previously defined; one of $X^2$, $X^3$ and $X^4$ is N or CH, the other two of $X^2$, $X^3$ and $X^4$ are CH; A and B are each independently phenyl, monocyclic heteroaryl, bicyclic aryl, or bicyclic heteroaryl, each optionally substituted; L is optionally substituted $C_2$-$C_4$ alkenyl, or optionally substituted $C_2$-$C_4$ alkynyl.

In still another embodiment, the compound that inhibits the function of the HCV NS5A protein is a compound of Formulae (IIc, IId, IIe or IIf), or a pharmaceutically acceptable salt thereof;

(IIc)

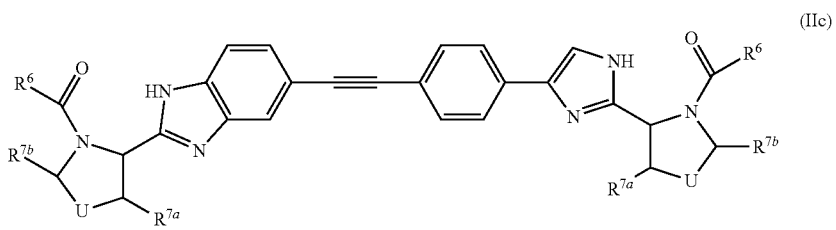

(IId)

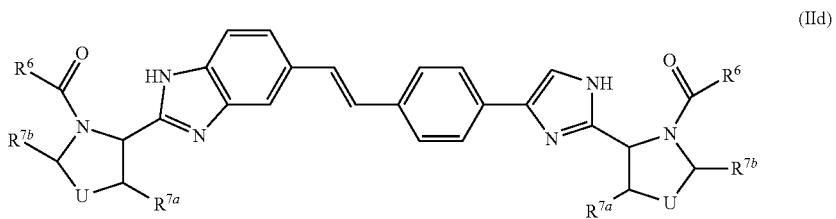

(IIe)

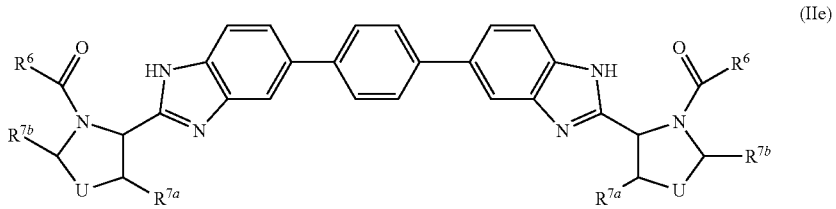

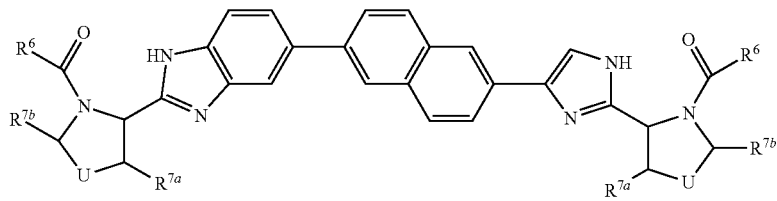

(IIf)

wherein $R^6$ is $C_1$-$C_8$ alkyl optionally substituted with amino, hydroxy, protected amino, or O($C_1$-$C_4$ alkyl); U at each occurrence is independently $CH_2$, CHF, CHMe, $CF_2$, C=$CH_2$, C=$CF_2$, or C($R^7$)$_2$, wherein the two geminal $R^7$ groups are taken together with the carbon to which they are attached to form a spiro cyclopropyl; $R^{7a}$ is hydrogen; and $R^{7b}$ is hydrogen or methyl; or alternatively, $R^{7a}$ and U or U and $R^{7b}$ are taken together with the carbon to which they are attached to form a fused cyclopropyl, and the other of $R^{7b}$ or $R^{7a}$ is hydrogen; or yet alternatively U, $R^{7a}$ and $R^{7b}$ are taken together with the carbon to which they are attached to form a bridged $C_4$-$C_7$ cycloalkyl.

In still another embodiment, the compound that inhibits the function of the HCV NS5A protein is a compound of Formula (I), or a pharmaceutically acceptable salt thereof; wherein

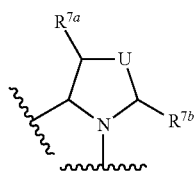

at each occurrence is independently illustrated by one of the following groups:

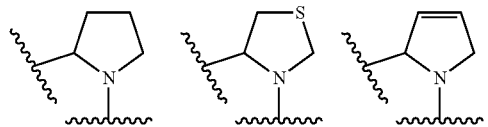

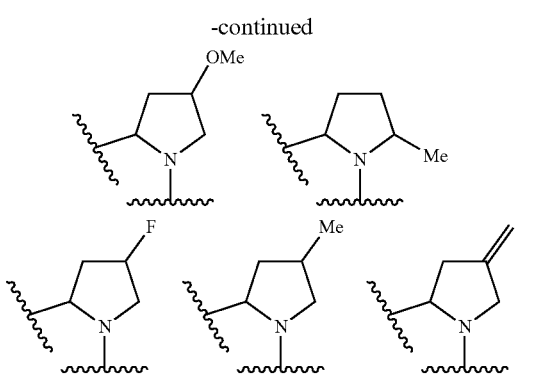

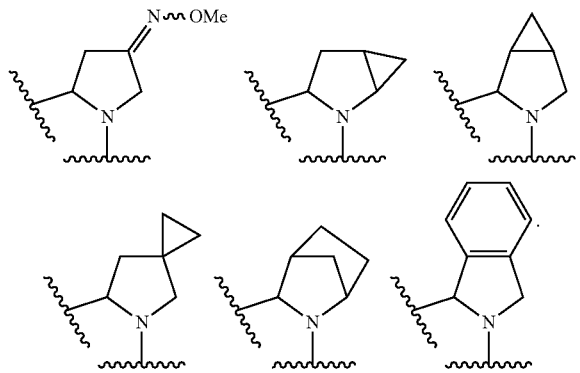

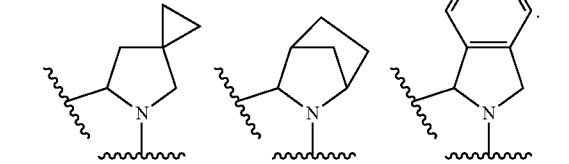

Representative compounds of Formula (I) are those selected from compounds 1-131 compiled in Table 1:

TABLE 1

| Compound | Structure |
|---|---|
| 1 | 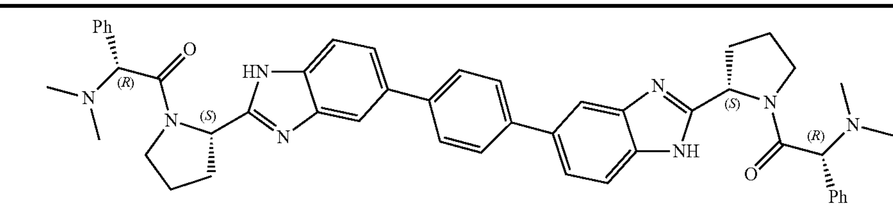 |
| 2 | 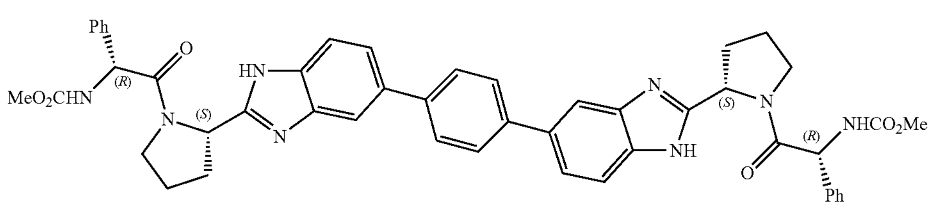 |

TABLE 1-continued

| Compound | Structure |
|---|---|
| 3 | 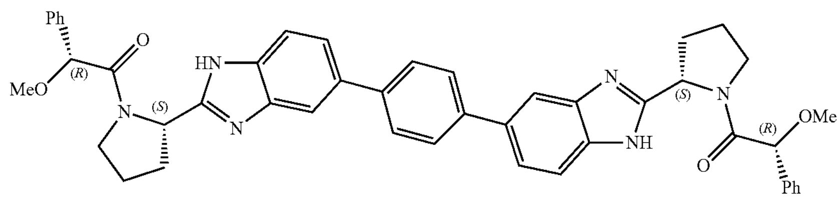 |
| 4 | 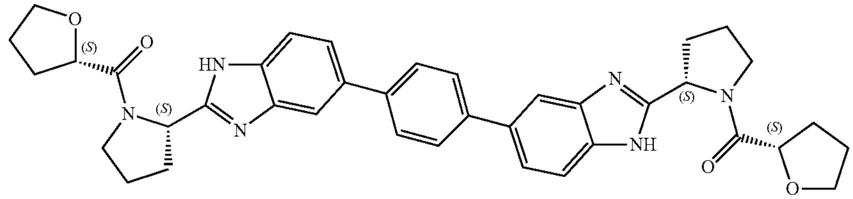 |
| 5 | 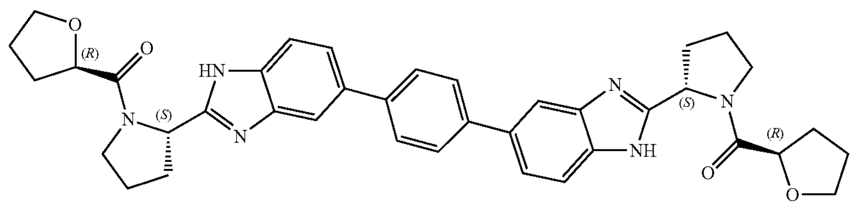 |
| 6 | 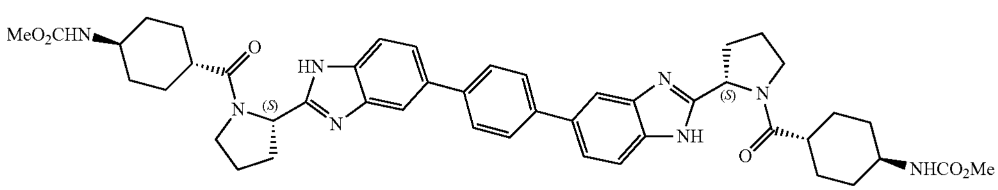 |
| 7 | 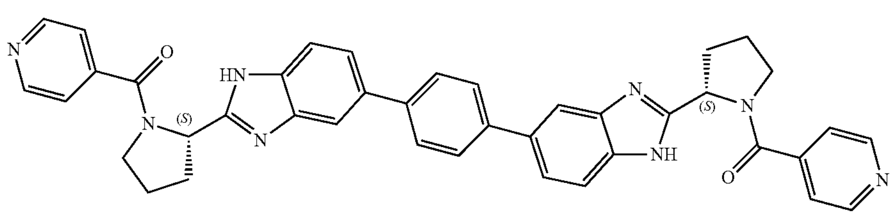 |
| 8 | 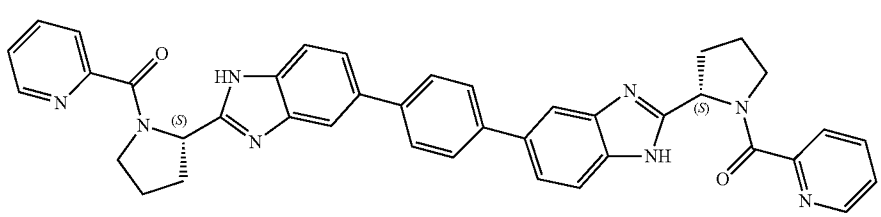 |
| 9 | 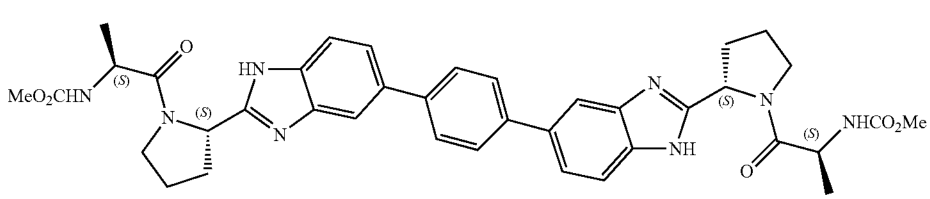 |

TABLE 1-continued

| Compound | Structure |
|---|---|
| 10 | 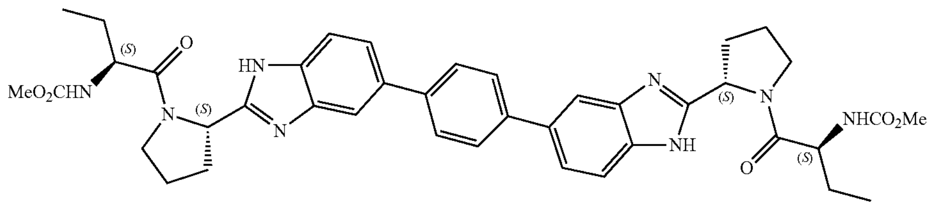 |
| 11 | 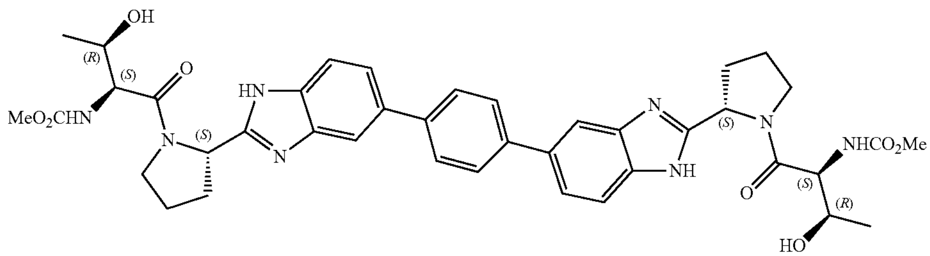 |
| 12 | 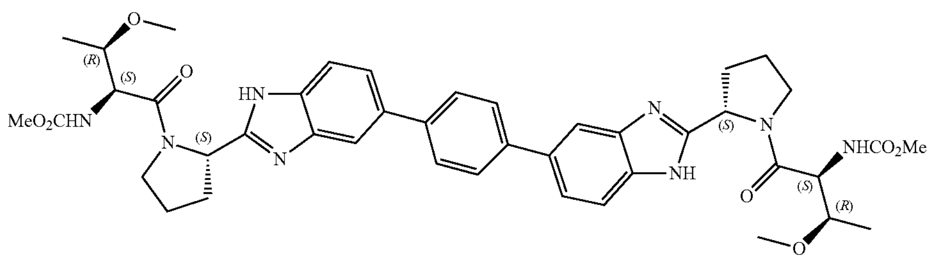 |
| 13 | 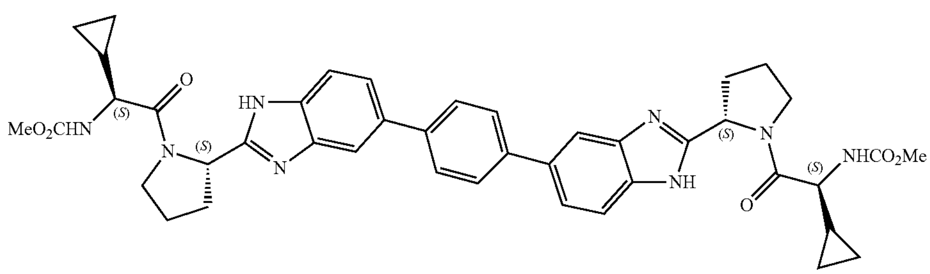 |
| 14 | 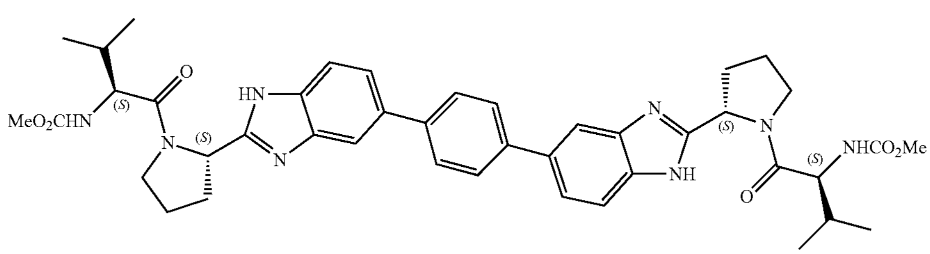 |
| 15 | 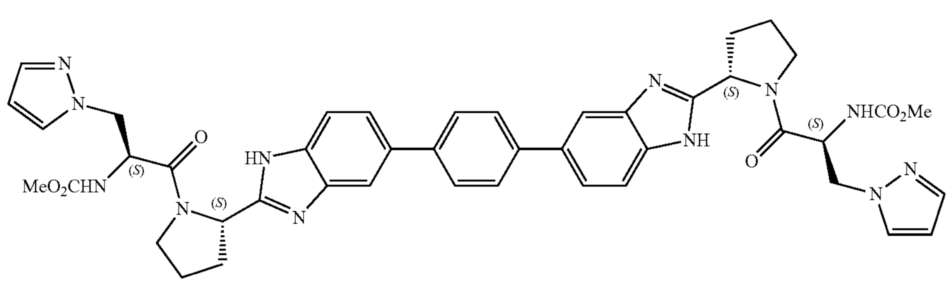 |

TABLE 1-continued
| Compound | Structure |
|---|---|
| 16 | 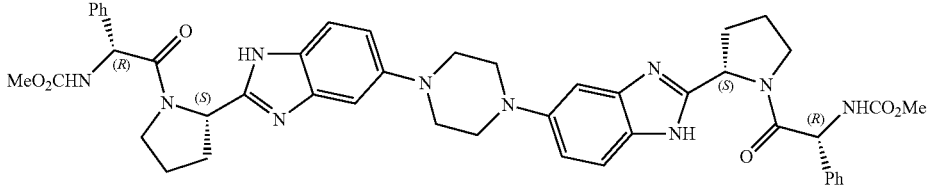 |
| 17 | 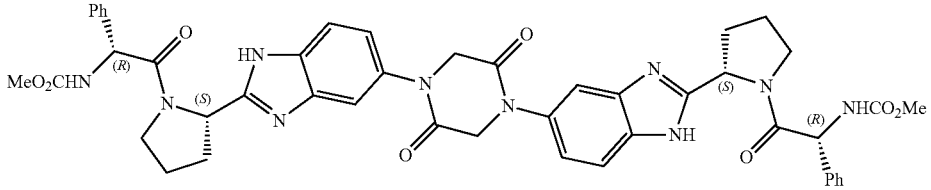 |
| 18 | 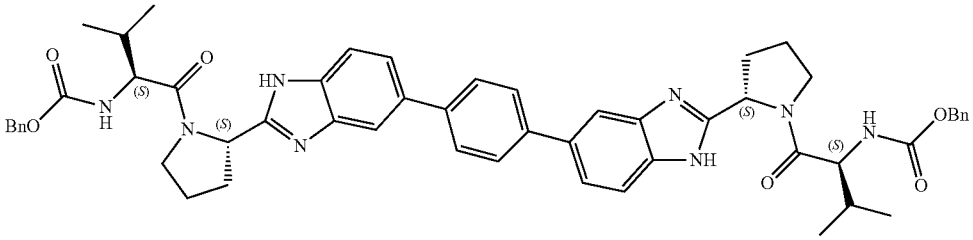 |
| 19 | 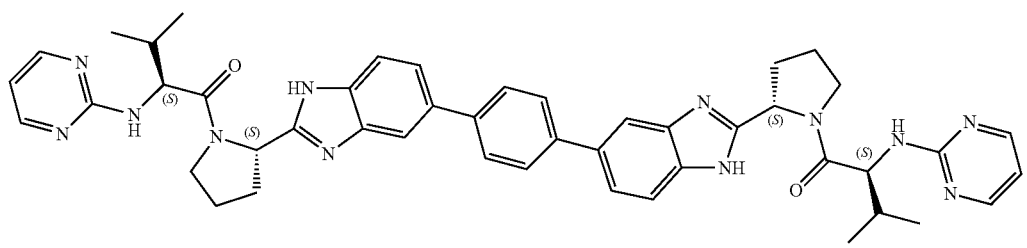 |
| 20 | 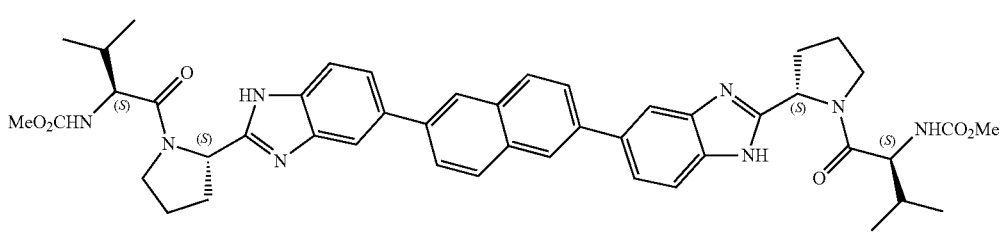 |
| 21 | 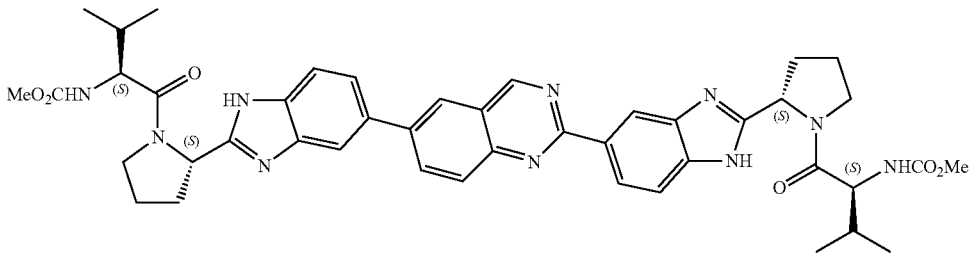 |
| 22 | 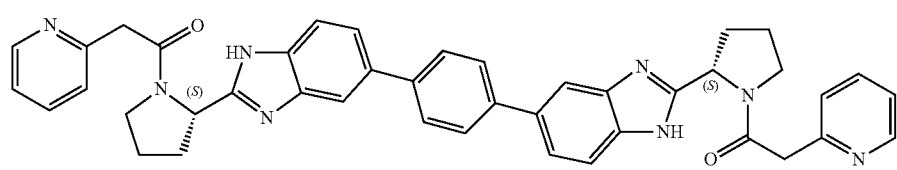 |

TABLE 1-continued

| Compound | Structure |
|---|---|
| 23 | 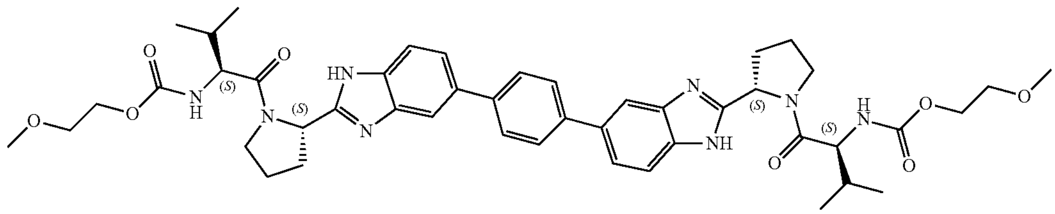 |
| 24 | 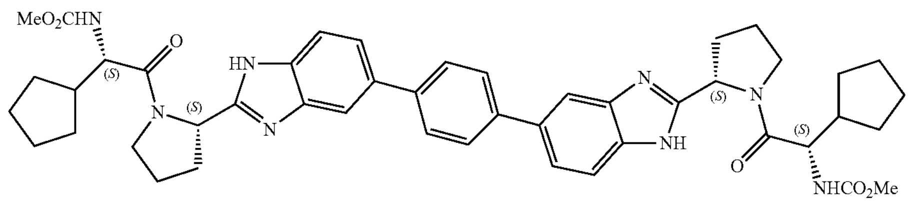 |
| 25 | 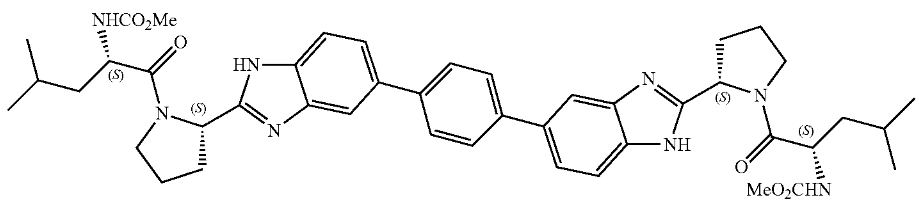 |
| 26 | 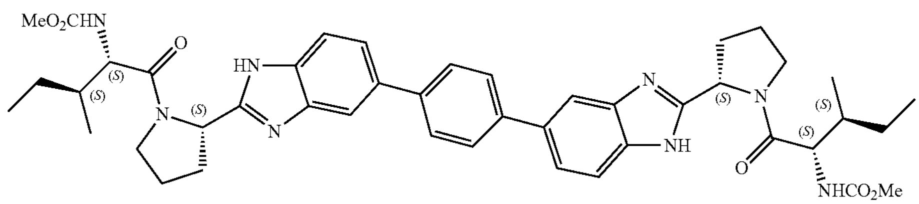 |
| 27 | 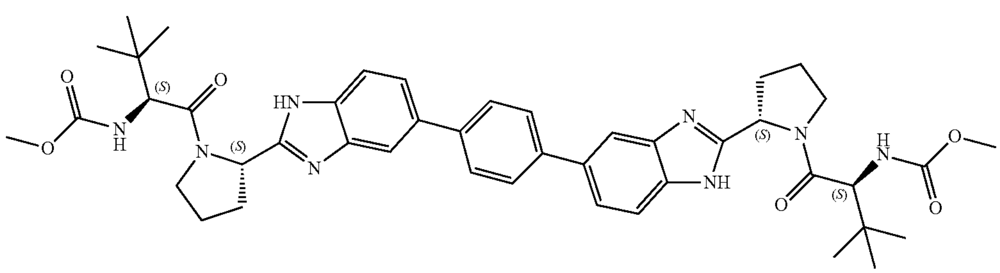 |
| 28 | 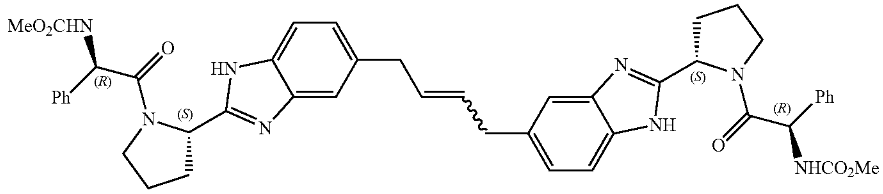 |
| 29 | 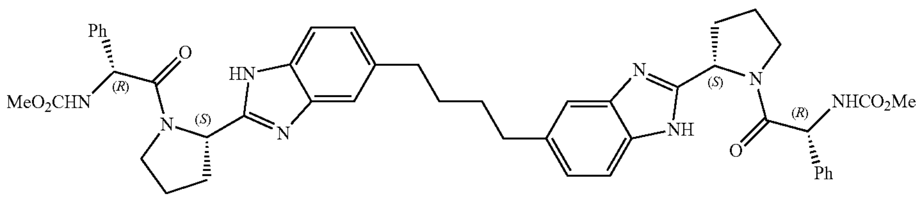 |

TABLE 1-continued

| Compound | Structure |
| --- | --- |
| 30 | 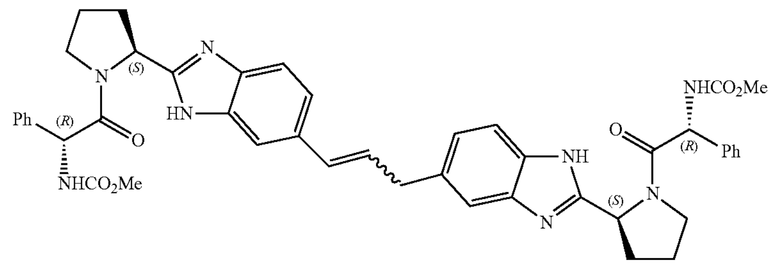 |
| 31 | 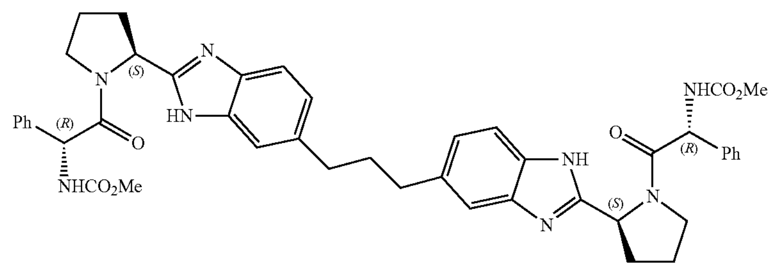 |
| 32 | 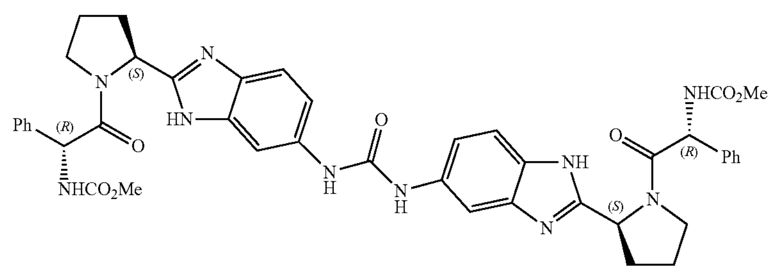 |
| 33 | 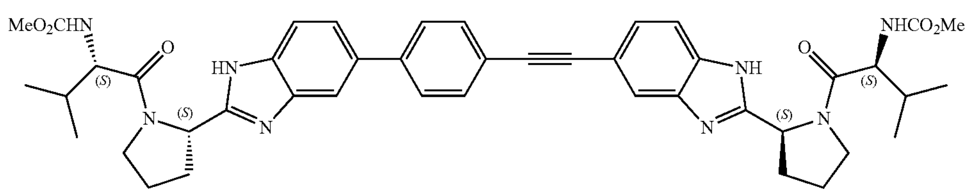 |
| 34 | 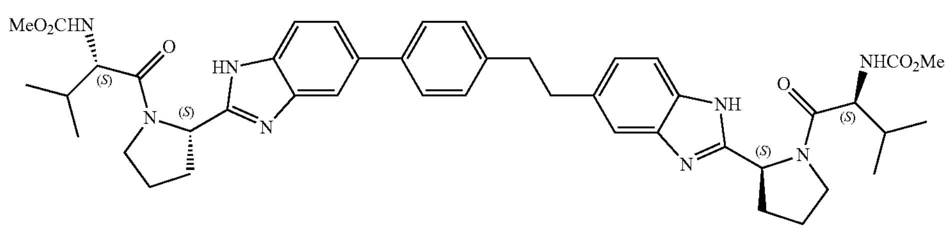 |
| 35 | 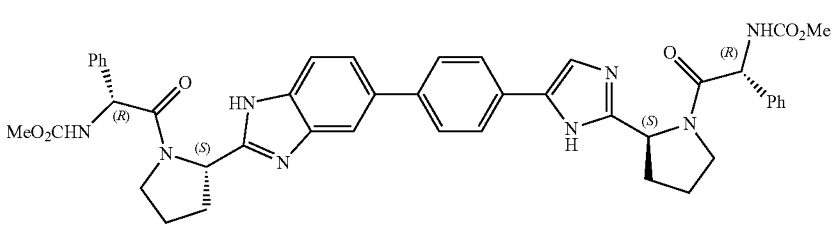 |

TABLE 1-continued

| Compound | Structure |
|---|---|
| 36 | 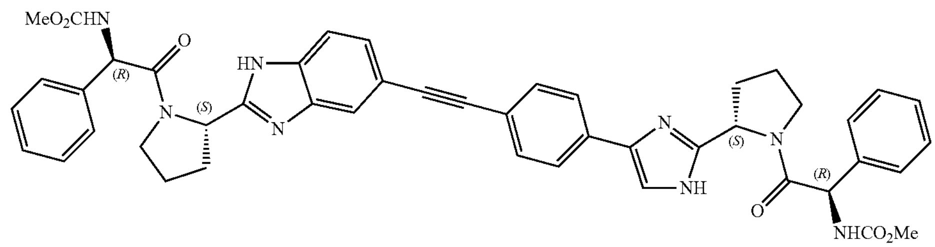 |
| 37 | 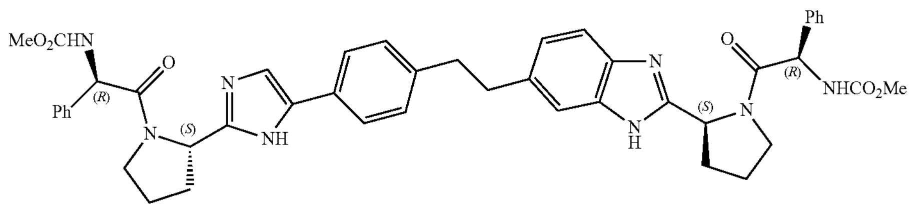 |
| 38 | 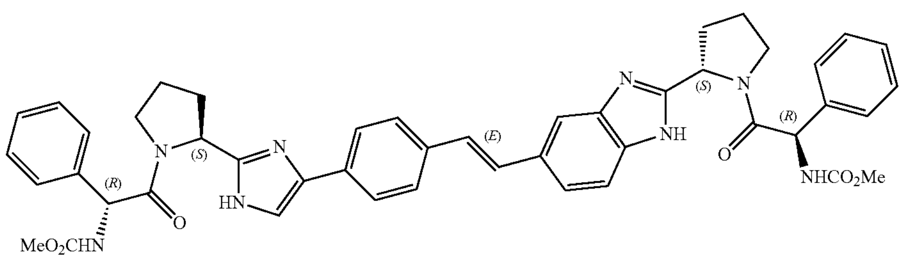 |
| 39 | 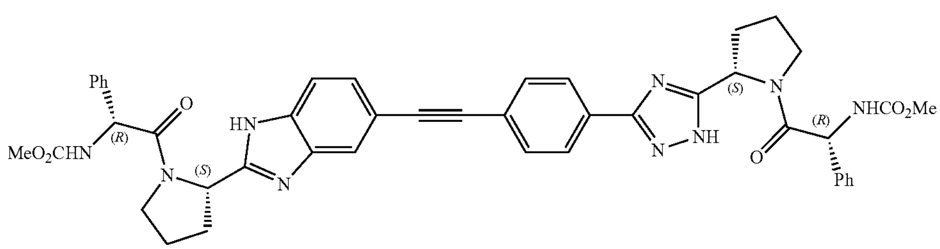 |
| 40 | 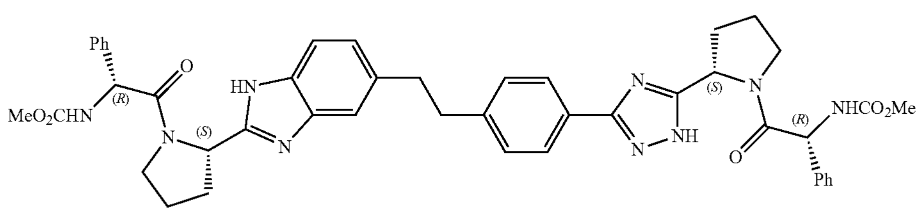 |
| 41 | 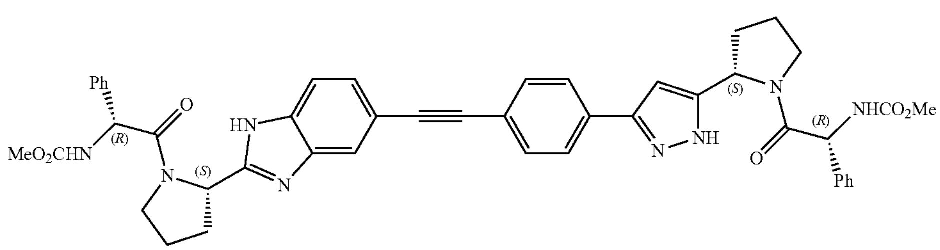 |

| Compound | Structure |
|---|---|
| 42 | 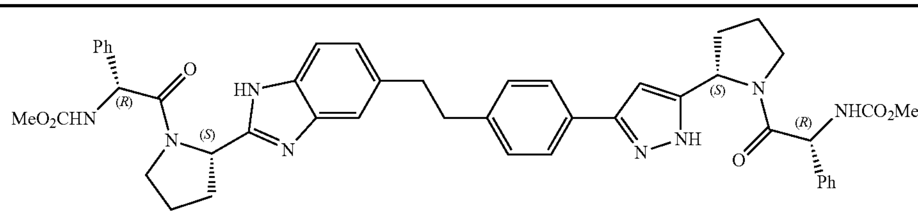 |
| 43 | 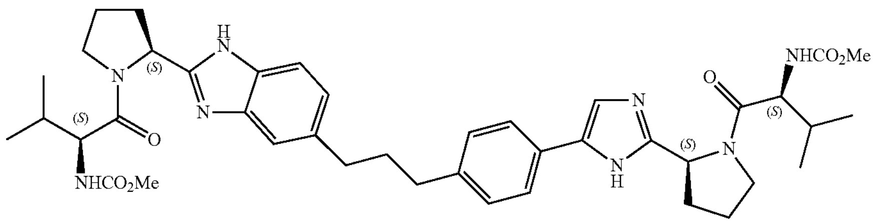 |
| 44 | 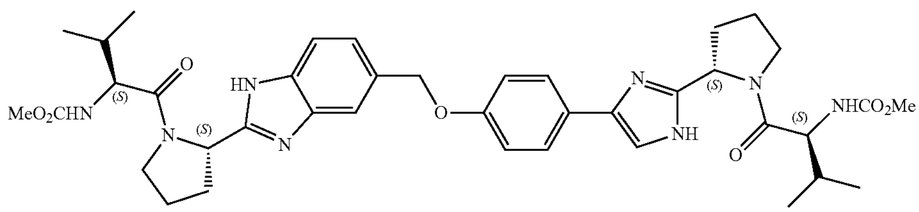 |
| 45 | 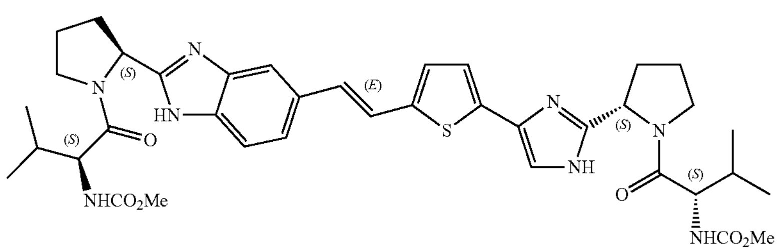 |
| 46 | 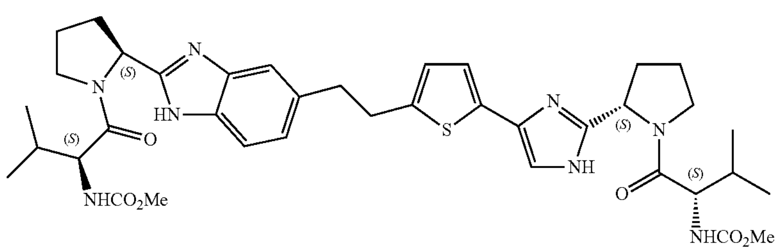 |
| 47 | 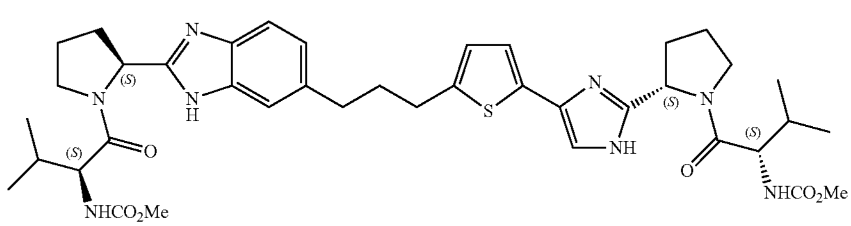 |
| 48 | 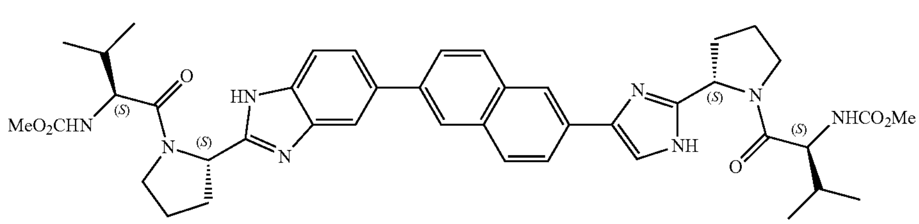 |

TABLE 1-continued

TABLE 1-continued

| Compound | Structure |
|---|---|
| 49 | 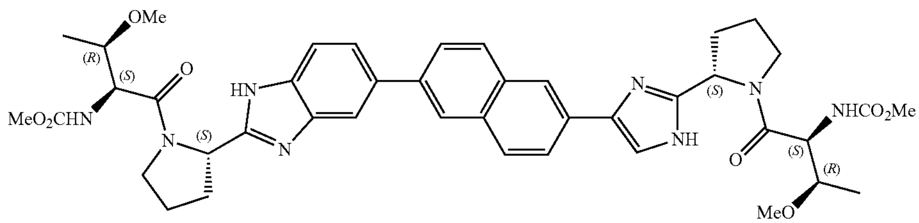 |
| 50 | 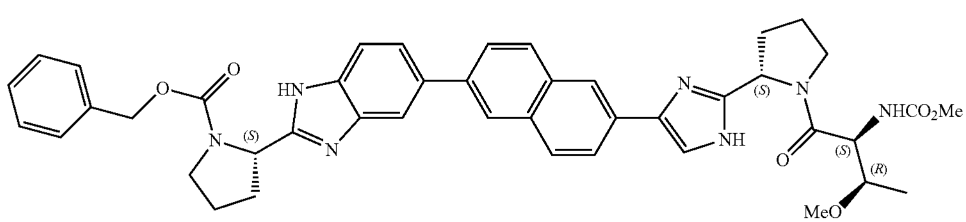 |
| 51 | 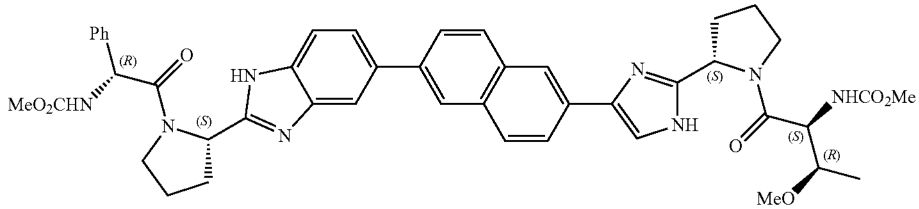 |
| 52 | 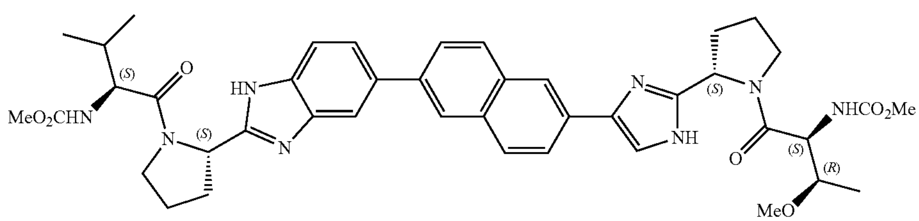 |
| 53 | 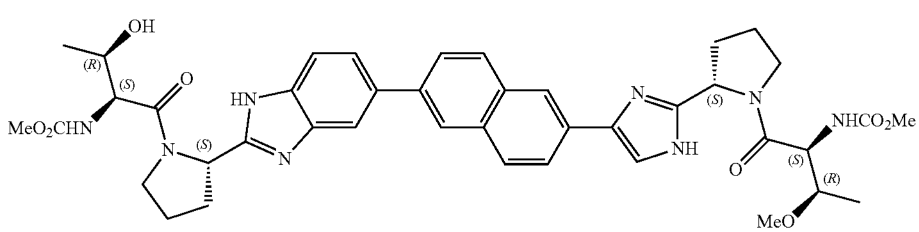 |
| 54 | 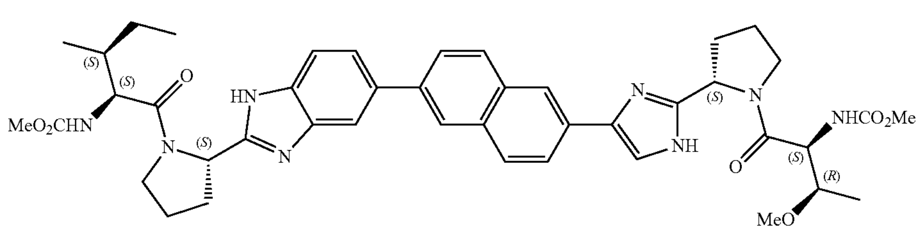 |

TABLE 1-continued

| Compound | Structure |
|---|---|
| 55 | 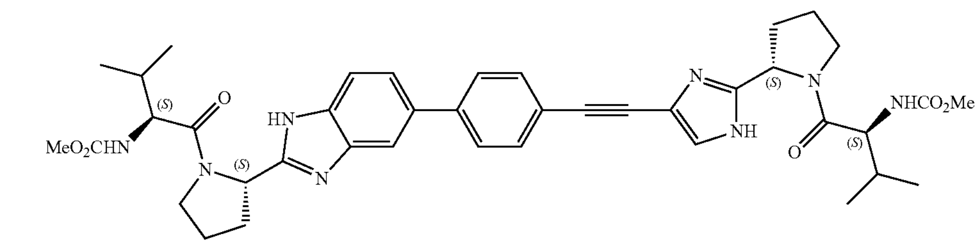 |
| 56 | 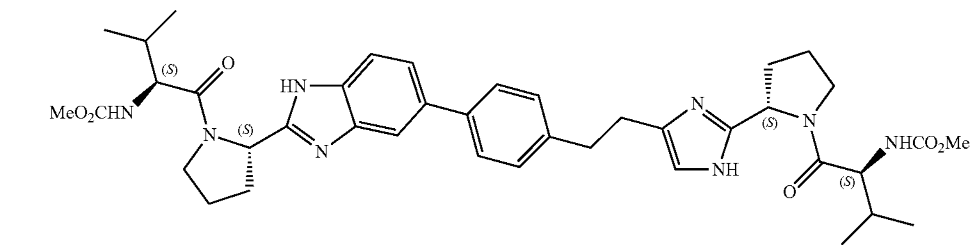 |
| 57 | 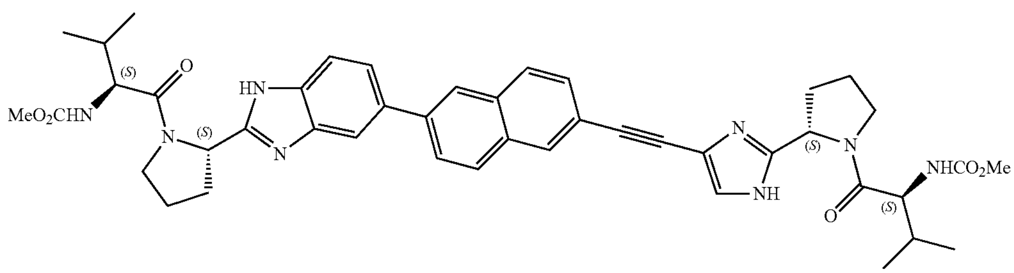 |
| 58 | 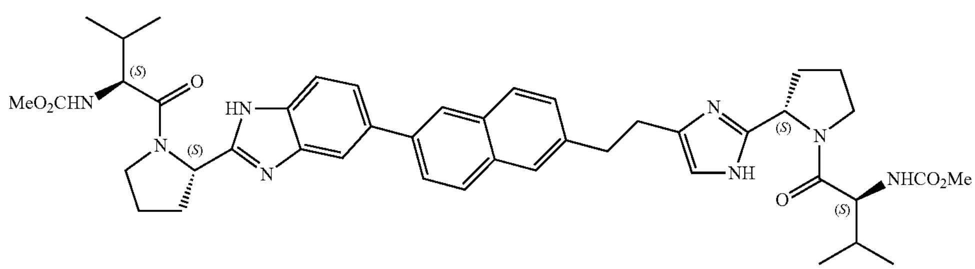 |
| 59 | 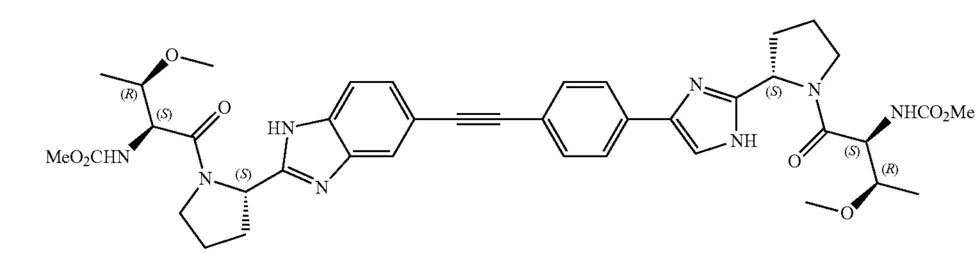 |
| 60 | 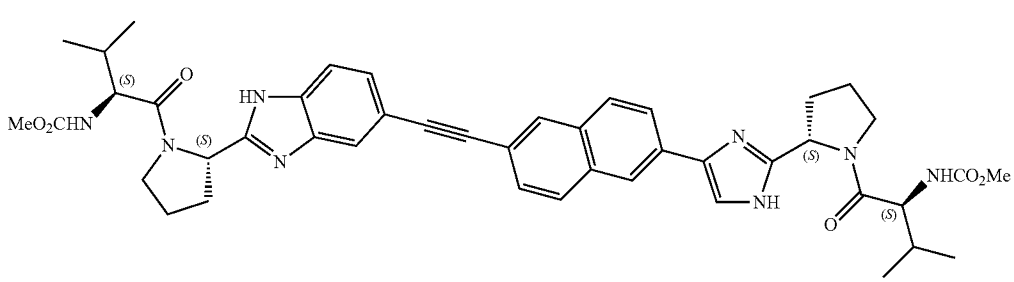 |

TABLE 1-continued

| Compound | Structure |
|---|---|
| 61 | 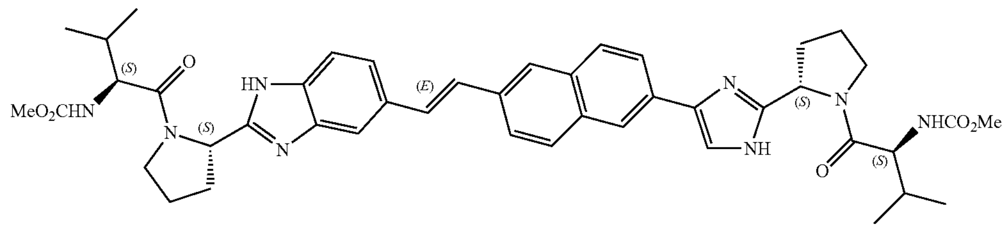 |
| 62 | 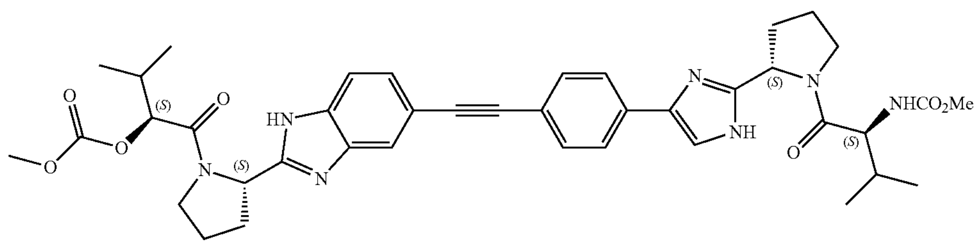 |
| 63 | 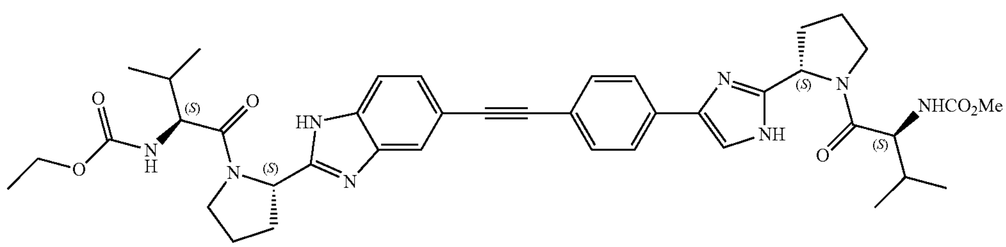 |
| 64 | 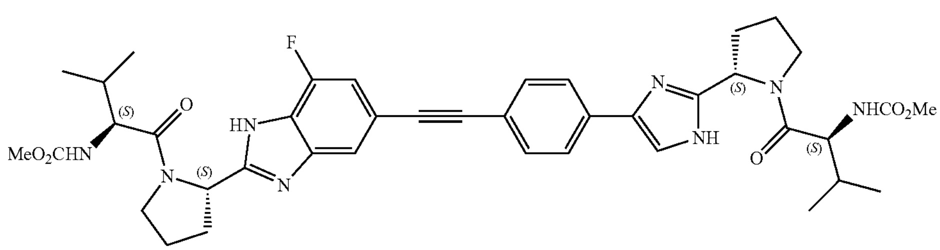 |
| 65 | 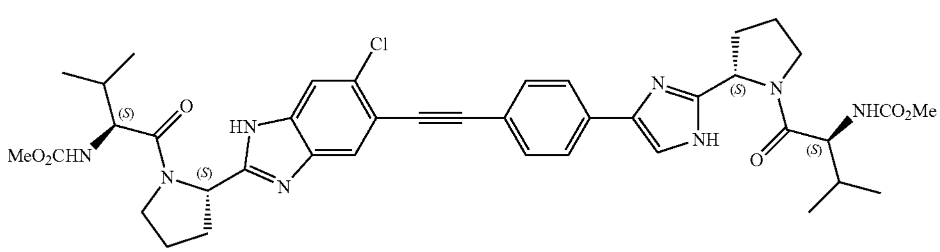 |
| 66 | 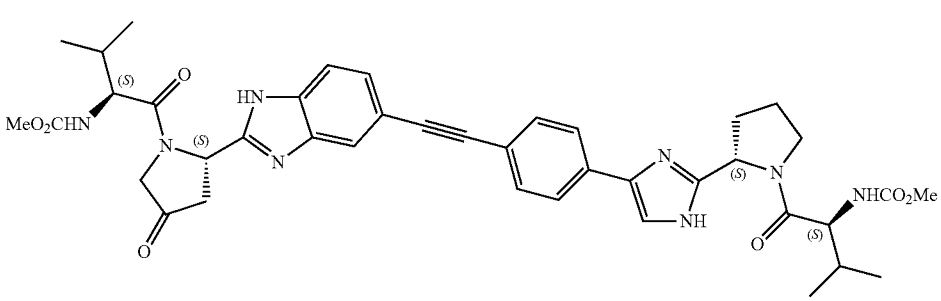 |

TABLE 1-continued

| Compound | Structure |
|---|---|
| 67 | 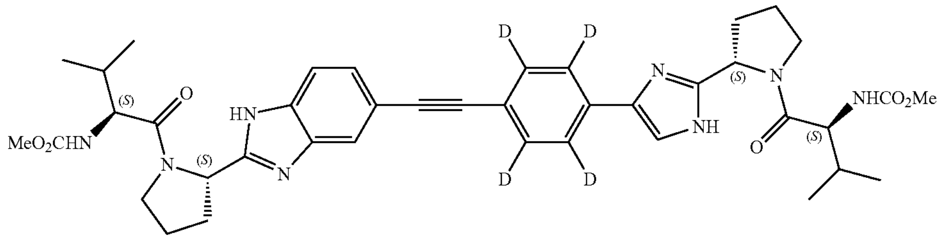 |
| 68 | 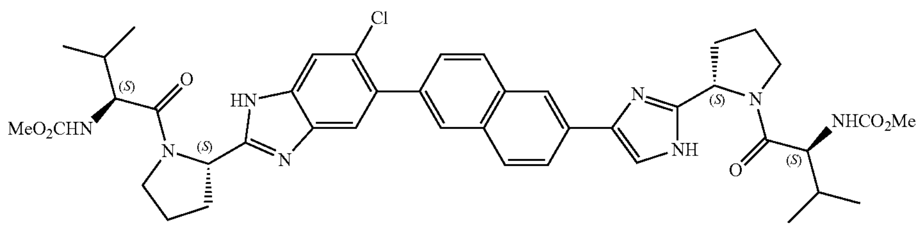 |
| 69 | 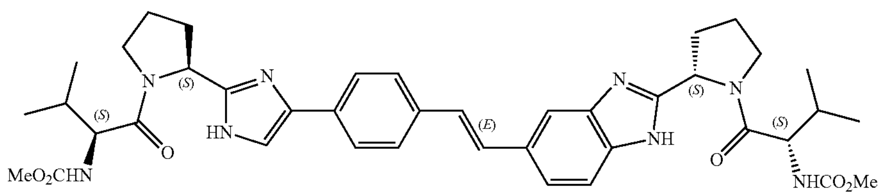 |
| 70 | 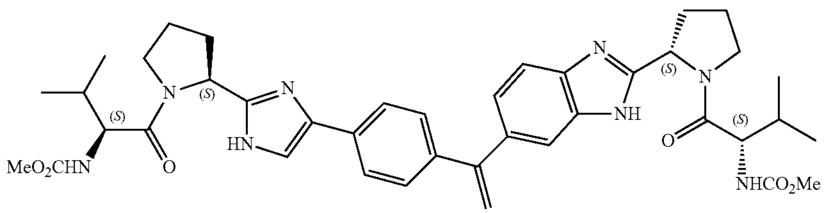 |
| 71 | 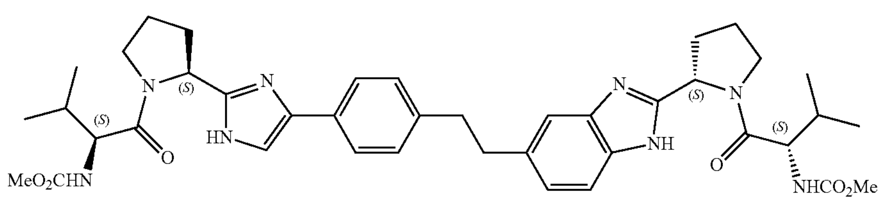 |
| 72 | 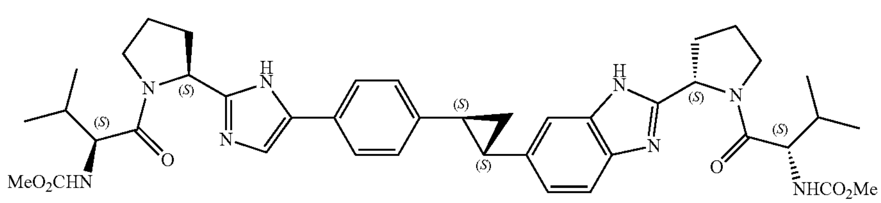 |
| 73 | 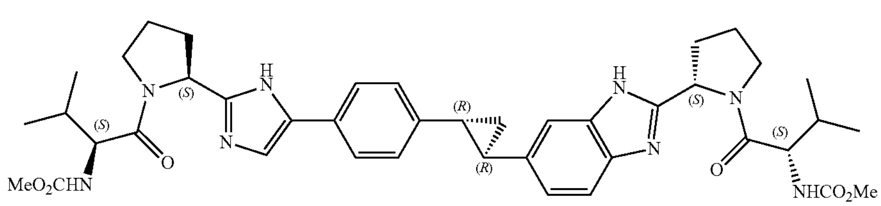 |

TABLE 1-continued

| Compound | Structure |
|---|---|
| 74 | 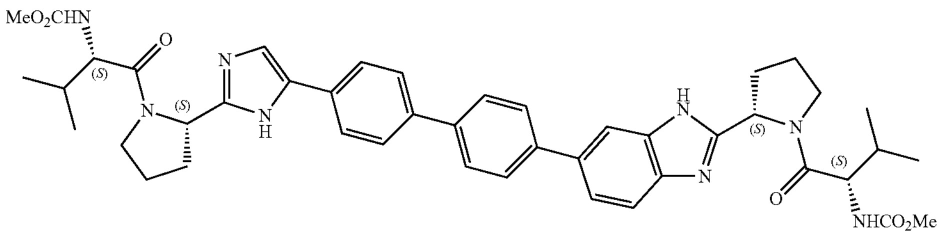 |
| 75 | 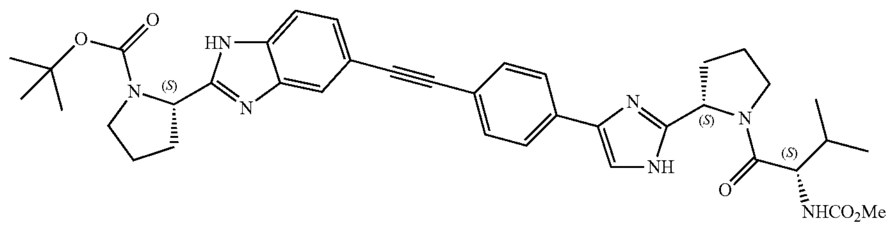 |
| 76 | 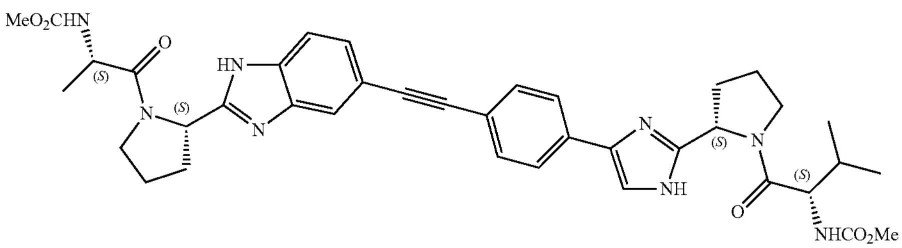 |
| 77 | 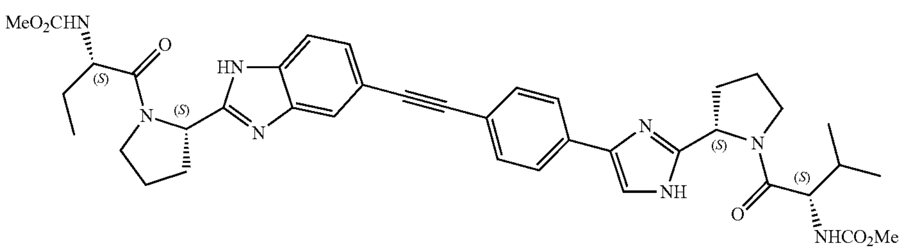 |
| 78 | 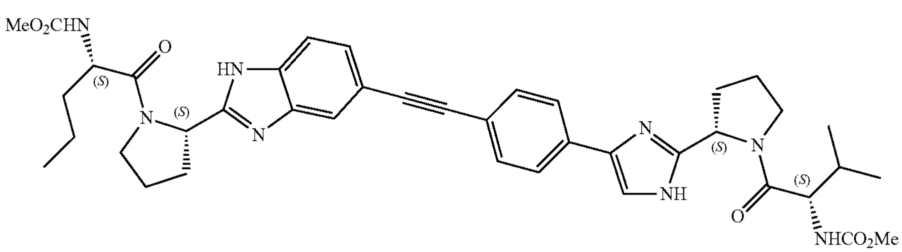 |
| 79 | 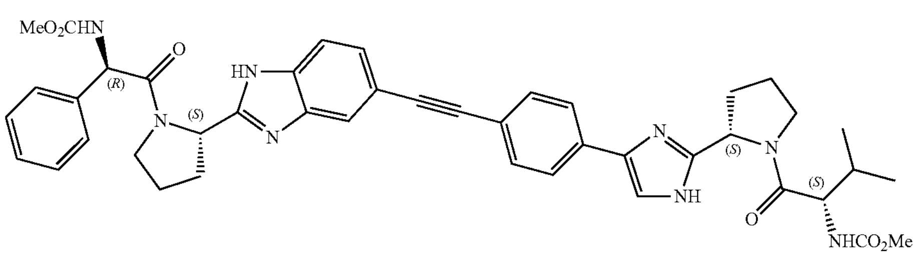 |

TABLE 1-continued

| Compound | Structure |
|---|---|
| 80 | 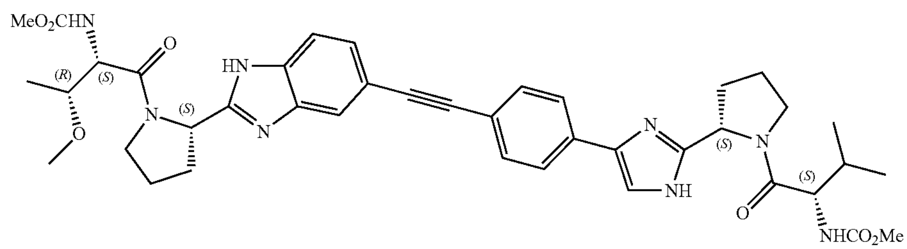 |
| 81 | 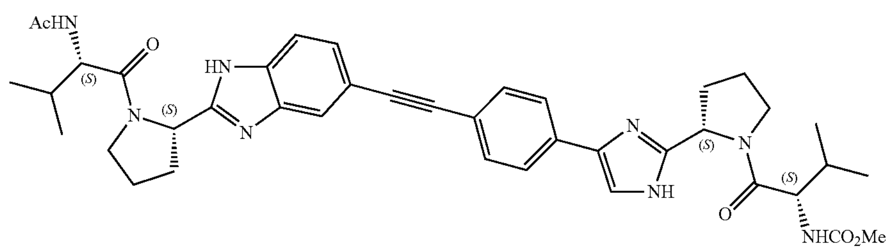 |
| 82 | 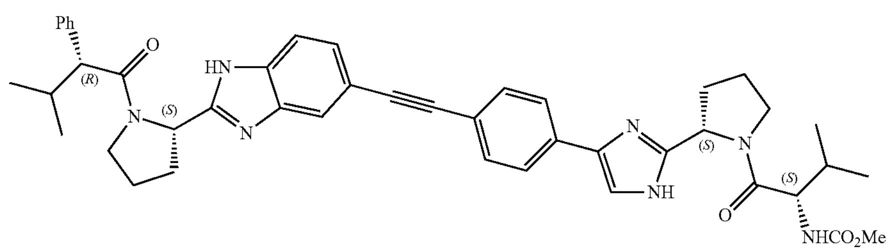 |
| 83 | 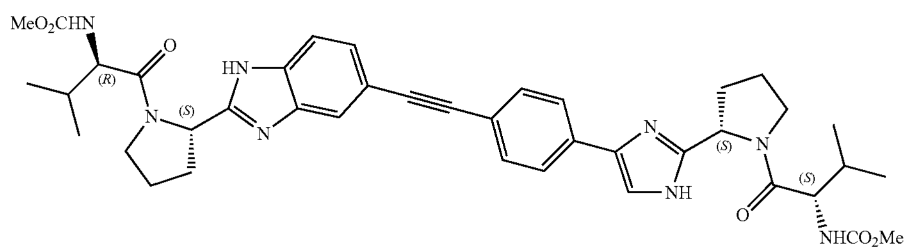 |
| 84 | 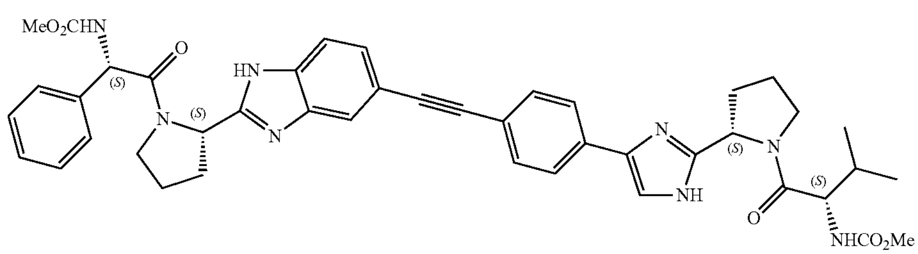 |
| 85 | 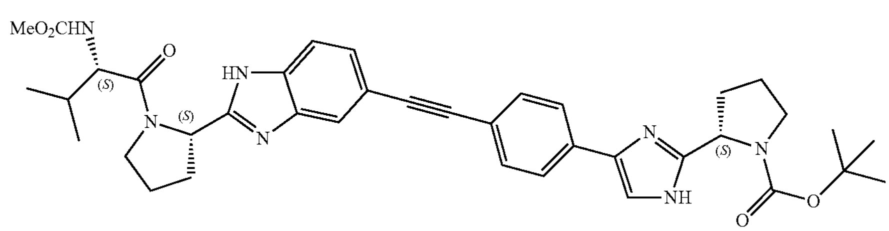 |

TABLE 1-continued

| Compound | Structure |
|---|---|
| 86 | 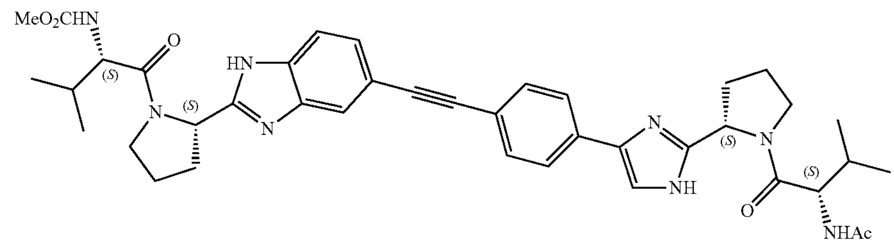 |
| 87 | 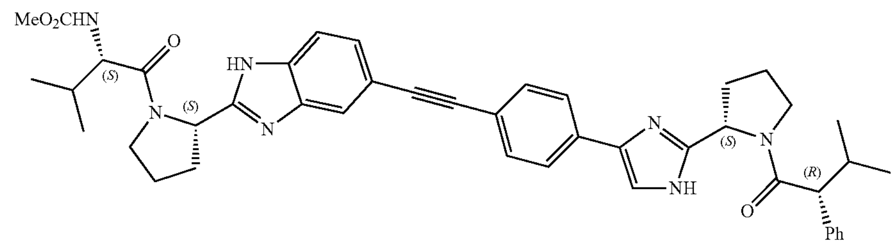 |
| 88 | 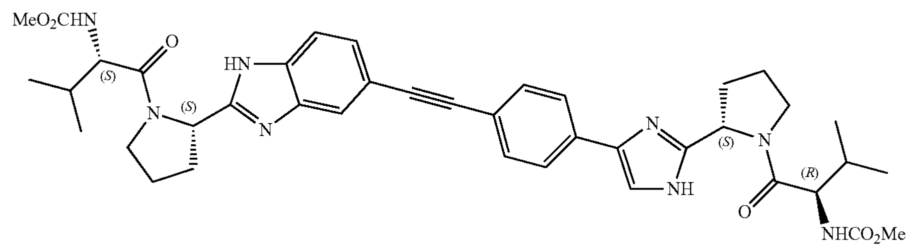 |
| 89 | 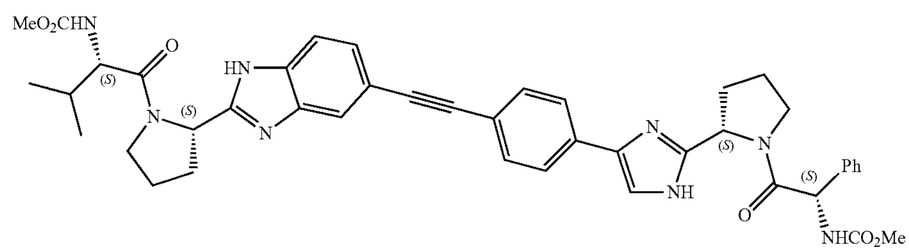 |
| 90 | 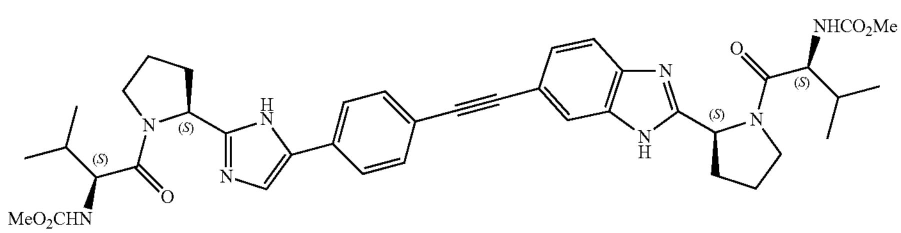 |
| 91 | 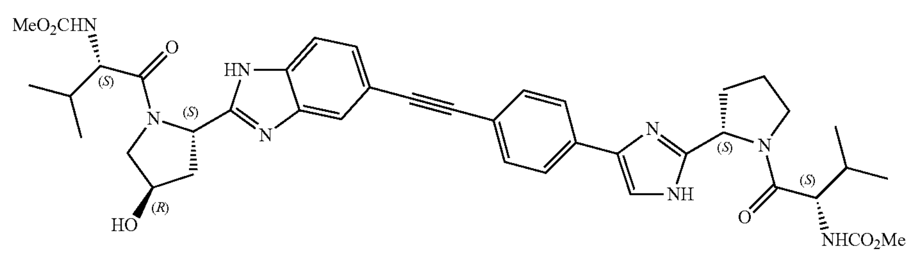 |

TABLE 1-continued

| Compound | Structure |
|---|---|
| 92 | 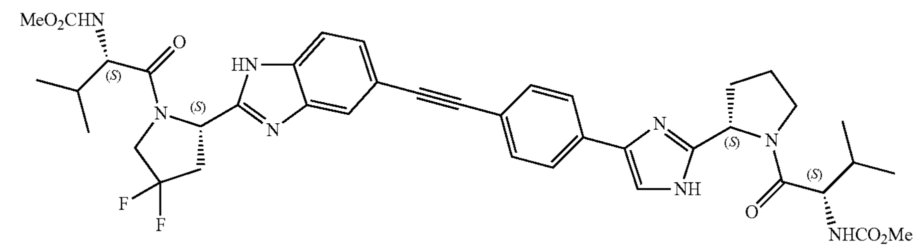 |
| 93 | 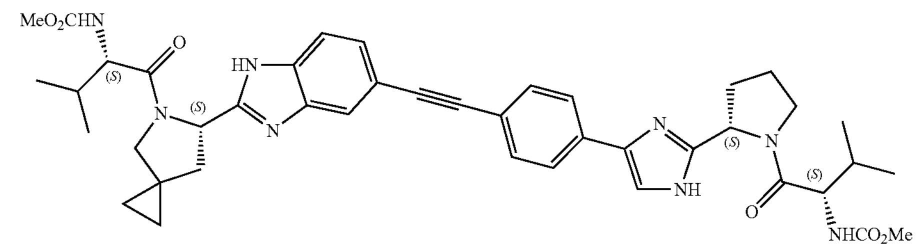 |
| 94 | 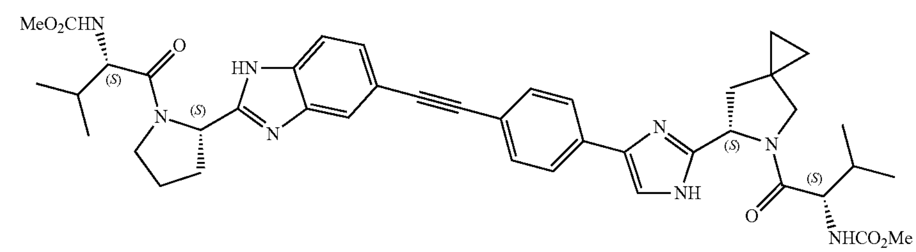 |
| 95 | 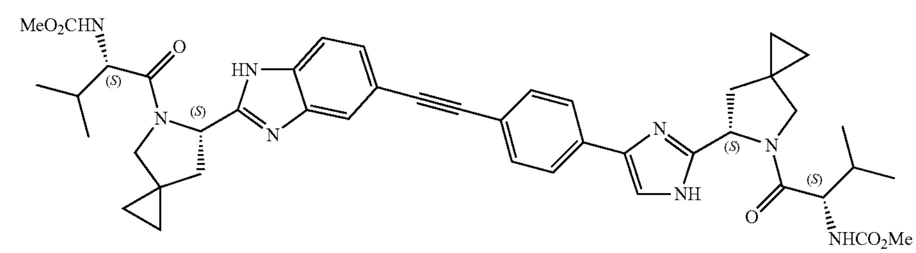 |
| 96 | 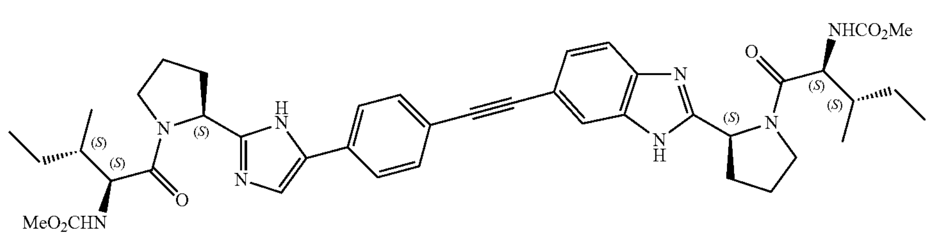 |
| 97 | 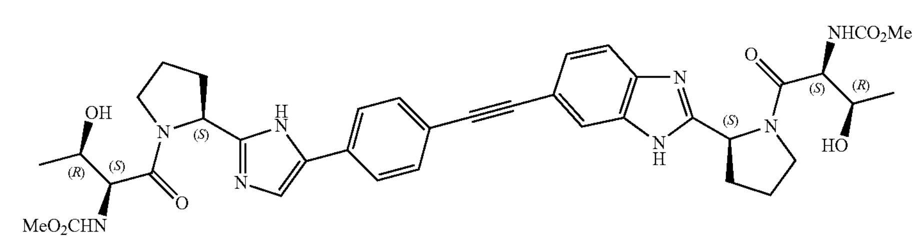 |

TABLE 1-continued

| Compound | Structure |
|---|---|
| 98 | 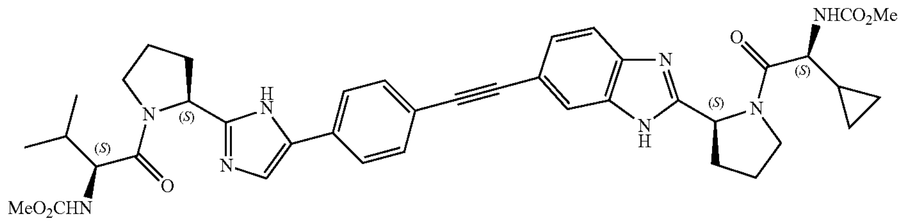 |
| 99 | 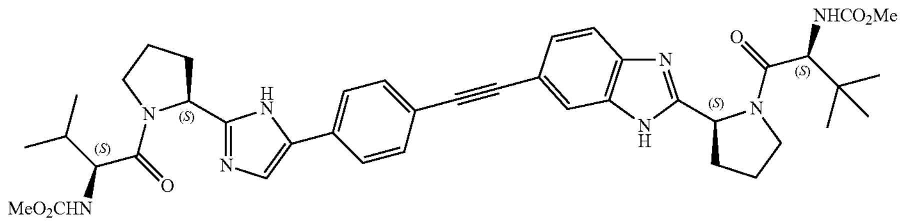 |
| 100 | 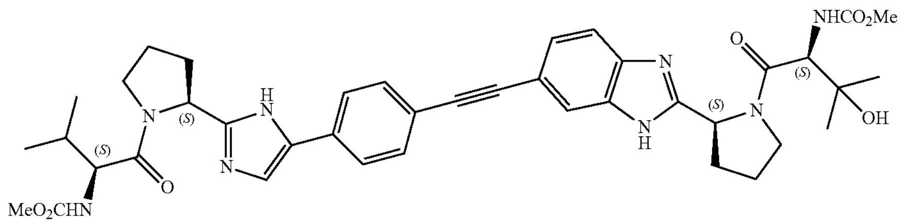 |
| 101 | 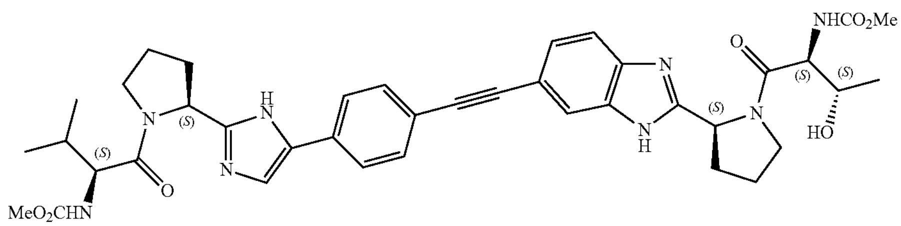 |
| 102 | 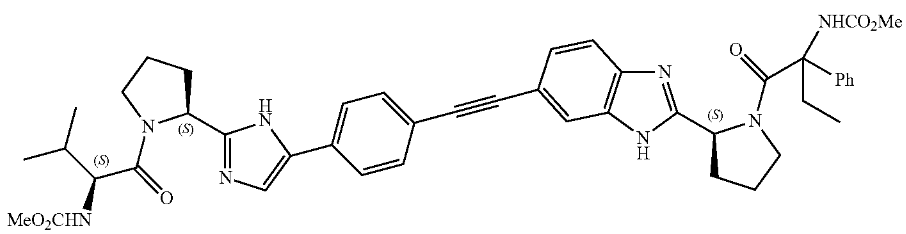 |
| 103 | 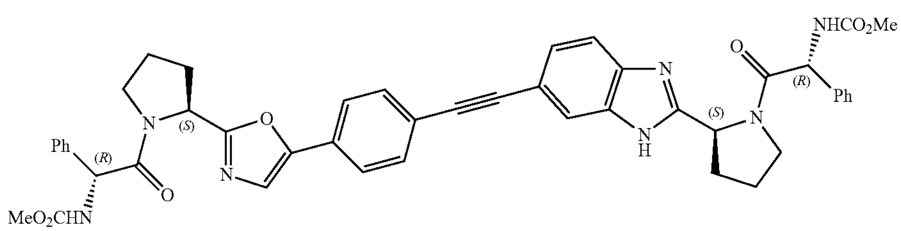 |
| 104 | 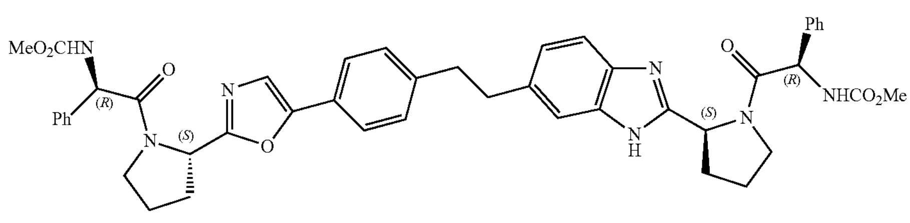 |

TABLE 1-continued

| Compound | Structure |
|---|---|
| 105 | 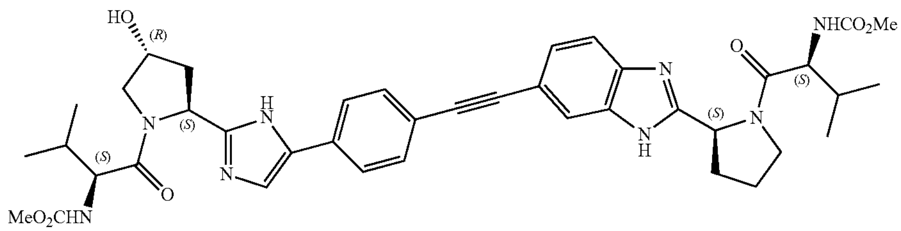 |
| 106 | 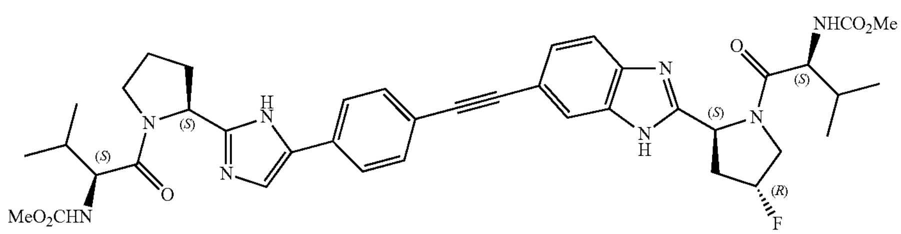 |
| 107 | 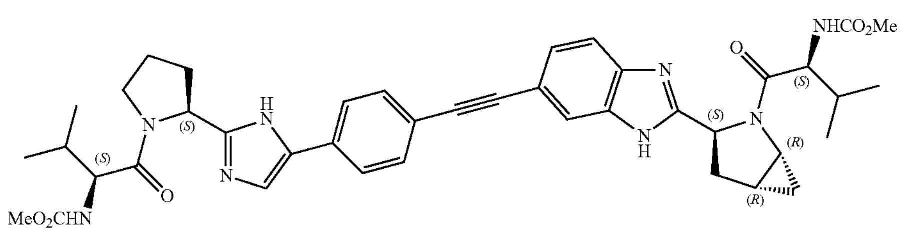 |
| 108 | 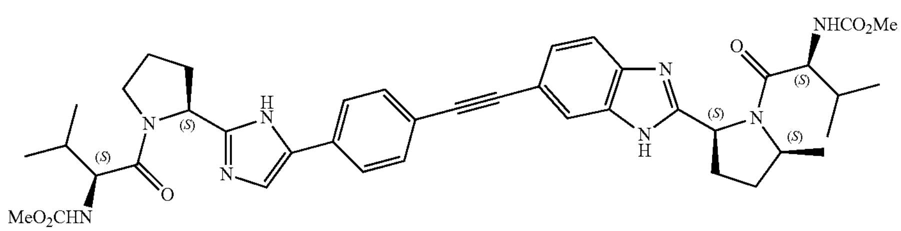 |
| 109 | 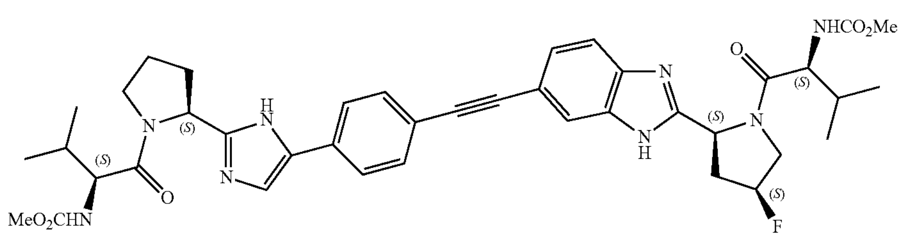 |
| 110 | 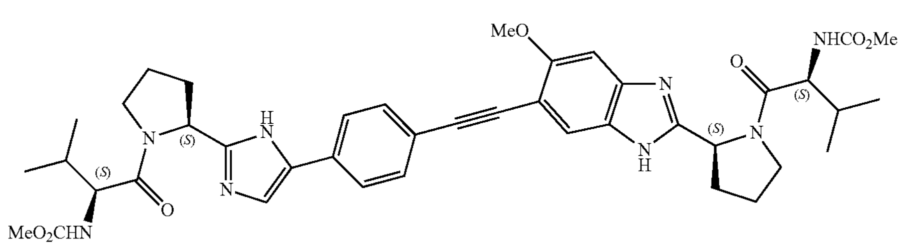 |

TABLE 1-continued

| Compound | Structure |
|---|---|
| 111 | 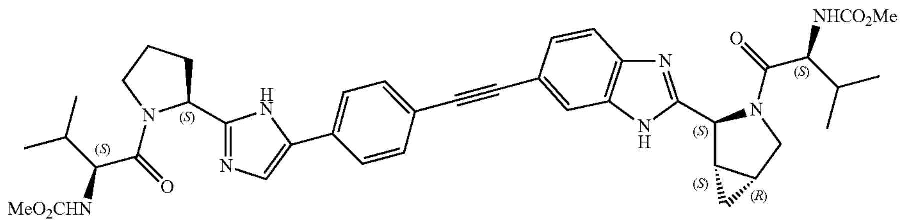 |
| 112 | 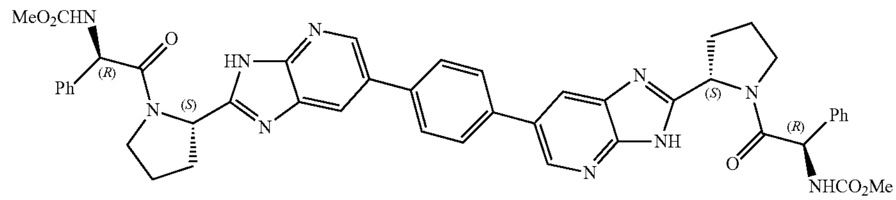 |
| 113 | 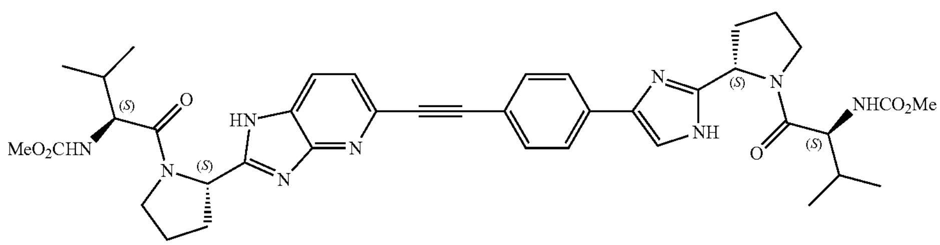 |
| 114 | 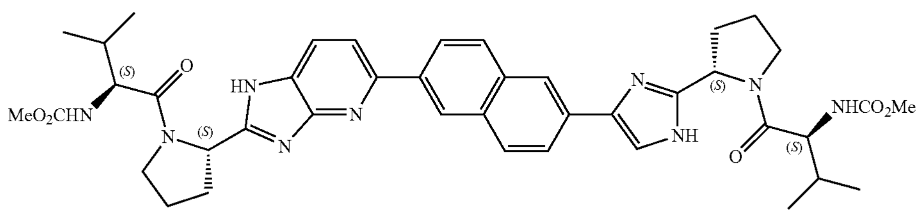 |
| 115 | 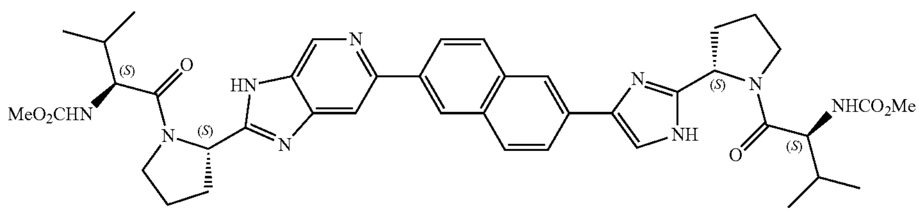 |
| 116 | 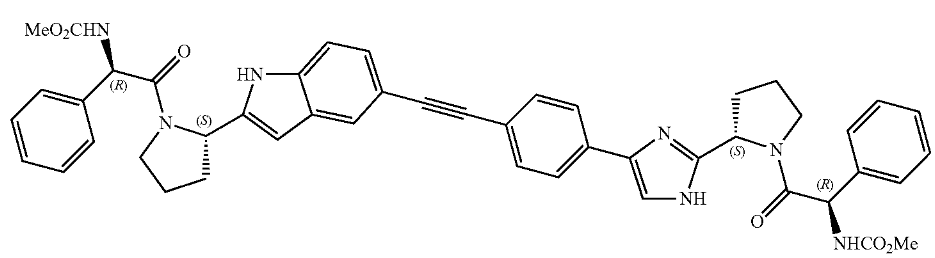 |

TABLE 1-continued

| Compound | Structure |
|---|---|
| 117 | 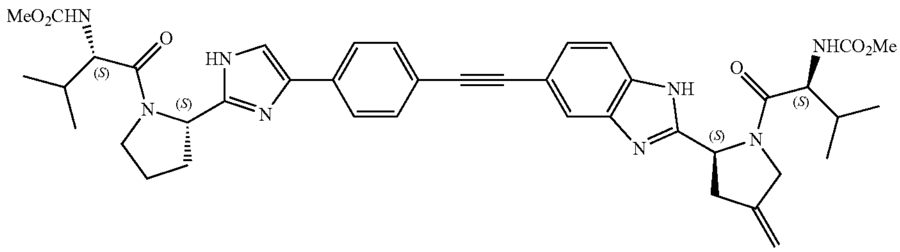 |
| 118 | 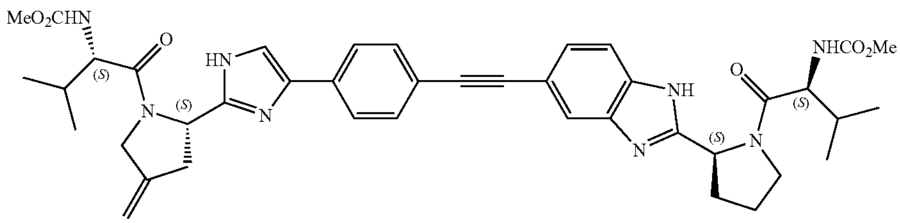 |
| 119 | 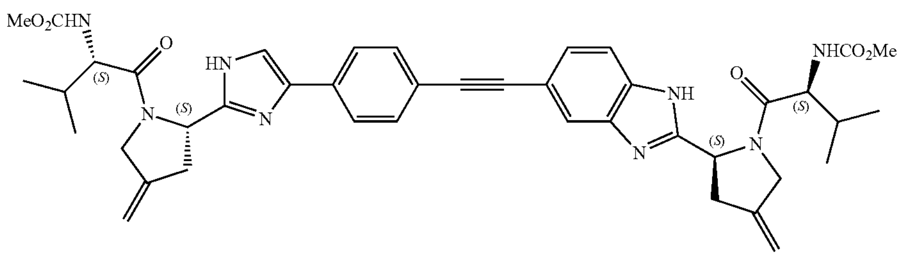 |
| 120 | 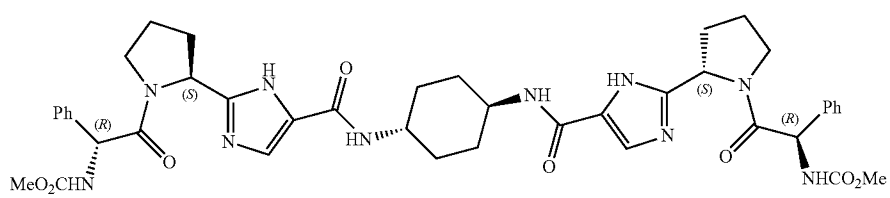 |
| 121 | 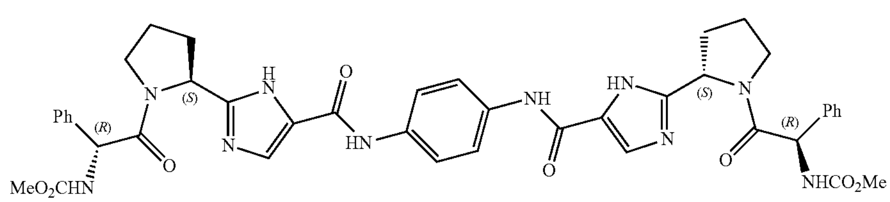 |
| 122 | 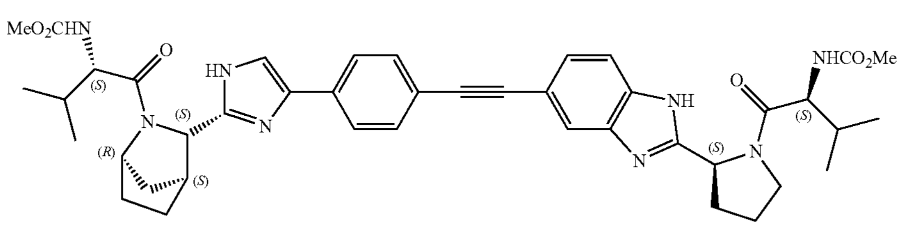 |

TABLE 1-continued

| Compound | Structure |
|---|---|
| 123 | 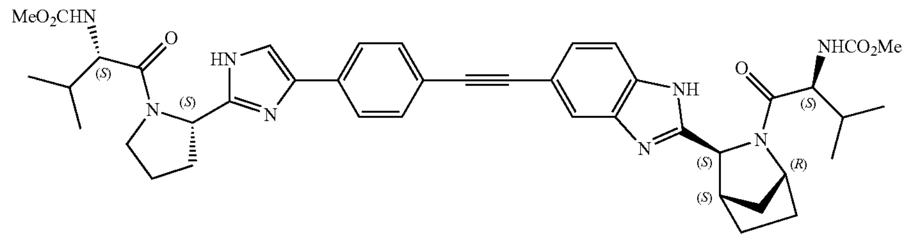 |
| 124 | 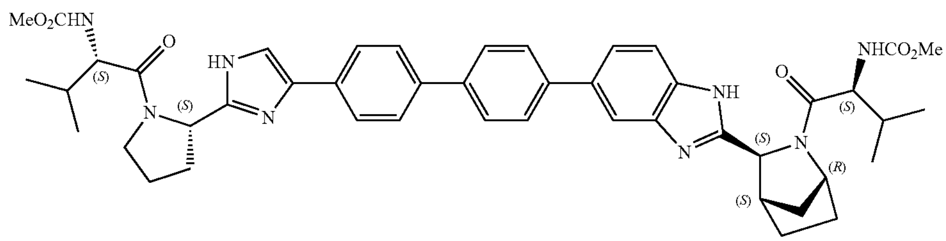 |
| 125 | 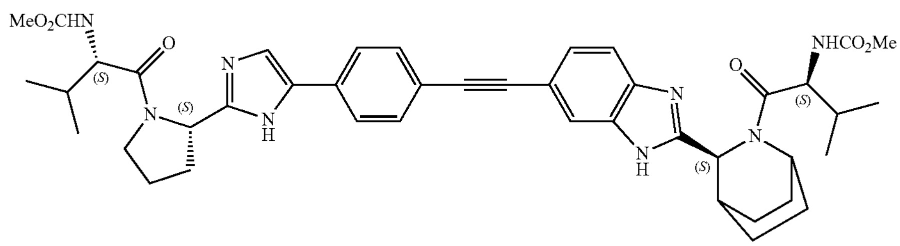 |
| 126 | 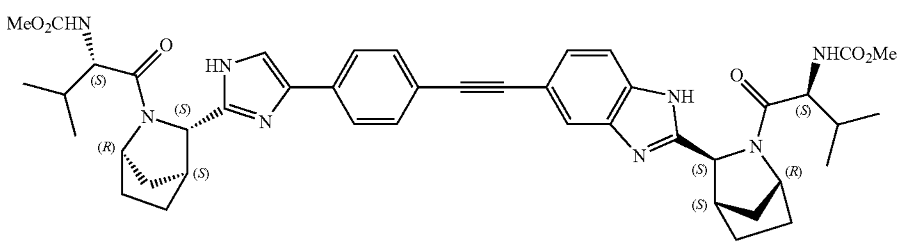 |
| 127 | 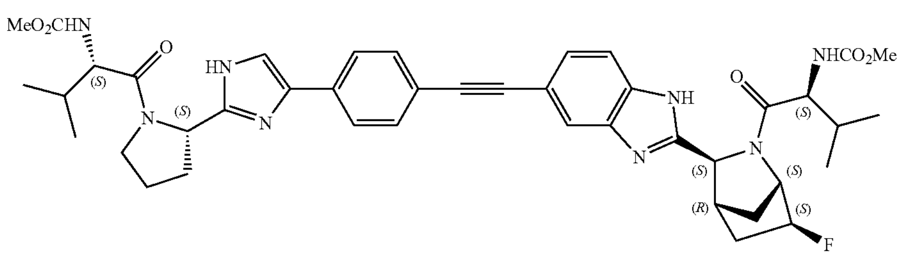 |
| 128 | 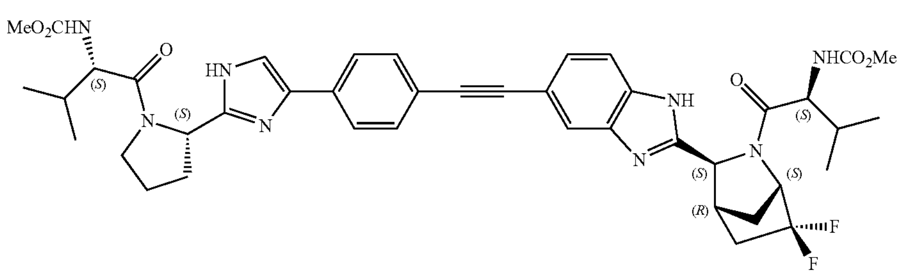 |

TABLE 1-continued

| Compound | Structure |
|---|---|
| 129 | 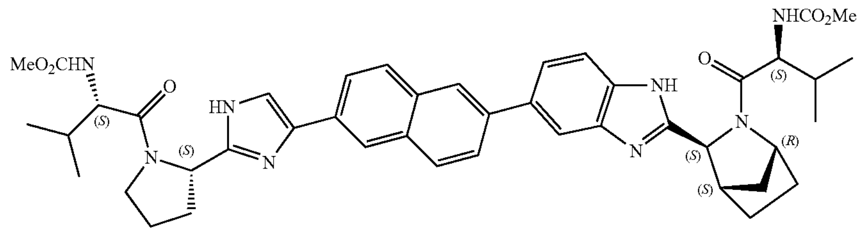 |
| 130 | 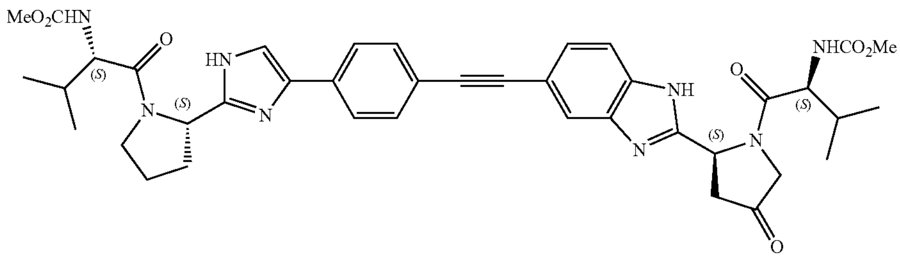 |
| 131 | 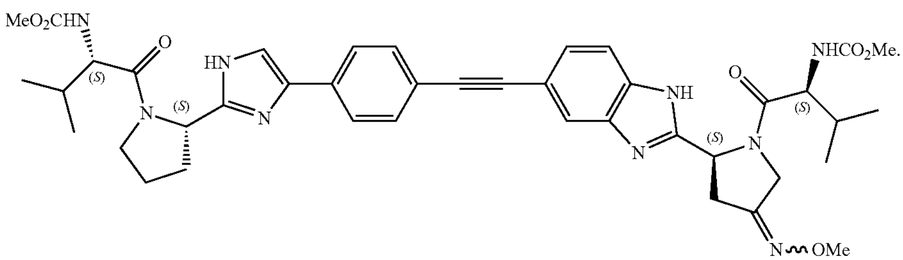 |

It will be appreciated that the description of the present invention herein should be construed in congruity with the laws and principles of chemical bonding. In some instances it may be necessary to remove a hydrogen atom in order to accommodate a substitutent at any given location.

It is intended that the definition of any substituent or variable (e.g., $R^1$, $R^2$, u, m, etc.) at a particular location in a molecule be independent of its definitions elsewhere in that molecule. For example, when u is 2, each of the two $R^1$ groups may be the same or different.

It will be yet appreciated that the compounds of Formula (I) may contain one or more asymmetric carbon atoms and may exist in racemic, diastereoisomeric, and optically active forms. It will still be appreciated that certain compounds of Formula (I) may exist in different tautomeric forms. All tautomers are contemplated to be within the scope of the present invention.

It should be understood that the compounds encompassed by the present invention are those that are suitably stable for use as pharmaceutical agent.

It will be further appreciated that reference herein to therapy and/or treatment includes, but is not limited to, prevention, retardation, prophylaxis, therapy and/or cure of the disease. It will further be appreciated that references herein to treatment or prophylaxis of HCV infection includes treatment or prophylaxis of HCV-associated disease such as liver fibrosis, cirrhosis and hepatocellular carcinoma.

A further embodiment of the present invention includes pharmaceutical compositions comprising a combination of a compound that inhibits the function of the HCV NS5A protein and an additional agent having anti-HCV activity, or a pharmaceutically acceptable salt of any of thereof, with a pharmaceutically acceptable carrier or excipient.

It will be further appreciated that the additional anti-HCV agent compounds can be one or more agents to treat or prevent hepatitis C infections or the symptoms associated with HCV infection. The additional agent can, for example, suppress HCV viral replication by direct or indirect mechanisms. Such agents include, but are not limited to, host immune modulators (for example, interferon-alpha, pegylated interferon-alpha, consensus interferon, interferon-beta, interferon-gamma, CpG oligonucleo-tides and the like); antiviral compounds that inhibit host cellular functions such as inosine monophosphate dehydrogenase (for example, ribavirin and the like); cytokines that modulate immune function (for example, interleukin 2, interleukin 6, and interleukin 12); a compound that enhances the development of type 1 helper T cell response; interfering RNA; anti-sense RNA; vaccines comprising HCV antigens or antigen adjuvant combinations directed against HCV; agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like; and any agent or combination of agents that inhibit the replication of HCV by targeting other proteins of the viral genome involved in the viral replication and/or interfere with the function of other viral targets, such as inhibitors of NS3/NS4A protease, NS3 helicase, NS5B polymerase, NS4A protein and NS5A protein.

According to yet another embodiment, the additional agent that has anti-HCV activity can comprise other inhibitor(s) of targets in the HCV life cycle, including, but not limited to, helicase, polymerase, metalloprotease, NS4A protein, NS5A protein, and internal ribosome entry site (IRES).

Accordingly, one embodiment of the present invention is directed to a method for treating or preventing an infection caused by an RNA-containing virus comprising co-administering to a patient in need of such treatment a therapeutically effective amount of a compound that inhibits the function of the HCV NS5A protein, for example, a compound of Formula (I), and an additional agent that has anti-HCV activity. In some aspects, the agent that has anti-HCV activity is selected from the group consisting of a host immune modulator, an antiviral compound that inhibits host cellular functions, a cytokine that modulates immune function, a compound that enhances the development of type 1 helper T cell response, interfering RNA, anti-sense RNA, a vaccine, an agent that interacts with a host cellular components to block viral protein synthesis or to block viral particle maturation and release with agents targeted toward the viroporin family of membrane proteins and inhibitor(s) of targets in the HCV life cycle. A non-limiting example of the RNA-containing virus is hepatitis C virus (HCV).

A further embodiment of the present invention is directed to a method of treating or preventing infection caused by an RNA-containing virus comprising co-administering to a patient in need of such treatment a therapeutically effective amount of a first compound that inhibits the function of the HCV NS5A protein, for example, compounds of Formula (I), and an additional agent that treats or alleviates symptoms of HCV infection including cirrhosis and inflammation of the liver. In some aspects of the invention, the compound that inhibits the function of HCV NS5A protein is a compound of Formula (I) or a pharmaceutically acceptable salt thereof. A non-limiting example of the RNA-containing virus is hepatitis C virus (HCV).

Yet another embodiment of the present invention provides a method of treating or preventing infection caused by an RNA-containing virus comprising co-administering to a patient in need of such treatment a compound that inhibits the function of HCV NS5A protein and an agent that treats patients for disease caused by hepatitis B (HBV) infection. The inventive method also encompasses co-administering to a patient in need of such treatment a compound that inhibits the function of HCV NS5A protein, an agent that treats patients for disease caused by hepatitis B (HBV) infection and an anti-HCV agent. The invention is also directed to pharmaceutical compositions comprising a pharmaceutically excipient or carrier, a compound that inhibits the function of HCV NS5A protein, an additional anti-HCV agent and an agent that treats patients for disease caused by hepatitis B (HBV) infection. In some aspects, the compound that inhibits the function of HCV NS5A protein is a compound of Formula (I) or a pharmaceutically acceptable salt thereof. An agent that treats patients for disease caused by hepatitis B (HBV) infection may be for example, but not limited thereto, L-deoxythymidine, adefovir, lamivudine or tenfovir, or any combination thereof. A non-limiting example of the RNA-containing virus is hepatitis C virus (HCV).

A further embodiment of the present invention provides a method of treating or preventing infection caused by an RNA-containing virus comprising co-administering to a patient in need of such treatment a compound that inhibits the function of HCV NS5A protein and an agent that treat patients for disease caused by human immunodeficiency virus (HIV) infection. The inventive method also encompasses co-administering to a patient in need of such treatment a compound that inhibits the function of HCV NS5A protein, an agent that treat patients for disease caused by human immunodeficiency virus (HIV) infection and an additional anti-HCV agent. The invention is also directed to pharmaceutical compositions comprising a pharmaceutically acceptable excipient or carrier, a compound that inhibits the function of HCV NS5A protein, an additional anti-HCV agent and an agent that treats patients for disease caused by HIV infection. In some aspects, the compound that inhibits the function of HCV NS5A protein is a compound of Formula (I) or a pharmaceutically acceptable salt thereof. The agent that treats patients for disease caused by human immunodeficiency virus (HIV) infection may include, but is not limited thereto, ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) or T-1249, or any combination thereof. A non-limiting example of the RNA-containing virus is hepatitis C virus (HCV).

It can occur that a patient may be co-infected with hepatitis C virus and one or more other viruses, including, but not limited to, human immunodeficiency virus (HIV), hepatitis A virus (HAV) and hepatitis B virus (HBV). Thus, also contemplated herein is combination therapy to treat such co-infections by co-administering a compound that inhibits the function of HCV NS5A protein, and an additional agent selected from at least an HIV inhibitor, an HAV inhibitor and an HBV inhibitor, or a combination of an HIV inhibitor, an HAV inhibitor and an HBV inhibitor; and optionally additionally administering an additional anti-HCV agent. In addition, the invention encompasses a pharmaceutical composition comprising a pharmaceutically excipient or carrier, a compound that inhibits the function of HCV NS5A protein, an additional anti-HCV agent and an additional agent selected from at least an HIV inhibitor, an HAV inhibitor and an HBV inhibitor, or a combination of an HIV inhibitor, an HAV inhibitor and an HBV inhibitor.

In addition, the present invention provides the use of a compound that inhibits the function of HCV NS5A protein (for example, a compound of Formula (I) or a pharmaceutically acceptable salt thereof) and an additional agent selected from the group consisting of a host immune modulator and one or more additional antiviral agents, or a combination thereof, to prepare a medicament for the treatment of an infection caused by an RNA-containing virus in a patient, particularly hepatitis C virus. Examples of the host immune modulator include, but are not limited to, interferon-alpha, pegylated-interferon-alpha, interferon-beta, interferon-gamma, a cytokine, a vaccine, and a vaccine comprising an antigen and an adjuvant. Preferably, said additional antiviral agent inhibits replication of HCV either by inhibiting host cellular functions associated with viral replication or by targeting proteins of the viral genome.

When used in the above or other treatments, a compound that inhibits the function of HCV NS5A protein and an additional agent that has anti-viral activity can be employed in pure form or, where such forms exist, as a pharmaceutically acceptable salt thereof. Alternatively, such combination of therapeutic agents can be administered as a pharmaceutical composition containing a therapeutically effective amount of the compound or combination of compounds of interest, or their pharmaceutically acceptable salt thereof, in combination with one or more agents as defined hereinabove, and a pharmaceutically acceptable carrier. Such pharmaceutical compositions can be used for inhibiting the replication of an RNA-containing virus, particularly Hepatitis C virus (HCV), by contacting said virus with said pharmaceutical composition. In addition, such compositions are useful for the treatment or prevention of an infection caused by an RNA-containing virus, particularly Hepatitis C virus (HCV).

Hence, a still further embodiment of the invention is directed to a method of treating or preventing infection caused by an RNA-containing virus, particularly a Hepatitis C virus (HCV), comprising administering to a patient in need of such treatment a pharmaceutical composition comprising a compound or combination of compounds of the invention or a pharmaceutically acceptable salt thereof, and one or more agents as defined hereinabove, with a pharmaceutically acceptable carrier.

As discussed above, the compound that inhibits the function of HCV NS5A protein (for example, a compound of Formula (I)) and an additional agent that has anti-viral activity can be formulated as separate compositions which are given at the same time or within a predetermined period of time, or the therapeutic agents can be given as a single unit dosage form.

As described above, antiviral agents contemplated for use in such combination therapy include agents (compounds or biologicals) include those that are effective to inhibit the formation and/or replication of a virus in a mammal, including but not limited to agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other agents that can be administered in combination with a compound, of Formula (I) and an additional agent that has anti-viral activity are a cytochrome P450 monooxygenase inhibitor (also referred to herein as a CYP inhibitor), which is expected to inhibit metabolism of the compounds of Formula (I). Therefore, the cytochrome P450 monooxygenase inhibitor would be in an amount effective to inhibit metabolism of invention compound of Formula (I). Accordingly, the CYP inhibitor is administered in an amount sufficient to increase the bioavailiablity of a compound of Formula (I) when the bioavailability of said compound is increased in comparison to the bioavailability in the absence of the CYP inhibitor.

In one embodiment, the invention provides methods for improving the pharmacokinetics of a compound of Formula (I) when administered in combination with an anti-viral agent or combination of anti-viral agents. The advantages of improving the pharmacokinetics of drugs are recognized in the art (see, for example, US Publication No.'s. 2004/0091527; US 2004/0152625; and US 2004/0091527). Accordingly, one embodiment of this invention provides a method comprising administering an inhibitor of CYP3A4 and a compound of Formula (I) and an additional anti-viral agent or combination of anti-viral agents. Another embodiment of this invention provides a method comprising administering a compound of Formula (I) and an inhibitor of isozyme 3A4 ("CYP3A4"), isozyme 2C19 ("CYP2C19"), isozyme 2D6 ("CYP2D6"), isozyme 1A2 ("CYP1A2"), isozyme 2C9 ("CYP2C9"), or isozyme 2E1 ("CYP2E1"). In a preferred embodiment, the CYP inhibitor preferably inhibits CYP3A4. Any CYP inhibitor that improves the pharmacokinetics of the relevant compound of Formula (I) may be used in a method of this invention. These CYP inhibitors include, but are not limited to, ritonavir (see, for example, WO 94/14436), ketoconazole, troleandomycin, 4-methylpyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methylpyrazole, cyclosporin, and clomethiazole.

It will be understood that the administration of the combination of the invention can be by means of a single patient pack, or patient packs of each formulation, containing within a package insert instructing the patient to the correct use of the invention is a desirable additional feature of this invention.

According to a further aspect of the invention is a pack comprising at least a compound of Formula (I), an anti-viral agent and a CYP inhibitor and an information insert containing directions on the use of the combination of the invention. The anti-viral agent or agents may be provided in the same pack or in separate packs.

Another aspect of this involves a packaged kit for a patient to use in the treatment of HCV infection or in the prevention of HCV infection, comprising: a single or a plurality of pharmaceutical formulation of each pharmaceutical component; a container housing the pharmaceutical formulation(s) during storage and prior to administration; and instructions for carrying out drug administration in a manner effective to treat or prevent HCV infection.

Accordingly, this invention provides kits for the simultaneous or sequential administration of a compound of Formula (I), an additional anti-viral agent and a CYP inhibitor (or derivatives thereof are prepared in a conventional manner. Typically, such a kit will comprise, e.g., a composition of a compound of Formula (I) and optionally the additional agent (s) in a pharmaceutically acceptable carrier (and in one or in a plurality of pharmaceutical formulations) and written instructions for the simultaneous or sequential administration.

In another embodiment, a packaged kit is provided that contains one or more dosage forms for self administration; a container means, preferably sealed, for housing the dosage forms during storage and prior to use; and instructions for a patient to carry out drug administration. The instructions will typically be written instructions on a package insert, a label, and/or on other components of the kit, and the dosage form or forms are as described herein. Each dosage form may be individually housed, as in a sheet of a metal foil-plastic laminate with each dosage form isolated from the others in individual cells or bubbles, or the dosage forms may be housed in a single container, as in a plastic bottle. The present kits will also typically include means for packaging the individual kit components, i.e., the dosage forms, the container means, and the written instructions for use. Such packaging means may take the form of a cardboard or paper box, a plastic or foil pouch, etc.

DEFINITIONS

Listed below are definitions of various terms used to describe this invention. These definitions apply to the terms as they are used throughout this specification and claims, unless otherwise limited in specific instances, either individually or as part of a larger group.

The term "aromatic group," as used herein, refers to a moiety that comprises at least one aromatic ring.

The term "aryl," as used herein, refers to a mono- or polycyclic carbocyclic ring system comprising at least one aromatic ring, including, but not limited to, phenyl, naphthyl, tetrahydronaphthyl, indanyl, indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic ring system comprising at least one aromatic ring having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl. A polycyclic aryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic.

The term "tricyclic aryl" or "tricyclic heteroaryl" refers to a ring system consisting of three rings wherein at least one ring is aromatic.

The terms "$C_1$-$C_4$ alkyl," "$C_1$-$C_6$ alkyl," "$C_1$-$C_8$ alkyl," "$C_2$-$C_4$ alkyl," or "$C_2$-$C_6$ alkyl," as used herein, refer to saturated, straight- or branched-chain hydrocarbon radicals containing between one and four, one and six, one and eight carbon atoms, or the like, respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The terms "$C_2$-$C_8$ alkenyl," "$C_2$-$C_4$ alkenyl," "$C_3$-$C_4$ alkenyl," or "$C_3$-$C_6$ alkenyl," as used herein, refer to straight- or branched-chain hydrocarbon radicals containing from two to eight, or two to four carbon atoms, or the like, having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl, and the like.

The terms "$C_2$-$C_8$ alkynyl," "$C_2$-$C_4$ alkynyl," "$C_3$-$C_4$ alkynyl," or "$C_3$-$C_6$ alkynyl," as used herein, refer to straight- or branched-chain hydrocarbon radicals containing from two to eight, or two to four carbon atoms, or the like, having at least one carbon-carbon triple bond by the removal of a single hydrogen atom. Representative alkynyl groups include, but are not limited to, for example, ethynyl, 1-propynyl, 1-butynyl, heptynyl, octynyl, and the like.

The term "$C_3$-$C_8$-cycloalkyl", or "$C_5$-$C_7$-cycloalkyl," as used herein, refers to a monocyclic or polycyclic saturated carbocyclic ring compound, and the carbon atoms may be optionally oxo-substituted. Examples of $C_3$-$C_8$-cycloalkyl include, but not limited to, cyclopropyl, cyclobutyl, cyclopentyl, cyclohexyl, cyclopentyl and cyclooctyl; and examples of $C_5$-$C_7$-cycloalkyl include, but not limited to, cyclopentyl, cyclohexyl, bicyclo[2.2.1]heptyl, and the like.

The term "$C_3$-$C_8$ cycloalkenyl", or "$C_5$-$C_7$ cycloalkenyl" as used herein, refers to monocyclic or polycyclic carbocyclic ring compound having at least one carbon-carbon double bond, and the carbon atoms may be optionally oxo-substituted. Examples of $C_3$-$C_8$ cycloalkenyl include, but not limited to, cyclopropenyl, cyclobutenyl, cyclopentenyl, cyclohexenyl, cycloheptenyl, cyclooctenyl, and the like; and examples of $C_5$-$C_7$ cycloalkenyl include, but not limited to, cyclopentenyl, cyclohexenyl, cycloheptenyl, and the like.

The term "arylalkyl", as used herein, refers to an aryl-substituted alkyl group. More preferred arylalkyl groups are aryl-$C_1$-$C_6$-alkyl groups.

The term "heteroarylalkyl", as used herein, refers to a heteroaryl-substituted alkyl group. More preferred heteroarylalkyl groups are heteroaryl-$C_1$-$C_6$-alkyl groups.

It is understood that any alkyl, alkenyl, alkynyl, cycloalkyl and cycloalkenyl moiety described herein can also be an aliphatic group. Any cycloalkyl or cycloalkenyl moiety described herein can also be an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as, O, OH, NH, $NH_2$, C(O), $S(O)_2$, C(O)O, C(O)NH, OC(O)O, OC(O)NH, OC(O)$NH_2$, $S(O)_2$NH, $S(O)_2$$NH_2$, NHC(O)$NH_2$, NHC(O)C(O)NH, NHS(O)$_2$NH, NHS(O)$_2$$NH_2$, C(O)NHS(O)$_2$, C(O)NHS(O)$_2$NH or C(O)NHS(O)$_2$$NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched or cyclic and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted. A linear aliphatic group is a non-cyclic aliphatic group. It is to be understood that when an aliphatic group or a linear aliphatic group is said to "contain" or "include" or "comprise" one or more specified functional groups, the linear aliphatic group can be selected from one or more of the specified functional groups or a combination thereof, or a group wherein one or more carbons of a non-aromatic hydrocarbon (optionally substituted) is replaced by a specified functional group. In some examples, the linear aliphatic group can be represented by the formula M-Y-M', where M and M' are each independently absent or an alkyl, alkenyl or alkynyl, each optionally substituted, and Y is a functional group. In some examples, Y is selected from the group consisting of C(O), $S(O)_2$, C(O)O, C(O)N($R^{11}$), OC(O)O, OC(O)N($R^{11}$), $S(O)_2$N($R^{11}$), N($R^{11}$)C(O)N($R^{11}$), N($R^{11}$)C(O)C(O)N($R^{11}$), N($R^{11}$)S(O)$_2$N($R^{11}$), C(O)N($R^{11}$)S(O)$_2$ or C(O)N($R^{11}$)S(O)$_2$N($R^{11}$); wherein $R^{11}$ is as previously defined. In another aspect of the invention, an exemplary linear aliphatic group is an alkyl, alkenyl or alkynyl, each optionally substituted, which is interrupted or terminated by a functional group such as described herein.

The term "alicyclic," as used herein, denotes a monovalent group derived from a monocyclic or bicyclic saturated carbocyclic ring compound by the removal of a single hydrogen atom, and the carbon atoms may be optionally oxo-substituted. Examples include, but not limited to, cyclopropyl, cyclobutyl, cyclopentyl, cyclohexyl, bicyclo[2.2.1]heptyl, and bicyclo[2.2.2]octyl. Such alicyclic groups may be further substituted.

The terms "heterocyclic" or "heterocycloalkyl" can be used interchangeably and referred to a non-aromatic ring or a bi- or tri-cyclic group fused system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted.

It is understood that any alkyl, alkenyl, alkynyl, alicyclic, cycloalkyl, cycloalkenyl, aryl, heteroaryl, heterocyclic, and aliphatic moiety, or the like, described herein can also be a divalent group when used as a linkage to connect two groups or substituents, which can be at the same or different atom(s).

The term "substituted" refers to substitution by independent replacement of one, two, or three or more of the hydrogen atoms with substituents including, but not limited to, —F, —Cl, —Br, —I, —OH, protected hydroxy, —NO$_2$, —N$_3$, —CN, —NH$_2$, protected amino, oxo, thioxo, —NH—C$_1$-C$_{12}$-alkyl, —NH—C$_2$-C$_8$-alkenyl, —NH—C$_2$-C$_8$-alkynyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_8$-alkenyl, —O—C$_2$-C$_8$-alkynyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_8$-alkenyl, —C(O)—C$_2$-C$_8$-alkynyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_8$-alkenyl, —CONH—C$_2$-C$_8$-alkynyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_8$-alkenyl, —OCO$_2$—C$_2$-C$_8$-alkenyl, —OCO$_2$—C$_3$-C$_{12}$-cycloalkyl, —OCO$_2$-aryl, —OCO$_2$-heteroaryl, —OCO$_2$-heterocycloalkyl, —CO$_2$—C$_1$-C$_{12}$ alkyl, —CO$_2$—C$_2$-C$_8$ alkenyl, —CO$_2$—C$_2$-C$_8$ alkynyl, CO$_2$—C$_3$-C$_{12}$-cycloalkyl, —CO$_2$-aryl, CO$_2$-heteroaryl, CO$_2$-heterocyloalkyl, —OCONH$_2$, —OCONH—C$_1$-C$_{12}$-alkyl, —OCONH—C$_2$-C$_8$-alkenyl, —OCONH—C$_2$-C$_8$-alkynyl, —OCONH—C$_3$-C$_{12}$-cycloalkyl, —OCONH-aryl, —OCONH-heteroaryl, —OCONH— heterocyclo-alkyl, —NHC(O)H, —NHC(O)—C$_1$-C$_{12}$-alkyl, —NHC(O)—C$_2$-C$_8$-alkenyl, —NHC(O)—C$_2$-C$_8$-alkynyl, —NHC(O)—C$_3$-C$_{12}$-cycloalkyl, —NHC(O)-aryl, —NHC(O)-heteroaryl, —NHC(O)-heterocyclo-alkyl, —NHCO$_2$—C$_1$-C$_{12}$-alkyl, —NHCO$_2$—C$_2$-C$_8$-alkenyl, —NHCO$_2$—C$_2$-C$_8$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_8$-alkenyl, —NHC(O)NH—C$_2$-C$_8$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_8$-alkenyl, —NHC(S)NH—C$_2$-C$_8$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_8$-alkenyl, —NHC(NH)NH—C$_2$-C$_8$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_8$-alkenyl, —NHC(NH)—C$_2$-C$_8$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_8$-alkenyl, —C(NH)NH—C$_2$-C$_8$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_8$-alkenyl, —S(O)—C$_2$-C$_8$-alkynyl, —S(O)—C$_3$-C$_{12}$-cycloalkyl, —S(O)-aryl, —S(O)-heteroaryl, —S(O)-heterocycloalkyl, —SO$_2$NH$_2$, —SO$_2$NH—C$_1$-C$_{12}$-alkyl, —SO$_2$NH—C$_2$-C$_8$-alkenyl, —SO$_2$NH—C$_2$-C$_8$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_8$-alkenyl, —NHSO$_2$—C$_2$-C$_8$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_8$-alkenyl, —S—C$_2$-C$_8$-alkynyl, —S—C$_3$-C$_{12}$-cycloalkyl, —S-aryl, —S-heteroaryl, —S-heterocycloalkyl, or methylthiomethyl. It is understood that the aryls, heteroaryls, alkyls, and the like can be further substituted.

The term "halogen," as used herein, refers to an atom selected from fluorine, chlorine, bromine and iodine.

The term "hydrogen" includes hydrogen and deuterium. In addition, the recitation of an atom includes other isotopes of that atom so long as the resulting compound is pharmaceutically acceptable.

The term "hydroxy activating group", as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxy", as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxycarbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenylmethyl (trityl), methoxymethyl, methylthiomethyl, benzyloxymethyl, 2-(trimethylsilyl)ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group", as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

The term "protic solvent' as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* $2^{nd}$ Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995), and subsequent editions thereof.

The term "subject" as used herein refers to an animal. Preferably, the animal is a mammal. More preferably, the mammal is a human. A subject also refers to, for example, dogs, cats, horses, cows, pigs, guinea pigs, fish, birds and the like.

The compounds of Formula (I) may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds of Formula (I) contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of Formula (I) may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences*, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., *Journal of Drug Deliver Reviews*, 8:1-38 (1992); Bundgaard, *J. of Pharmaceutical Sciences*, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The present invention also relates to solvates of the compounds of Formula (I), for example hydrates.

This invention also encompasses pharmaceutical compositions containing, and methods of treating viral infections through administering, pharmaceutically acceptable prodrugs of compounds of Formula (I). For example, compounds of Formula (I) having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

Pharmaceutical Compositions

The pharmaceutical compositions of the present invention comprise a therapeutically effective amount of a compound that inhibits function of the HCV NS5A protein and an additional anti-viral agent or anti-HCV agent formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

Antiviral Activity

An inhibitory amount or dose of the compounds of Formula (I) may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound or agent described herein and/or a combination of a compound that inhibits function of the HCV NS5A protein and an additional anti-viral agent or combination of anti-viral agents is meant to describe an amount of the compound, or anti-viral agent, either alone or in combination with one another, which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound of Formula (I) may range from about 0.1 mg/Kg to about 500 mg/Kg, preferably from about 1 to about 50 mg/Kg. Effective doses of a compound that inhibits function of the HCV NS5A protein and/or an additional anti-viral agent or combination of anti-viral agents will also vary depending on route of administration, as well as the possibility of co-usage with other agents. It will be understood, however, that the total daily usage of the combinations and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds that inhibits function of the HCV NS5A protein administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds that inhibit function of the HCV NS5A protein and/or an additional anti-viral agent or combination of anti-viral agents described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, or a combination thereof. Exemplary dosages range from about 0.1 to about 500 mg/kg of body weight, alternatively dosages between 1 mg and 1000 mg/dose, every 4 to 120 hours, or according to the requirements of the particular drug. The methods herein contemplate administration of an effective amount of the combination to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient(s) that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the Formula described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" includes but not limited to, immune therapies (eg. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (eg N-acetylcysteine), cytokine agonists, cytokine antagonists, lung surfactants and/or antimicrobial and anti-viral agents (eg ribavirin and amantidine). The compositions according to the invention may also be used in combination with gene replacement therapy.

Combination and Alternation Therapy for HCV

It has been recognized that drug-resistant variants of HCV can emerge after prolonged treatment with an antiviral agent. Drug resistance most typically occurs by mutation of a gene that encodes for a protein such as an enzyme used in viral replication, and most typically in the case of HCV, RNA polymerase, protease, or helicase.

Recently, it has been demonstrated that the efficacy of a drug against a viral infection, such as HIV, can be prolonged, augmented, or restored by administering the drug in combination or alternation with a second, and perhaps third, antiviral compound that induces a different mutation from that caused by the principal drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

As discussed in detail above, a compound that inhibits function of the HCV NS5A protein can also be administered in combination or alternation with antiviral agent. Exemplary antiviral agents include ribavarin, interferon, interleukin or a stabilized prodrug of any of them. More broadly described, the compound can be administered in combination or alternation with any of the anti-HCV drugs listed in Table 2 below.

TABLE 2

| Drug name | Drug category | Pharmaceutical Company |
| --- | --- | --- |
| PEGASYS pegylated interferon alfa-2a | Long acting interferon | Roche |
| INFERGEN interferon alfacon-1 | Long acting interferon | InterMune |
| OMNIFERON natural interferon | Long acting interferon | Viragen |
| ALBUFERON | Long acting interferon | Human Genome Sciences |
| REBIF interferon beta-la | Interferon | Ares-Serono |
| Omega Interferon | Interferon | BioMedicine |
| Oral Interferon alpha | Oral Interferon | Amarillo Biosciences |
| Interferon gamma-lb | Anti-fibrotic | InterMune |
| IP-501 | Anti-fibrotic | InterMune |
| Merimebodib VX-497 | IMPDH inhibitor (inosine monophosphate dehydrogenase) | Vertex |
| AMANTADINE (Symmetrel) | Broad Antiviral Agent | Endo Labs Solvay |
| IDN-6556 | Apotosis regulation | Idun Pharma. |
| XTL-002 | Monclonal Antibody | XTL |
| HCV/MF59 | Vaccine | Chiron |
| CIVACIR | Polyclonal Antibody Therapeutic vaccine | NABI Innogenetics |
| VIRAMIDINE | Nucleoside Analogue | ICN |
| ZADAXIN (thymosin alfa-1) | Immunomodulator | Sci Clone |
| CEPLENE (histamine) | Immunomodulator | Maxim |
| VX 950/LY 570310 | Protease inhibitor | Vertex/Eli Lilly |
| ISIS 14803 | Antisense | Isis Pharmaceutical/Elan |
| IDN-6556 | Caspase inhibitor | Idun Pharmaceuticals |
| JTK 003 | Polymerase Inhibitor | AKROS Pharma |
| Tarvacin | Anti-Phospholipid Therapy | Peregrine |
| HCV-796 | Polymerase Inhibitor | ViroPharma/Wyeth |
| CH-6 | Protease inhibitor | Schering |

TABLE 2-continued

| Drug name | Drug category | Pharmaceutical Company |
| --- | --- | --- |
| ANA971 | Isatoribine | ANADYS |
| ANA245 | Isatoribine | ANADYS |
| CPG 10101 (Actilon) | Immunomodulator | Coley |
| Rituximab (Rituxam) | Anti-CD2O Monoclonal Antibody | Genetech/IDEC |
| NM283 (Valopicitabine) | Polymerase Inhibitor | Idenix Pharmaceuticals |
| HepX ™-C | Monoclonal Antibody | XTL |
| IC41 | Therapeutic Vaccine | Intercell |
| Medusa Interferon | Longer acting interferon | Flamel Technology |
| E-1 | Therapeutic Vaccine | Innogenetics |
| Multiferon | Long Acting Interferon | Viragen |
| BILN 2061 | Protease inhibitor | Boehringer-Ingelheim |
| TMC435350 | Protease inhibitor | Tibotec/Medivir |
| Telaprevir (VX-950) | Protease inhibitor | Vertex |
| Boceprevir (SCH 503034) | Protease inhibitor | Schering-Plough |
| ACH-1625 | Protease inhibitor | Achillion |
| ABT-450 | Protease inhibitor | Abbott/Enanta |
| BI-201335 | Protease inhibitor | Boehringer-Ingelheim |
| PHX-1766 | Protease inhibitor | Phenomix |
| VX-500 | Protease inhibitor | Vertex |
| MK-7009 | protease inhibitor | Merck |
| R7227 (ITMN-191) (Danoprevir) | protease inhibitor | InterMune |
| Narlaprevir (SCH 900518) | Protease inhibitor | Schering/Merck |
| Alinia (nitazoxanide) | To be determined | Romark |
| ABT-072 | Polymerase Inhibitor | Abbott |
| ABT-333 | Polymerase Inhibitor | Abbott |
| Filibuvir (PF-00868554) | Polymerase Inhibitor | Pfizer |
| VCH-916 | Polymerase Inhibitor | Vertex |
| R7128 (PSI6130) | Polymerase Inhibitor | Roche/Pharmasset |
| IDX184 | Polymerase Inhibitor | Idenix |
| R1626 | Polymerase inhibitor | Roche |
| MK-3281 | Polymerase inhibitor | Merck |
| PSI-7851 | Polymerase inhibitor | Pharmasset |
| ANA598 | Polymerase inhibitor | Anadys Pharmaceuticals |
| BI-207127 | Polymerase inhibitor | Boehringer-Ingelheim |
| GS-9190 | Polymerase inhibitor | Gilead |
| VCH-759 | Polymerase Inhibitor | Vertex |
| GSK625433 | Polymerase inhibitor | Glaxo Smith Kline |
| Clemizole | NS4B inhibitor | Eiger Biopharmaceuticals |
| A-832 | NS5A inhibitor | ArrowTherapeutics |
| BMS-790052 | NS5A inhibitor | Bristol-Myers-Squibb |
| ITX5061 | Entry inhibitor | iTherx |
| GS-9450 | Caspase inhibitor | Gilead |
| ANA773 | TLR agonist | Anadys |
| CYT107 | immunomodulator | Cytheris |
| SPC3649 (LNA-antimiR ™-122) | microRNA | Santaris Pharma |
| Debio 025 | Cyclophilin inhibitor | Debiopharm |
| SCY-635 | Cyclophilin inhibitor | Scynexis |
| GSK 625433 | Polymerase inhibitor | Glaxo Smith Kline |

In some aspects, the pharmaceutical composition comprises a compound of Formula (IIc), (IId), (IIe) or (IIf) in an amount effective to inhibit the function of the HCV NS5A protein and an effective amount of additional agent having anti-HCV activity selected from those listed in Table 2 above. In an additional aspect, the pharmaceutical composition comprises a compound of Formula (IIc), (IId), (IIe) or (IIf) in an amount effective to inhibit the function of the HCV NS5A protein and an effective amount of an additional agent having anti-viral activity selected from the group consisting of a cyclosporine analog, ITMN-191, boceprivir, telaprivir (VX-950), R7128, GSK 625433, and interferon α.

The invention also encompasses a method for treating a patient suffering from a viral infection comprising administering to said patient a compound of Formula (IIc), (IId), (IIe) or (IIf) in an amount effective to inhibit the function of the HCV NS5A protein and an effective amount of additional agent having anti-HCV activity selected from those listed in Table 2 above. In an additional aspect, the invention is a method of treating a patient suffering from a viral infection comprising administering to said patient a compound of Formula (IIc), (IId), (IIe) or (IIf) in an amount effective to inhibit the function of the HCV NS5A protein and an effective amount of an additional agent having anti-viral activity selected from the group consisting of a cyclosporine analog, ITMN-191, boceprivir, telaprivir (VX-950), R7128, GSK 625433, and interferon α.

In yet an additional aspect, the pharmaceutical composition comprises a compound of Formula (IIc) and an effective amount of an additional agent having anti-HCV activity selected from those listed in Table 2 above. In a further embodiment, the pharmaceutical composition comprises a compound of Formula (IIc) in an amount effective to inhibit the function of the HCV NS5A protein and an effective amount of an additional agent having anti-viral activity selected from the group consisting of a cyclosporine analog, ITMN-191, boceprivir, telaprivir (VX-950), R7128, GSK 625433, interferon α.

The invention also includes a method for treating a patient suffering from a viral infection comprising administering to said patient a compound of Formula (IIc) and administering an effective amount of an additional agent having anti-HCV activity selected from those listed in Table 2 above. In a further embodiment, the method comprises administering a compound of Formula (IIc) in an amount effective to inhibit the function of the HCV NS5A protein and administering an effective amount of an additional agent having anti-viral activity selected from the group consisting of a cyclosporine analog, ITMN-191, boceprivir, telaprivir (VX-950), R7128, GSK 625433, interferon α.

In another embodiment, the pharmaceutical composition comprises a compound selected from the group consisting of Compound 90, Compound 93, Compound 95 and pharmaceutically acceptable salts of these compounds, in an amount effective to inhibit the function of the HCV NS5A protein and an effective amount of an additional agent having anti-HCV activity selected from those listed in Table 2 above. In yet another aspect, the pharmaceutical composition comprises a compound selected from the group consisting of Compound 90, Compound 93, Compound 95 and pharmaceutically acceptable salts of these compounds in an amount effective to inhibit the function of the HCV NS5A protein and an effective amount of an additional agent having anti-viral activity selected from the group consisting of a cyclosporine analog, ITMN-191, boceprivir, telaprivir (VX-950), R7128, GSK 625433, and interferon α. In a further aspect, the pharmaceutical composition comprises a compound selected from the group consisting of Compound 90, Compound 93, Compound 95 and pharmaceutically acceptable salts of these compounds in an amount effective to inhibit the function of the HCV NS5A protein and an effective amount of an additional agent having anti-viral activity selected from the group consisting of boceprivir, R7128, GSK 625433 and interferon-α. In an additional aspect, the pharmaceutical composition comprises a compound selected from the group consisting of Compound 90, Compound 93 Compound 95 and pharmaceutically acceptable salts of these compounds in an amount effective to inhibit the function of the HCV NS5A protein and an effective amount of telaprivir (VX-950). In another embodiment, the pharmaceutical composition comprises Compound 90 or a pharmaceutically acceptable salt thereof in an amount effective to inhibit the function of HCV NS5A protein and an effective amount of an additional agent having antiviral activity selected from the group consisting of boceprivir and R7128. In yet another embodiment, the pharmaceutical composition comprises Compound 95 or a pharmaceutically acceptable salt thereof in an amount effective to inhibit the function of HCV NS5A protein and an effective amount of an effective amount of an additional agent having antiviral activity selected from the group consisting of boceprivir and R7128. In another embodiment, the pharmaceutical composition comprises Compound 93 or a pharmaceutically acceptable salt thereof in an amount effective to inhibit the function of HCV NS5A protein and an effective amount of an additional agent having antiviral activity selected from the group consisting of boceprivir, GSK 625433 and interferon-α.

The invention is additionally directed to a method for treating a patient suffering from a viral infection comprising administering to said patient a compound selected from the group consisting of Compound 90, Compound 93, Compound 95 and pharmaceutically acceptable salts of these compounds in an amount effective to inhibit the function of the HCV NS5A protein and administering an effective amount of an additional agent having anti-HCV activity selected from those listed in Table 2 above. In yet another aspect, the method comprises administering a compound selected from the group consisting of Compound 90, Compound 93, Compound 95 and pharmaceutically acceptable salts of these compounds in an amount effective to inhibit the function of the HCV NS5A protein and administering an effective amount of an additional agent having anti-viral activity selected from the group consisting of a cyclosporine analog, ITMN-191, boceprivir, telaprivir (VX-950), R7128, GSK 625433, and interferon α. In a further aspect, the method comprises administering a compound selected from the group consisting of Compound 90, Compound 93, Compound 95 and pharmaceutically acceptable salts of these compounds in an amount effective to inhibit the function of the HCV NS5A protein and administering an effective amount of an additional agent having anti-viral activity selected from the group consisting of boceprivir, R7128, GSK 625433 and interferon-α. In an additional aspect, the method comprises administering a compound selected from the group consisting of Compound 90, Compound 93, Compound 95 and pharmaceutically acceptable salts of these compounds in an amount effective to inhibit the function of the HCV NS5A protein and administering an effective amount of telaprivir (VX-950). In another embodiment, the method comprises administering Compound 90 or a pharmaceutically acceptable salt thereof in an amount effective to inhibit the function of HCV NS5A protein and administering an effective amount of an additional agent having antiviral activity selected from the group consisting of boceprivir and R7128. In yet another embodiment, the method comprises administering Compound 95 or a pharmaceutically acceptable salt thereof in an amount effective to inhibit the function of HCV NS5A protein and administering an effective amount of an effective amount of an additional agent having antiviral activity selected from the group consisting of boceprivir and R7128. In another embodiment, the method comprises administering Compound 93 or a pharmaceutically acceptable salt thereof in an amount effective to inhibit the function of HCV NS5A protein and administering an effective amount of an additional agent having antiviral activity selected from the group consisting of boceprivir, GSK 625433 and interferon-α.

R7128 is prodrug of PSI-6130. R7128 has the chemical structure shown below:

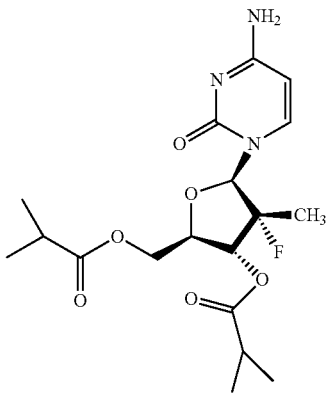

GSK 625433 (1-[4-(1,1-dimethylethyl)-3-methoxybenzoyl]-4-(methoxymethyl)-2-(1H-pyrazol-1-ylmethyl)-5-(2-thiazolyl)-,(4R,5S)-rel-D-Proline) has the chemical structure shown below:

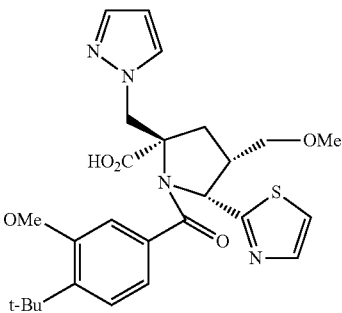 [SMILES: COC[C@H]1C[C@@](Cn2cccn2)(C(=O)O)N(C(=O)c2ccc(C(C)(C)C)c(OC)c2)[C@H]1c1nccs1]

Unless otherwise defined, all technical and scientific terms used herein are accorded the meaning commonly known to one of ordinary skill in the art. All publications, patents, published patent applications, and other references mentioned herein are hereby incorporated by reference in their entirety.

Synthetic Methods

Exemplary compounds of Formula (I) as well as other compounds that inhibit the replication of RNA-containing virus have been described in copending U.S. application Ser. No. 12/702,673 filed Feb. 9, 2010 entitled "Linked Dibenzimidiazole Antivirals"; U.S. application Ser. No. 12/702,692 filed Feb. 9, 2010 entitled "Linked Dibenzimidazole Derivatives"; U.S. application Ser. No. 12/702,802 filed Feb. 9, 2010 entitled "Linked Dibenzimidazole Derivatives"; U.S. application Ser. No. 12/707,190 filed Feb. 17, 2010 entitled "Linked Diimidazole Derivatives"; U.S. application Ser. No. 12/707,200 filed Feb. 17, 2010 entitled "Linked Diimidazole Derivatives"; U.S. application Ser. No. 12/707,210 filed Feb. 17, 2010 entitled "Hepatitis C Virus Inhibitors"; U.S. application Ser. No. 12/714,583 filed Mar. 1, 2010 entitled "Novel Benzimidazole Derivatives"; and U.S. application Ser. No. 12/714,576 filed Mar. 1, 2010 entitled "Hepatitis C Virus Inhibitors"; the contents of each of which are expressly incorporated by reference herein.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

Biological Activity

The following examples are intended to illustrate rather than limit the invention.

1. HCV Replicon Cell Lines

HCV replicon cell lines (kindly provided by R. Bartenschlager) isolated from colonies as described by Lohman et. al. (Lohman et al. (1999) Science 285: 110-113, expressly incorporated by reference in its entirety) and used for all experiments. The HCV replicon has the nucleic acid sequence set forth in EMBL Accession No.: AJ242651, the coding sequence of which is from nucleotides 1801 to 8406.

The coding sequence of the published HCV replicon was synthesized and subsequently assembled in a modified plasmid pBR322 (Promega, Madison, Wis.) using standard molecular biology techniques. One replicon cell line ("SGR 11-7") stably expresses HCV replicon RNA which consists of (i) the HCV 5'UTR fused to the first 12 amino acids of the capsid protein, (ii) the neomycin phosphotransferase gene (neo), (iii) the IRES from encephalomyocarditis virus (EMCV), and (iv) HCV NS2 to NS5B genes and the HCV 3'UTR. Another replicon cell line ("Huh-luc/neo-ET") described by Vrolijk et. al. (Vrolijk et. al. (2003) Journal of Virological Methods 110:201-209, expressly incorporated by reference in its entirety) stably expresses HCV replicon RNA which consists of (i) the HCV 5'UTR fused to the first 12 amino acids of the capsid protein, (ii) the firefly luciferase reporter gene, (iii) the ubiquitin gene, (iv) the neomycin phosphotransferase gene (neo), (v) the IRES from encephalomyocarditis virus (EMCV), and (vi) HCV NS3 to NS5B genes that harbor cell culture adaptive mutations (E1202G, T12801, K1846T) and the HCV 3'UTR.

These cell lines are maintained at 37° C., 5% $CO_2$, 100% relative humidity in DMEM (Cat#11965-084, Invitrogen), with 10% fetal calf serum ("FCS", Invitrogen), 1% nonessential amino acids (Invitrogen), 1% of Glutamax (Invitrogen), 1% of 100× penicillin/streptomycin (Cat#15140-122, Invitrogen) and Geneticin (Cat#10131-027, Invitrogen) at 0.75 mg/ml or 0.5 mg/ml for 11-7 and Huh-luc/neo-ET cells, respectively.

2. HCV Replicon Drug Screening Assay

EC50 values of single agent compounds and combinations were determined by HCV RNA detection using quantitative RT-PCR, according to the manufacturer's instructions, with a TAQMAN® One-Step RT-PCR Master Mix Reagents Kit (Cat#AB 4309169, Applied Biosystems) on an ABI Model 7500 thermocycler. The TaqMan primers to use for detecting and quantifying HCV RNA are 5'-GCTGCGGCCTGTC-GAGCT-3' (SEQ ID NO: 1), 5'-CAAGGTCGTCTCCG-CATAC-3' (SEQ ID NO: 2) and the probe 5'-FAM-CGAAGCTCCAGGACTGCACGATGCT-BHQ-3' (SEQ ID NO: 3) obtained from Integrated DNA Technologies. HCV RNA is normalized to GAPDH RNA levels in drug-treated cells, which is detected and quantified using the Human GAPDH Endogenous Control Mix (Applied Biosystems, AB 4310884E). Total cellular RNA is purified from 96-well plates using the RNAqueous 96 kit (Ambion, Cat#AM1812). Chemical agent cytotoxicity was evaluated using an MTS assay according to the manufacturer's directions (Promega).

The compounds described herein can be effective against the HCV 1b genotype. It should also be understood that the compounds can inhibit multiple genotypes of HCV. In one embodiment, compounds of Formula (I) are active against the 1a, 1b, 2a, 2b, 3a, 4a, and 5a genotypes. The following table shows the $EC_{50}$ values of representative compounds of the present invention against the HCV 1b genotype from the above described quantitative RT-PCR or luciferase assay. The $EC_{50}$ ranges were classified into the following groups: A>10 nM; B 1-10 nM; C<1 nM. The potential cytotoxicities of each agent were analyzed in parallel by MTS assay and are greater than 3 uM for all agents.

therapies with Interferon alpha, cyclosporine analogs and inhibitors targeting other HCV proteins. The acute effects of combinations of drugs were studied in the "Huh-luc/neo-ET" replicon with each chemical agent titrated in an X or Y direction in a 6 point two-fold dilution curve centered around the EC50 of each drug. Briefly, replicon cells were seeded at 7,000 cells per well in 90 ul DMEM (without phenol red, Invitrogen Cat. #31053-036) per well with 10% FCS, 1% non-essential amino acids, 1% of Glutamax and 1% of 100× penicillin/streptomycin and incubated overnight at 37° C., 5% C02, 100% relative humidity. 16-20 h after seeding cells, test compounds previously solubilized and titrated in dimethyl sulfoxide ("DMSO") from each X plate and Y plate were diluted 1:100 in DMEM (without phenol red, Invitrogen Cat. #31053-036) with 10% FCS, 1% non-essential amino acids, 1% of Glutamax and 1% of 100× penicillin/streptomycin and added directly to the 96-well plate containing cells and growth medium at a 1:10 dilution for a final dilution of compound and DMSO of 1:1000 (0.2% DMSO final concentration). Drug treated cells were incubated at 37° C., 5% C02, 100% relative humidity for 72 hours before performing a luciferase assay using 100 ul per well BriteLite Plus (Perkin Elmer) according to the manufacturer's instructions. Data analysis utilizes the method published by Prichard and Shipman (Antiviral Research, 1990. 14:181-205). Using this method, the combination data were analyzed for antagonistic, additive, or synergistic combination effects across the entire combination surface created by the diluted compounds in combination.

TABLE 3

Genotype-1b replicon $EC_{50}$

| Compound | Range | Compound | Range | Compound | Range | Compound | Range |
|---|---|---|---|---|---|---|---|
| 1 | C | 2 | C | 3 | C | 4 | A |
| 5 | A | 6 | A | 7 | A | 8 | A |
| 9 | C | 10 | C | 11 | C | 12 | C |
| 13 | C | 14 | C | 15 | C | 16 | C |
| 17 | A | 18 | A | 19 | C | 20 | C |
| 21 | C | 22 | C | 23 | A | 24 | C |
| 25 | C | 26 | C | 27 | C | 28 | C |
| 29 | C | 30 | C | 31 | C | 32 | A |
| 33 | C | 34 | C | 35 | C | 36 | C |
| 37 | C | 38 | C | 39 | C | 40 | C |
| 41 | C | 42 | C | 43 | C | 44 | C |
| 45 | C | 46 | C | 47 | C | 48 | C |
| 49 | C | 51 | C | 52 | C | 53 | C |
| 54 | C | 55 | C | 56 | C | 57 | C |
| 58 | C | 59 | C | 60 | C | 61 | C |
| 62 | C | 63 | C | 64 | C | 65 | C |
| 66 | C | 67 | C | 68 | C | 69 | C |
| 70 | C | 71 | C | 72 | C | 73 | C |
| 74 | C | 75 | B | 76 | C | 77 | C |
| 78 | C | 79 | C | 80 | C | 81 | C |
| 82 | C | 83 | C | 84 | C | 85 | C |
| 86 | C | 87 | C | 88 | C | 89 | C |
| 90 | C | 91 | C | 92 | C | 93 | C |
| 94 | C | 95 | C | 96 | C | 97 | C |
| 98 | C | 99 | C | 100 | C | 101 | C |
| 102 | C | 103 | C | 104 | C | 105 | C |
| 106 | C | 107 | C | 108 | C | 109 | C |
| 110 | C | 112 | C | 113 | C | 114 | C |
| 116 | C | 117 | C | 118 | C | 119 | C |
| 120 | A | 121 | B | 122 | C | 123 | C |
| 124 | C | 125 | C | 126 | C | 129 | C |
| 130 | C | 131 | C | | | | |

3. In Vitro Synergy Assay

Since clinical drug resistance often develops in viral infections following single agent therapies, there is a need to assess the additive, antagonistic, or synergistic properties of combination therapies. We used the HCV replicon system to assess the potential use of our NS5A inhibitors in combination We used the HCV replicon system to assess the potential use of our NS5A inhibitor in combination therapies with Interferon alpha, cyclosporine analogs or inhibitors targeting other HCV proteins. Several HCV antivirals, including protease inhibitors (ITMN-191, SCH503034, VX-950), a nucleoside analog (such as those described in WO01/90121 (A2), U.S. Pat. No. 6,348,587B1, WO01/60315 or WO01/32153), a nonnucleoside NS5B polymerase inhibitor (GSK625433), a cyclosporine analog, as well as Interferon alpha, are tested in combination with Compounds 90, 93 or 95 herein, inhibitors of HCV NS5A. Antivirals were tested at five concentrations each, diluted in DMSO by 2-fold dilutions. The antivirals were tested as monotherapies and in combination with Compounds 90, 93 or 95 (described herein) at various concentration ratios. Cells were exposed to compounds for 72 h and the amount of HCV inhibition is then determined using the luciferase assay described above. The potential cytotoxicities of these combined agents were also analyzed in parallel by Alamar blue staining. The degree of antagonism or synergy was determined over a range of drug concentrations, and the combination response curves were fit to assess the antiviral effects of the drug treatment combinations. The combination surfaces were analyzed using the Bliss additivity method of Prichard. The synergy scores at 95% confidence intervals for each drug combination are reported in the table below. Synergy score is defined as the sum of all effect levels greater than or less than that predicted by the Bliss additivity model. In general, synergy scores near 0 indicate additive effects, while values much less than 0 or much greater than 0 suggest antagonism or synergy, respectively.

cell culture. All viral RNA was quantitated using quantitative RT-PCR described above and normalized against total cellular RNA.

Figure 2A:
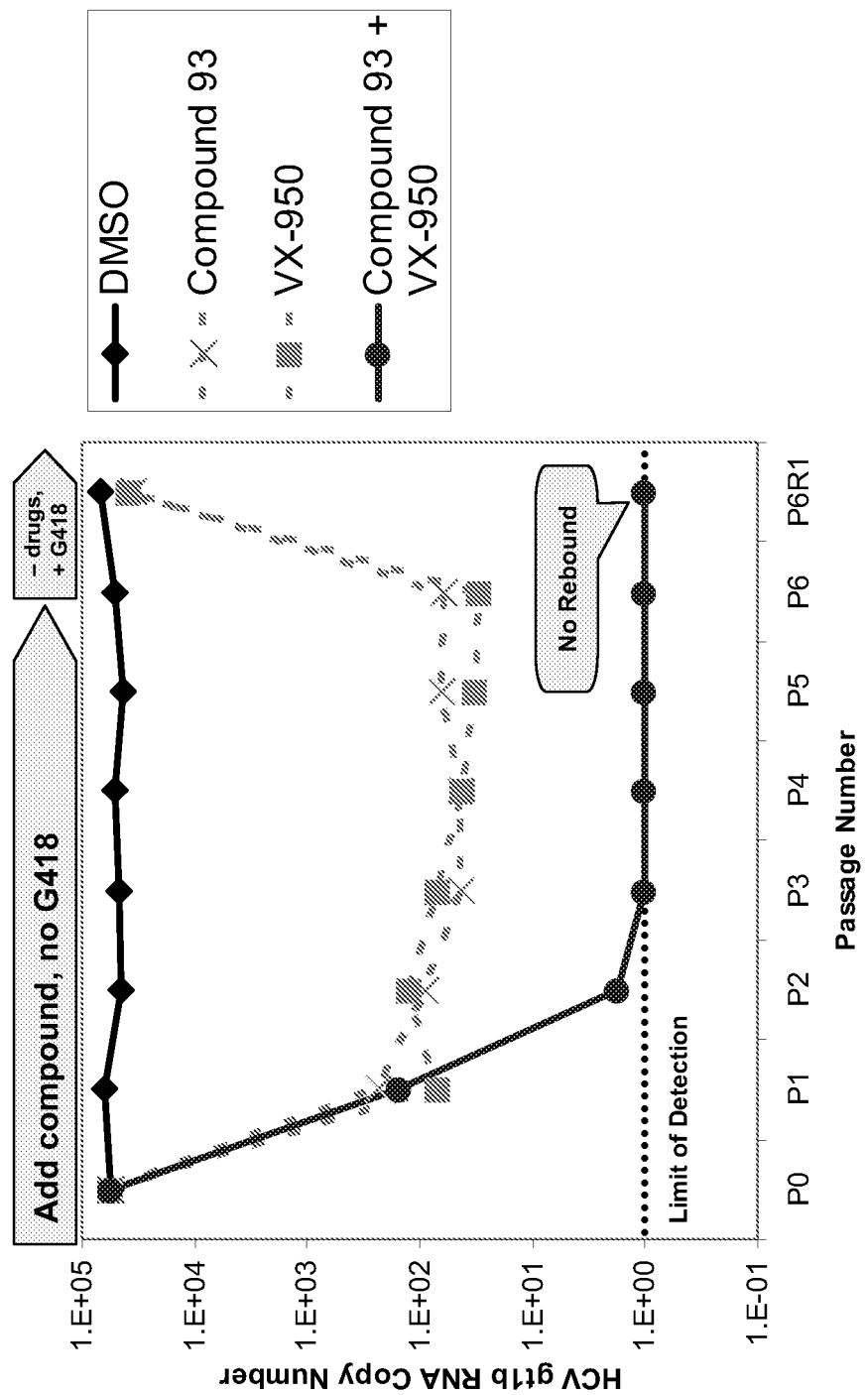
FIG. 2A is a line graph showing HCV RNA copy number over the course of the assay using the vehicle control (DMSO), Compound 93, VX-950 and the combination of Compound 93 and VX-950.
Figure 2B:
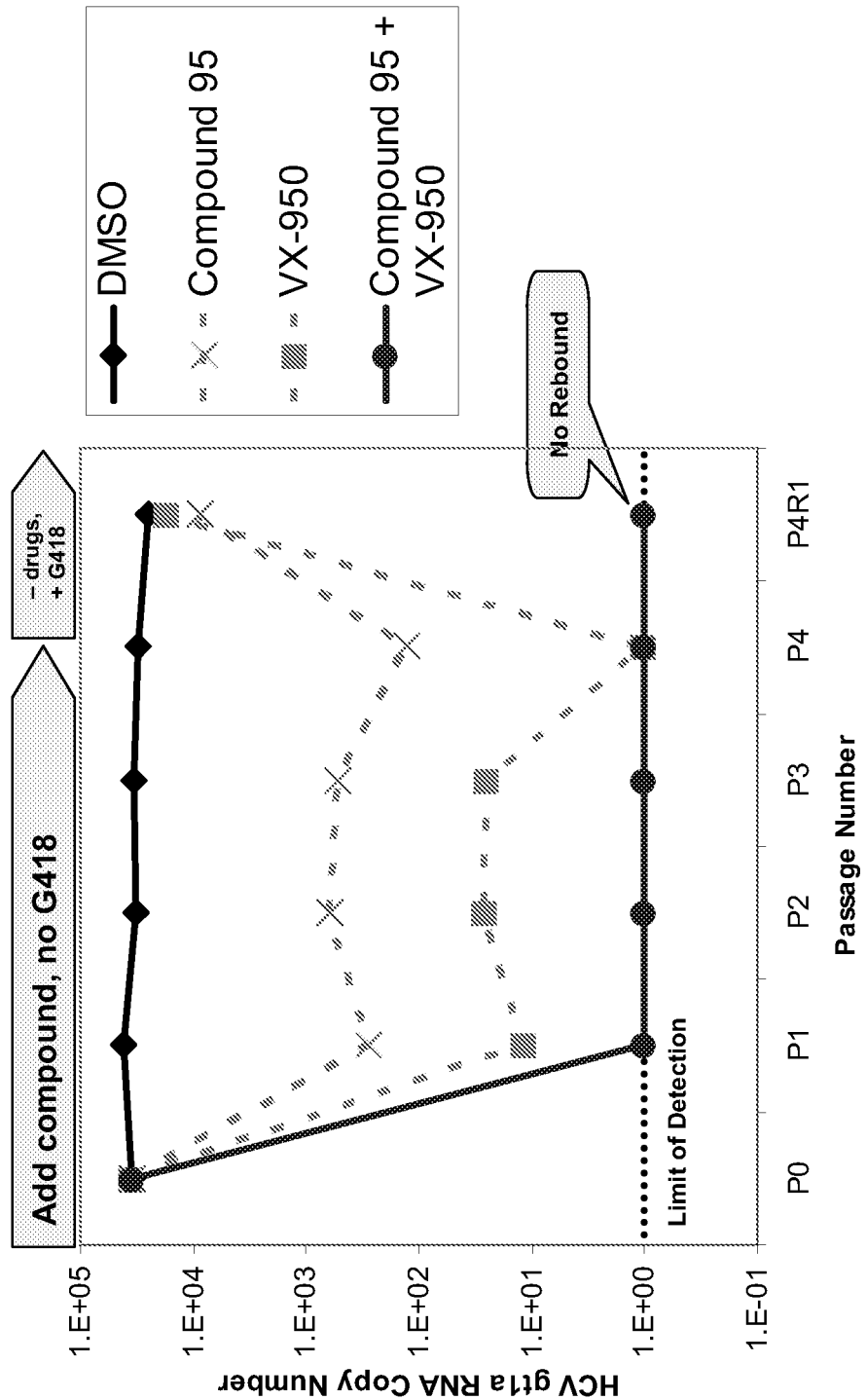
FIG. 2B is a line graph showing HCV RNA copy number over the course of the assay using the vehicle control (DMSO), Compound 95, VX-950 and the combination of Compound 95 and VX-950.

We used the HCV replicon system to assess the long-term impact of our NS5A inhibitor in combination with Interferon alpha, cyclosporine analogs or inhibitors targeting other HCV proteins. As an example, Compounds 93 and 95, inhibitors of the HCV NS5A protein were tested alone and in combination with VX-950, an HCV protease inhibitor, at the concentrations listed in table 5 below. The impact on HCV genotype 1b or 1a (noted) RNA copy number over the course of each assay is also shown in FIGS. 2A and 2B.

TABLE 5

| HCV Genotype | Compounds | Assay Concentrations |
|---|---|---|
| 1b | DMSO | 0.1% |
|  | Compound 93 | 0.105 nM |
|  | VX-950 | 5.0 µM |
|  | Compound 93 + VX-950 | 0.105 nM + 4.5 µM |
| 1a | DMSO | 0.2% |
|  | Compound 95 | 0.75 nM |
|  | VX-950 | 2.5 µM |
|  | Compound 95 + VX-950 | 0.75 nM + 2.0 µM |

5. Suppression of HCV Resistance Assay

"Huh1a7" genotype 1a or "11-7" genotype 1b replicon cells were cultured in the presence of G418 selection and HCV inhibitors at concentrations from between 1×EC50 to

TABLE 4

Two Drug Combinations

| | | Bliss Volume (%) at 95% Confidence Intervals | | | |
|---|---|---|---|---|---|
| Drug X | Drug Y | Synergy | Antagonism | Synergy Score | Result |
| Compound 90 | Cyclosporine analog | 0 | 0 | 0 | Additive |
|  | ITMN-191 | 2 | −9 | −7 | Additive |
|  | Boceprevir (SCH503034) | 48 | 0 | 48 | Synergistic |
|  | Telaprevir (VX-950) | 0 | −1 | −1 | Additive |
|  | R7128 | 34 | 0 | 34 | Synergistic |
|  | GSK625433 | 12 | −1 | 11 | Additive |
|  | Interferon-alpha | 6 | −14 | −8 | Additive |
| Compound 93 | ITMN-191 | 14 | 0 | 14 | Additive |
|  | Boceprevir (SCH503034) | 63 | 0 | 63 | Synergistic |
|  | Telaprevir (VX-950) | 7 | 0 | 7 | Additive |
|  | R7128 | 14 | 0 | 14 | Additive |
|  | GSK625433 | 113 | 0 | 113 | Synergistic |
|  | Interferon-alpha | 38 | 0 | 38 | Synergistic |
| Compound 95 | ITMN-191 | 5 | 0 | 5 | Additive |
|  | Boceprevir (SCH503034) | 44 | 0 | 44 | Synergistic |
|  | Telaprevir (VX-950) | 5 | 0 | 5 | Additive |
|  | R7128 | 28 | 0 | 28 | Synergistic |
|  | GSK625433 | 0 | 0 | 0 | Additive |
|  | Interferon-alpha | 0 | −2 | −2 | Additive |

FIG. 1 provides an example graphical representation of the additivity excess at each combination concentration contributing to the overall synergy score for compound 93 in combination with antiviral compounds.

4. Long-Term RNA Reduction and Viral Rebound Assay

Figure 3A:
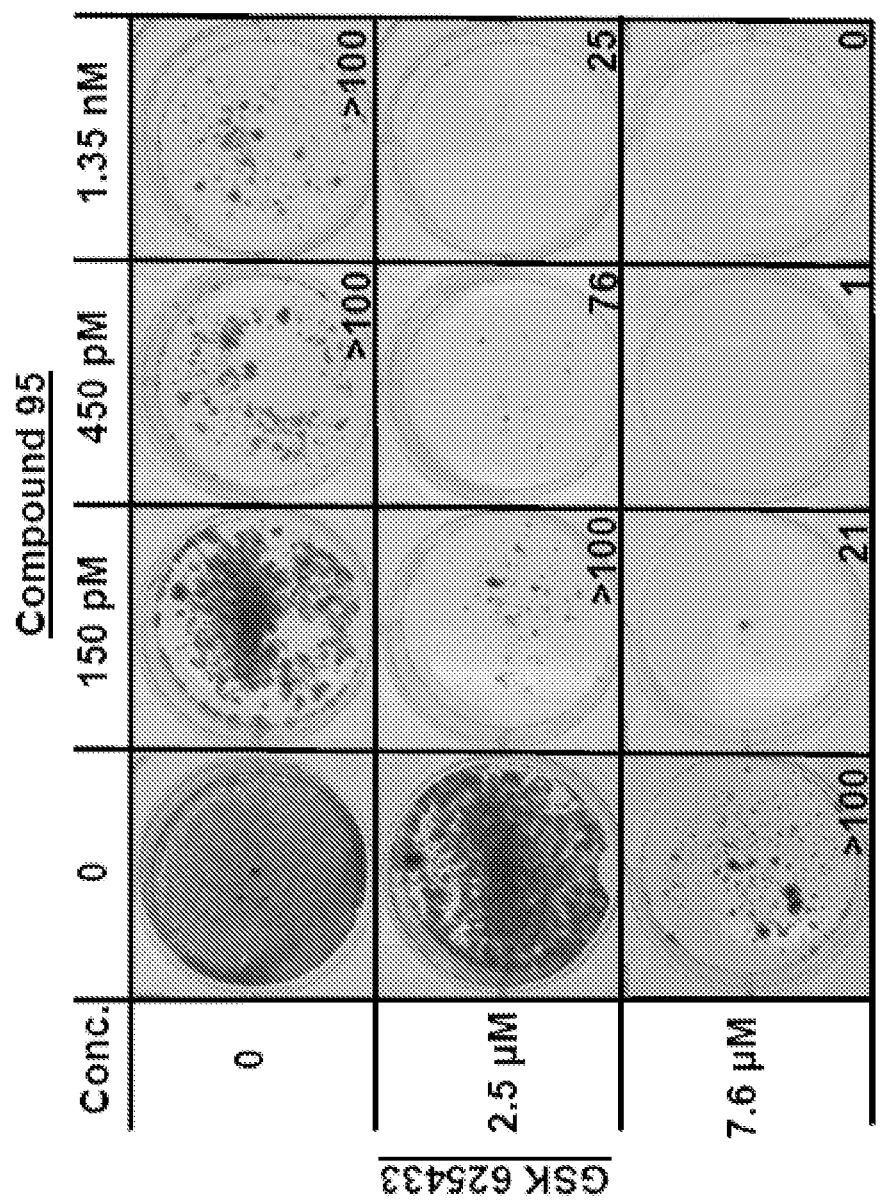
FIGS. 3A-3C shows photographs of macroscopic colonies and numbers of foci for cells (fixed and stained) incubated with the indicated concentrations of compounds or combination of compounds.
Figure 3B:
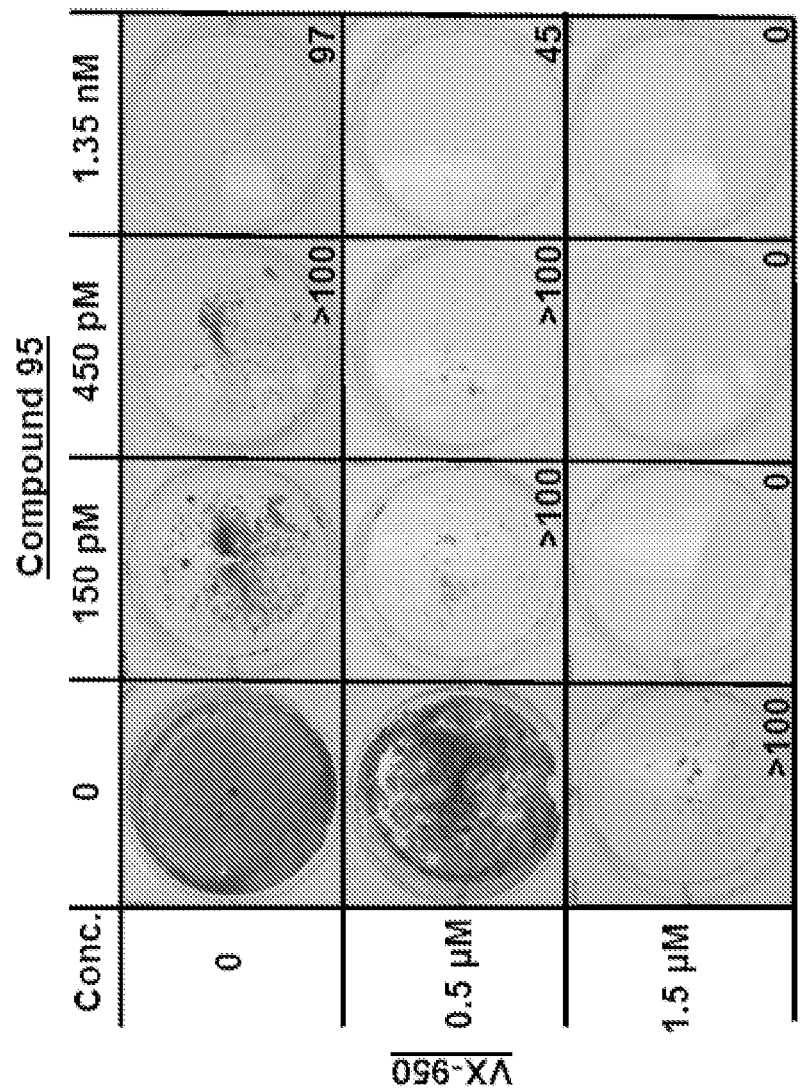
Figure 3C:
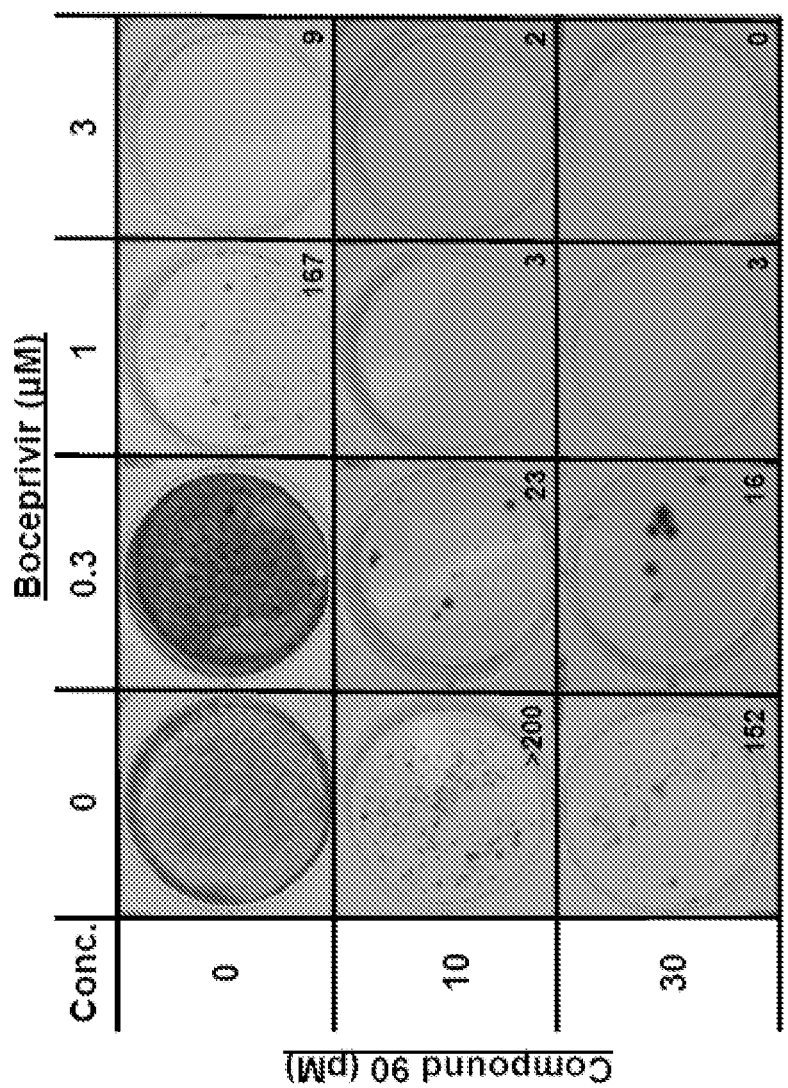

"SGR 11-7" replicon cells were cultured over 4-6 passages in the absence of G418 selection and in the presence of chemical agents at concentrations from between 1×EC50 to 30×EC50 of each chemical agent or combination. HCV replicon RNA was measured at each passage. Following the fourth or sixth passage, G418 was added to the cell culture medium and antiviral compounds were removed in order to identify any viral rebound and resulting cell outgrowth in the 27×EC50 of each chemical agent or combination. Compound 95 and either GSK 625433 or VX-950 were applied to gt1a replicon cells as single agents and in combination every 3-4 days to assess the ability of Compound 95 to suppress the emergence of resistance against VX-950 or GSK 625433. VX-950, GSK 625433, and Compound 95 were added at top concentrations of 1.5 µM, 7.6 µM, and 1.4 nM, respectively, and titrated down in 3-fold dilutions. Compound 90 and Boceprivir were applied to gt1b replicon cells as single agents and in combination every 3-4 days. Compound 90 and Boceprivir were added at top concentrations of 30 pM and 3.0 µM, respectively, and titrated in 3-fold dilutions. Independent replicates per experiment were conducted on 6-well plates. Cells were incubated with compound until the control sample (0.2% DMSO) reached confluence. Cells were subsequently passaged 1:12 to fresh 6-well plates and continuously cultured until macroscopic colonies were visible and G418-sensitive cells had died. The cells were subsequently fixed and stained with crystal violet/ethanol. Macroscopic colonies were counted and the numbers of foci are displayed in FIGS. 3A-3C.

These results demonstrate that combination treatment of replicon cells with HCV NS5A inhibitors and inhibitors targeting the HCV protease, HCV polymerase, cyclophilin (cyclosporine analogs), or interferon yields additive to synergistic antiviral effects. The ability to use these NS5A inhibitors in combination therapy can provide major advantages over single drug therapy for the treatment of HCV. Notably, combinations of NS5A inhibitors described herein with other direct antiviral compounds are more effective than single agents alone at eliminating viral RNA replication in replicon cells and at suppressing the development of HCV resistance.

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of molecular biology, medicine, immunology, pharmacology, virology, or related fields are intended to be within the scope of the invention.

While this invention has been particularly shown and described with references to preferred embodiments thereof, it will be understood by those skilled in the art that various changes in form and details may be made therein without departing from the scope of the invention encompassed by the appended claims.

What is claimed is:

1. A pharmaceutical composition comprising a pharmaceutically acceptable carrier or excipient, a therapeutically effective amount of a compound selected from compound 90 and compound 95 below,

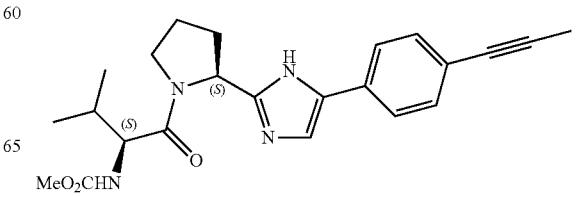

Compound 90

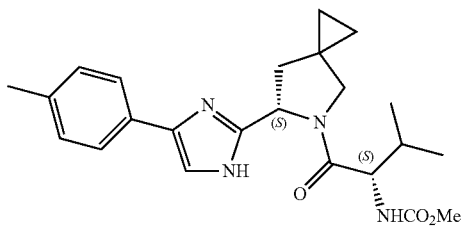

Compound 95

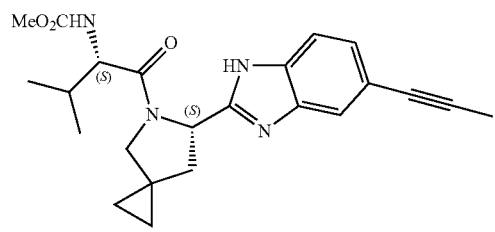

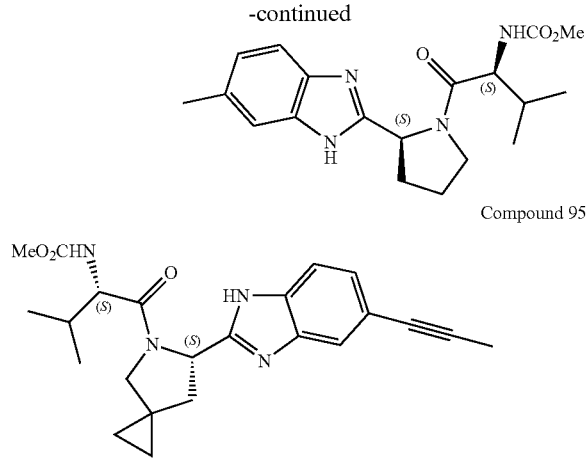

or a pharmaceutically acceptable salt thereof, and an additional agent selected from boceprevir and R7128 or a pharmaceutically acceptable salt thereof.

2. A pharmaceutical composition comprising a compound selected from the group consisting of Compound 90, Compound 93 and Compound 95;

Compound 90

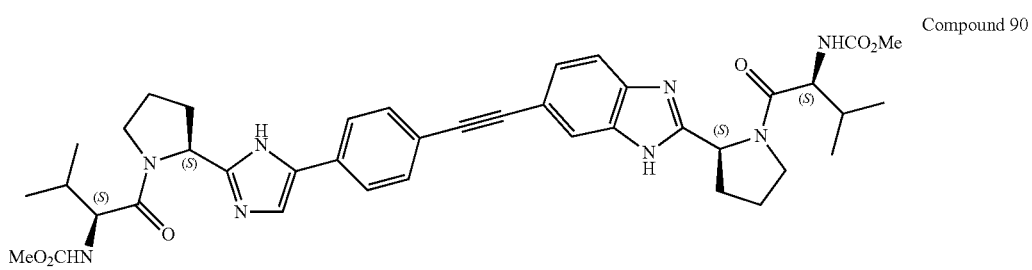

Compound 93

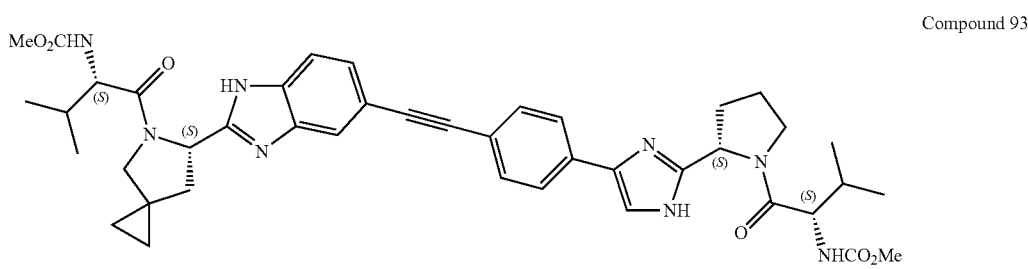

Compound 95

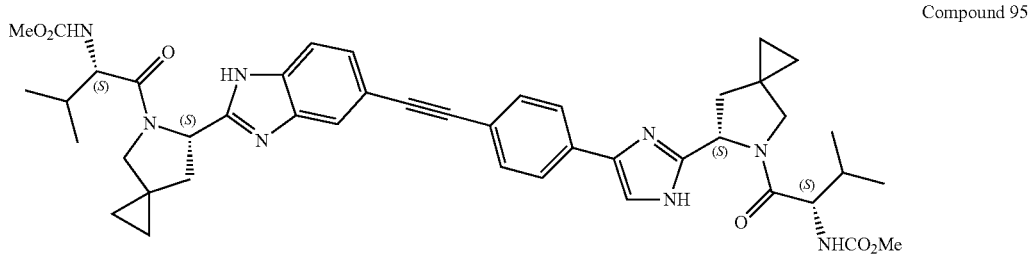

or a pharmaceutically acceptable salt thereof, and boceprevir or a pharmaceutically acceptable salt of any of thereof.

3. The pharmaceutical composition of claim 2, wherein the compound is Compound 95

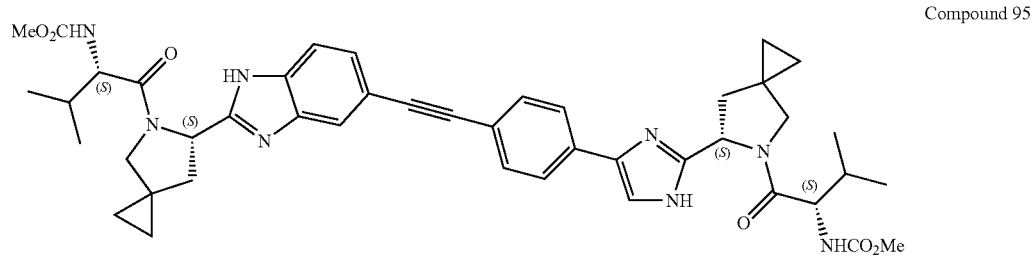

Compound 95 or a pharmaceutically acceptable salt thereof.

4. A composition comprising Compound 93;

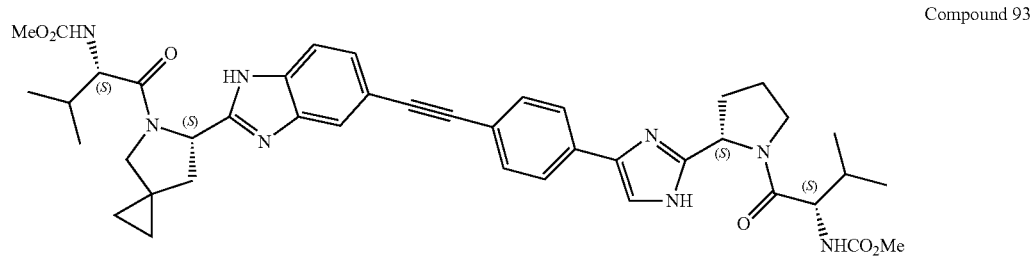

Compound 93 or a pharmaceutically acceptable salt thereof and an additional agent selected from the group consisting of boceprevir, interferon-α and GSK 625433, or a pharmaceutically acceptable salt thereof.

5. The pharmaceutical composition of claim 1, wherein the compound is Compound 90 or a pharmaceutically acceptable salt thereof.

6. The pharmaceutical composition of claim 1, wherein the compound is Compound 95 or a pharmaceutically acceptable salt thereof.

7. The pharmaceutical composition of claim 6, wherein the additional agent is R7128 or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 9,060,971 B2 | Page 1 of 1 |
| APPLICATION NO. | : 12/851350 | |
| DATED | : June 23, 2015 | |
| INVENTOR(S) | : Yat Sun Or et al. | |

It is certified that error appears in the above-identified patent and that said Letters Patent is hereby corrected as shown below:

In The Claims

At Column 82

At line 66, after the word salt, delete "of any of".

Signed and Sealed this
Twenty-fourth Day of November, 2015

Michelle K. Lee
*Director of the United States Patent and Trademark Office*

SEQUENCE LISTING

```
<160> NUMBER OF SEQ ID NOS: 3

<210> SEQ ID NO 1
<211> LENGTH: 18
<212> TYPE: DNA
<213> ORGANISM: Artificial Sequence
<220> FEATURE:
<223> OTHER INFORMATION: forward primer

<400> SEQUENCE: 1
gctgcggcct gtcgagct                                              18

<210> SEQ ID NO 2
<211> LENGTH: 19
<212> TYPE: DNA
<213> ORGANISM: Artificial Sequence
<220> FEATURE:
<223> OTHER INFORMATION: reverse primer

<400> SEQUENCE: 2
caaggtcgtc tccgcatac                                             19

<210> SEQ ID NO 3
<211> LENGTH: 25
<212> TYPE: DNA
<213> ORGANISM: Artificial Sequence
<220> FEATURE:
<223> OTHER INFORMATION: probe

<400> SEQUENCE: 3
cgaagctcca ggactgcacg atgct                                      25
```